United States Patent
Chichak et al.

(10) Patent No.: US 7,691,292 B2
(45) Date of Patent: Apr. 6, 2010

(54) ORGANIC IRIDIUM COMPOSITIONS AND THEIR USE IN ELECTRONIC DEVICES

(75) Inventors: Kelly Scott Chichak, Clifton Park, NY (US); Kyle Erik Litz, Ballston Spa, NY (US); James Anthony Cella, Clifton Park, NY (US); Joseph John Shiang, Niskayuna, NY (US); Qing Ye, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 279 days.

(21) Appl. No.: 11/504,871

(22) Filed: Aug. 16, 2006

(65) Prior Publication Data

US 2010/0051869 A1  Mar. 4, 2010

Related U.S. Application Data

(60) Provisional application No. 60/833,935, filed on Jul. 28, 2006.

(51) Int. Cl.
C09K 11/06 (2006.01)
H01L 51/54 (2006.01)

(52) U.S. Cl. .................... 252/301.16; 252/301.35; 548/403; 546/4; 546/10; 428/917; 313/504; 257/E51.044

(58) Field of Classification Search .................. 548/403
See application file for complete search history.

(56) References Cited

U.S. PATENT DOCUMENTS

| | | | |
|---|---|---|---|
| 3,995,299 | A | 11/1976 | Partridge |
| 6,097,147 | A | 8/2000 | Baldo et al. |
| 6,303,238 | B1 | 10/2001 | Thompson et al. |
| 6,815,091 | B2 | 11/2004 | Takiguchi et al. |
| 6,830,828 | B2 | 12/2004 | Thompson et al. |
| 6,921,915 | B2 | 7/2005 | Takiguchi et al. |
| 6,946,688 | B2 | 9/2005 | Grushin et al. |
| 6,989,273 | B2 | 1/2006 | Hsieh et al. |
| 2003/0096138 | A1 | 5/2003 | Lecloux et al. |
| 2004/0197600 | A1 | 10/2004 | Thompson et al. |
| 2005/0112406 | A1* | 5/2005 | Han et al. ................. 428/690 |
| 2008/0061684 | A1* | 3/2008 | Saitou et al. .............. 313/504 |

FOREIGN PATENT DOCUMENTS

| | | |
|---|---|---|
| EP | 1834956 A1 | 9/2007 |
| WO | WO 03/001616 | 1/2003 |
| WO | WO 2004/085450 | 10/2004 |
| WO | WO 2006/073112 | 7/2006 |

OTHER PUBLICATIONS

S. Sprouse et al., "Photophysical Effects of Metal-Carbon σ Bonds in Ortho-Metalated Complexes of Ir(III) and Rh(III)", J. Am. Chem. Soc., vol. 106, pp. 6647-6653, 1984.

K. A. King et al., "Excited-State Properties of a Triply Ortho-Metalated Iridium(III) Complex", J. Am. Chem. Soc., vol. 107, pp. 1431-1432, 1985.

Jae Il Kim et al., "Efficient Electrogenerated Chemiluminescence From Cyclometalated Iridium(III) Complexes", J. Am. Chem. Soc., vol. 127, No. 6, pp. 1614-1615, 2005.

Jiaxing Jiang et al., "High-Efficiency Electrophosphorescent Fluorene-alt-carbazole Copolymers N-Grafted With Cyclometalated Ir Complexes", Macromolecules, vol. 38, pp. 4072-4080, 2005.

Cheng-Hsien Yang et al., "Synthesis of a High-Efficiency Red Phosphorescent Emitter for Organic Light-Emitting Diodes", J. Mater. Chem., vol. 14, pp. 947-950, 2004.

Sergey Lamansky et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312, 2001.

Sergey Lamansky et al., Synthesis and Characterization of Phosphorescent Cyclometalated Iridium Complexes:, Inorg. Chem., vol. 40, pp. 1704-1711, 2001.

Micro G. Colombo et al., "Facial Tris Cyclometalated $Rh^{3+}$ and $Ir3+$ Complexes: Their Synthesis, Structure, and Optical Spectroscopic Properties", Inorg. Chem. vol. 33, pp. 545-550, 1994.

K. R. Justin Thomas et al., "Efficient Red-Emitting Cyclometalated Iridium(III) Complexes Containing Lepidine-Based Ligands", Inorganic Chemistry, vol. 44, No. 16, pp. 5677-5685, 2005.

Elisabeth Holder et al., "New Trends in the Use of Transition Metal-Ligand Complexes for Applications in Electroluminescent Devices", Advanced Materials, vol. 17, pp. 1109-1121, 2005.

Wai-Yeung Wong et al., "A Multifunctional Platinum-Based Triplet Emitter for OLED Appplications#", Organometallics, vol. 24, pp. 4079-4082, 2005.

Xiangjun Wang et al., "Electrophosphorescence From Substituted Poly(thiophene) Dopes With Iridium or Platinum Complex", Thin Solid Films, vol. 468, pp. 226-233, 2004.

(Continued)

Primary Examiner—Marie R. Yamnitzky
(74) Attorney, Agent, or Firm—Mary Louise Gioeni

(57) ABSTRACT

The present invention provides compositions comprising at least one novel organic iridium compound which comprises at least one cyclometallated ligand and at least one ketopyrrole ligand. The organic iridium compositions of the present invention are referred to as Type (1) organic iridium compositions and are constituted such that no ligand of the novel organic iridium compound has a number average molecular weight of 2,000 grams per mole or greater (as measured by gel permeation chromatography). Type (1) organic iridium compositions are referred to herein as comprising "organic iridium complexes". The novel organic iridium compositions are useful in optoelectronic electronic devices such as OLED devices and photovoltaic devices. In one aspect, the invention provides novel organic iridium compositions useful in the preparation of OLED devices exhibiting enhanced color properties and light output efficiencies.

22 Claims, 15 Drawing Sheets

OTHER PUBLICATIONS

Changyun Jiang et al., "High-Efficiency, Saturated Red-Phosphorescent Polymer Light-Emitting Diodes Based on Conjugated and Non-Conjugated Polymers Doped With an Ir Complex**", Advanced Materials, vol. 16, No. 6, pp. 537-541, 2004.

Eun Jeong Nam et al., "A Synthesis and Luminescence Study of Ir(ppz)$_3$ for Organic Light-Emitting Devices", The Chemical Society of Japan, Bull. Chem. Soc. Jpn., vol. 77, No. 4, pp. 751-755, 2004.

Akira Tsuboyama et al., "Homoleptic Cyclometalated Iridium Complexes With Highly Efficient Red Phosphorescence and Application to Organic Light-Emitting Diode", J. Am. Chem. Soc., vol. 125, pp. 12971-12979, 2003.

Ying-Ju Su et al., "Highly Efficient Red Electrophosphorescent Devices Based on Iridium Isoquinoline Complexes: Remarkable External Quantum Efficiency Over a Wide Range of Current**", Advanced Materials, vol. 15, No. 11, pp. 884-888, Jun. 5, 2003.

Weiguo Zhu et al., "Synthesis and Red Electrophosphorescence of a Novel Cyclometalated Iridium Complex in Polymer Light-Emitting Diodes", Thin Solid Films, vol. 446, pp. 128-131, 2004.

Ling Huang et al., "Bright Red Electroluminescent Devices Using Novel Second-Ligand-Contained Europium Complexes as Emitting Layers", J. Mater. Chem., vol. 11, pp. 790-793, 2001.

Chihaya Adachi et al., "Nearly 100% Internal Phosphorescence Efficiency in an Organic Light Emitting Device", Journal of Applied Physics, vol. 90, No. 10, pp. 5048-5051, Nov. 15, 2001.

M. A. Baldo et al., "Very High-Efficiency Green Organic Light-Emitting Devices Based on Electrophosphorescence", Applied Physics Letters, vol. 75, No. 1, pp. 4-6, Jul. 5, 1999.

Jian Li et al., "Synthetic Control of Excited-State Properties in Cyclometalated Ir(III) Complexes Using Ancillary Ligands", Inorganic Chemistry, vol. 44, pp. 1713-1727, 2005.

Youngmin You et al., "Inter-Ligand Energy Transfer and Related Emission Change in the Cyclometalated Heteroleptic Iridium Complex: Facile and Efficient Color Tuning Over the Whole Visible Range by the Ancillary Ligand Structure", J. Am. Chem. Soc., vol. 127, No. 36, pp. 12438-12439, 2005.

Albertus J. Sandee et al., "Solution-Processible Conjugated Electrophosphorescent Polymers", J. Am. Chem. Soc., vol. 126, pp. 7041-7048, 2004.

R. H. Friend et al., "Electroluminescence in Conjugated Polymers", Nature, vol. 397, pp. 121-128, Jan. 14, 1999.

Stephen R. Forrest, "Active Optoelectronics Using Thin-Film Organic Semiconductors", IEEE Journal on Selected Topics in Quantum Electronics, vol. 6, No. 6, pp. 1072-1083, 2000.

M. A. Baldo et al., "Highly Efficient Phosphorescent Emission From Organic Electroluminescent Devices", Nature, vol. 395, pp. 151-154, Sep. 10, 1998.

Xiaodong Wang et al., "Novel Iridium Complex and Its Copolymer With N-Vinyl Carbazole for Electroluminescent Devices", IEEE Journal on Selected Topics in Quantum Electronics, vol. 10, No. 1, pp. 121-126, 2004.

Entitled Electronic Devices Comprising Organic Iridium Compositions.; pub'd as US 2008/0026249 (Jan. 31, 2008).

Entitled Organic Iridium Compositions and Their Use in Electronic Devices; pub'd as US 2008/0023672 (Jan. 31, 2008).

Entitled Electronic Devices Comprising Organic Iridium Compositions; pub'd as US 2008/0026250 (Jan. 31, 2008).

Entitled Organic Iridium Compositions and Their Use in Electronic Devices ; pub'd as US 2008/0023671 (Jan. 31, 2008).

Entitled Electronic Devices Comprising Organic Iridium Compositions (U.S. Appl. No. 11/504,870, filed Aug. 16, 2006).

* cited by examiner

ORGANIC IRIDIUM COMPOSITIONS AND THEIR USE IN ELECTRONIC DEVICES

CROSS-REFERENCE TO RELATED APPLICATIONS

This Application claims priority to currently pending U.S. Provisional Application Ser. No. 60/833,935, filed Jul. 28, 2006.

STATEMENT REGARDING FEDERALLY SPONSORED RESEARCH & DEVELOPMENT

This invention was made with Government support under contract number DE-FC26-05NT42343. The Government has certain rights in the invention.

BACKGROUND

The invention includes embodiments that relate to organic iridium compositions, intermediates for the preparation of organic iridium compositions, and devices which incorporate organic iridium compositions. The invention includes embodiments that relate to organic iridium compositions useful as phosphor compositions.

Organic light emitting devices (OLEDs), which make use of thin film materials that emit light when subjected to a voltage bias, are expected to become an increasingly popular form of flat panel display technology. This is because OLEDs have a wide variety of potential applications, including cellphones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

Light emission from OLEDs typically occurs via electrofluorescence, i.e. light emission from a singlet excited state formed by applying a voltage bias across a ground state electroluminescent material. It is believed that OLEDs capable of producing light by an alternate mechanism, electrophosphorescence, i.e. light emission from a triplet excited state formed by applying a voltage bias across a ground state electrofluorescecent material, will exhibit substantially higher quantum efficiencies than OLEDs that produce light primarily by electrofluorescence. Light emission from OLEDs by electrophosphorescence is limited since the triplet excited states in most light emitting organic materials are strongly disposed to non-radiative relaxation to the ground state. Thus, electrophosphorescent materials hold promise as key components of OLED devices and other optoelectronic devices exhibiting greater efficiencies relative to the current state of the art. For example, OLEDs capable of light production by electrophosphorescence are expected to exhibit a reduction (relative to OLEDs which produce light primarily by electrofluorescence) in the amount of energy lost to radiationless decay processes within the device thereby providing an additional measure of temperature control during operation of the OLED.

Improved light emission efficiencies have been achieved by incorporating a phosphorescent platinum-containing dye in an organic electroluminescent device such as an OLED (See Baldo et al., "Highly Efficient Phosphorescent Emission from Organic Electroluminescent Devices", Nature, vol. 395, 151-154, 1998) and phosphorescent iridium-containing dyes have also been employed (See for example Lecloux et al. United States Patent Application 20030096138, May 22, 2003). Notwithstanding earlier developments, there is currently considerable interest in finding novel phosphorescent materials which not only increase efficiency but also provide for a greater measure of control of the color of light produced by an OLED. For example, it would be highly desirable to provide novel phosphorescent materials which enable organic electroluminescent devices having improved overall efficiency, while at the same time allowing for the light output to be red shifted or blue shifted, depending on the nature of the application.

BRIEF DESCRIPTION

The invention provides a novel class of organic iridium compounds, and demonstrates the utility of these materials in organic electroluminescent devices. Thus, in one embodiment, the invention provides a composition comprising at least one organic iridium complex comprising:
(i) at least one cyclometallated ligand; and
(ii) at least one ketopyrrole ligand.

In another embodiment, the present invention provides an electrophosphorescent composition comprising at least one electroactive host material and at least one organic iridium complex comprising:
(i) at least one cyclometallated ligand; and
(ii) at least one ketopyrrole ligand.

In yet another embodiment, the present invention provides an organic iridium complex having structure XIV.

These and other features, aspects, and advantages of the present invention may be more understood more readily by reference to the following detailed description.

DETAILED DESCRIPTION

Figure 1:
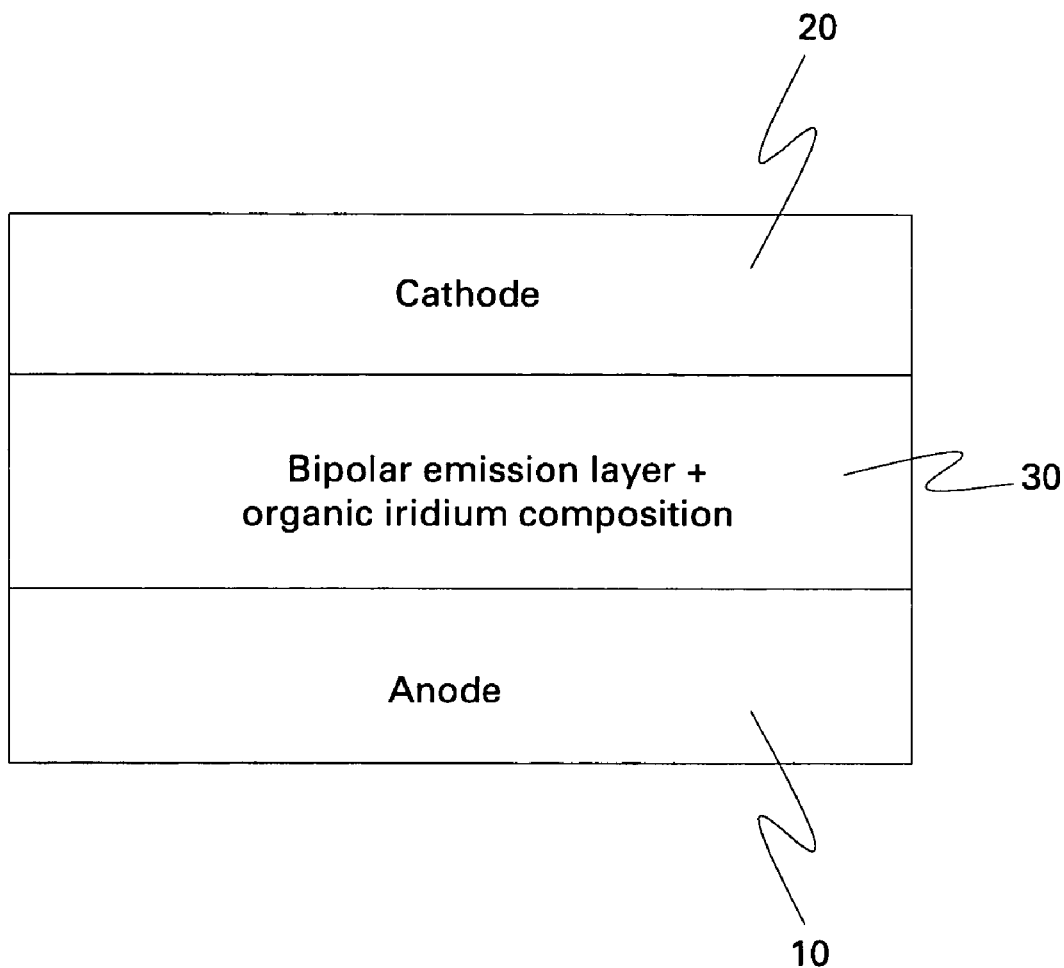
FIG. 1 represents an OLED device provided by the present invention.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H$ oC(CF$_3$)$_2$ $C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$C$_6$H$_{10}$—), 4-aminocarbonylcyclopent-1-yl (i.e., NH$_2$COC$_5$H$_8$-), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy(2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6$H$_{10}$—), 4-vinylcyclohexen-1-yl, vinylidenebis (cyclohexyl), and the like. The term "a C$_3$-C$_{10}$ cycloaliphatic radical" includes cycloaliphatic radicals containing at least three but no more than 10 carbon atoms. The cycloaliphatic radical 2-tetrahydrofuranyl(C$_4$H$_7$O—) represents a C$_4$ cycloaliphatic radical. The cyclohexylmethyl radical (C$_6$H$_{11}$CH$_2$—) represents a C$_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a C$_6$ aliphatic radical comprising a methyl group, the methyl group being a functional group which is an alkyl group. Similarly, the 4-nitrobut-1-yl group is a C$_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e., —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

As used herein, the term "electroactive material" refers to organic materials which may be polymeric or non-polymeric, and which are susceptible to charge conduction when subjected to a voltage bias, for example organic materials which conduct electrons and/or holes in an organic light emitting device (OLED). Electroactive materials include, for example, organic semiconducting polymers. Those skilled in the art will appreciate that while electroluminescent materials represent a class of electroactive materials, a material need not be electroluminescent to be electroactive.

As used herein, the term "organic iridium composition" is defined as composition comprising an iridium ion bound to at least one organic ligand. For example, the chloride-bridged cyclometallated iridium dimers {(piq)$_2$Ir(μ-Cl)}$_2$ and {(ppy)$_2$Ir(μ-Cl)}$_2$ each represents an organic iridium composition comprising two iridium ions bound to the cyclometallated ligands "piq" or "ppy". Cyclometallated ligands "piq" or "ppy" may be derived from 1-phenylisoquinoline and 2-phenylpyridine respectively. The organic iridium compositions of the present invention comprise an iridium ion bound to at least one cyclometallated ligand and at least one ketopyrrole ligand. The organic iridium compositions of the present invention are of two types: Type (1) wherein neither of the cyclometallated ligand and the ketopyrrole ligand has a number average molecular weight of 2,000 grams per mole or greater (as measured by gel permeation chromatography), and Type (2) wherein at least one of the cyclometallated ligand and the ketopyrrole ligand has a number average molecular weight of 2,000 grams per mole or greater (as measured by gel permeation chromatography). Type (1) organic iridium compositions are referred to herein as comprising "organic iridium complexes". Type (2) organic iridium compositions are referred to herein as comprising "polymeric organic iridium complexes".

The organic iridium compositions of both Type (1) and Type (2) are at times referred to herein as "cyclometallated iridium complexes" because they comprise at least one cyclometallated ligand. A ligand is "cyclometallated" when it binds to a metal ion via a carbon-metal bond and at least one additional bond. For example, the organic iridium complex {(ppy)$_2$Ir(BP)} comprises two cyclometallated "ppy" ligands and a non-cyclometallated ligand, "BP", said non-cyclometallated ligand, "BP", being derived from 2-benzoylpyrrole. The cyclometallated "ppy" ligand may be represented as

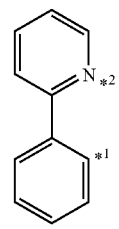

wherein the asterisks signal the points of attachment of cyclometallated ligand to the metal via a carbon-metal bond at *1 and a nitrogen-metal bond at *2. In the example just given, the cyclometallated ligand "ppy" has formula C$_{11}$H$_8$N and is related to, but is not identical to, the neutral molecule 2-phenylpyridine which has formula C$_{11}$H$_9$N. Those skilled in the art will appreciate that at least in a formal sense, the cyclometallated ligand represents a carbanionic species. As noted, a cyclometallated ligand is a ligand that binds to a metal ion via a carbon-metal bond and at least one additional bond. In the example just given *2 represents the site of the additional bond between the cyclometallated ligand and the metal ion.

In one embodiment, the present invention provides a composition comprising at least one organic iridium complex comprising:

(i) at least one cyclometallated ligand; and (ii) at least one ketopyrrole ligand.

In another embodiment, the present invention provides an organic iridium complex having structure I

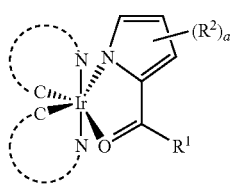

I wherein each of the ligands

is independently at each occurrence a cyclometallated ligand which may be the same or different;

$R^1$ is a $C_3$-$C_{40}$ aromatic radical, a $C_1$-$C_{50}$, aliphatic radical, or a $C_3$-$C_{40}$ cycloaliphatic radical;

$R^2$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical; and "a" is an integer from 0 to 3.

Organic iridium complexes having structure I are exemplified in Table 1. The exemplary organic iridium complexes 1a-1e in Table 1 illustrate instances in which the ketopyrrole ligand, sometimes referred to as the "ancillary ligand", may be derived from an alkanoyl pyrrole (See Entry 1a, derived from 2-butanoylpyrrole) or a 2-benzoylpyrrole (Entries 1b-1d). The exemplary organic iridium complexes 1a-1d in Table 1 further illustrate instances in which the cyclometallated ligands are identical. For example, in Entry 1a each of the cyclometallated ligands is derived from 1-(4-bromophenyl)isoquinoline. In various embodiments of the present invention, however, the cyclometallated ligands need not be identical, for example the organic iridium complex shown in Entry 1e is an organic iridium complex which comprises a cyclometallated ligand derived from 2-phenylpyridine and a cyclometallated ligand derived from 4-dimethylamino-2-phenylpyridine.

TABLE 1

Exemplary Organic Iridium Complexes Having Structure I

| Entry | Ketopyrrole Ligand Structure | Cyclometallated Ligand Structure |
|---|---|---|
| 1a | | |
| 1b | | |
| 1c | | |

TABLE 1-continued

Exemplary Organic Iridium Complexes Having Structure I

| Entry | Ketopyrrole Ligand Structure | Cyclometallated Ligand Structure |
|---|---|---|
| 1d | | |
| 1e | | |

Those skilled in the art will appreciate that structure I encompasses iridium complexes which are chiral. Unless expressly stated otherwise, as used herein structure I and all other structures contained in this disclosure which suggest an absolute stereochemistry (e.g. structure XIII) include the structure shown and its mirror image structure. In addition, the present invention also provides enantiomerically pure (i.e. a single enantiomer is present) organic iridium complexes comprising at least one cyclometallated ligand and at least one ketopyrrole ligand. Enantiomerically pure organic iridium complexes provided by the present invention may be prepared from the corresponding racemic mixture by high performance liquid chromatography (hplc) using a chiral stationary phase, for example. Those skilled in the art will appreciate that a wide variety of hplc columns capable of effecting the separation a racemic mixture of an organic iridium complex into its component enantiomers are commercially available, for example the CHIRAL AGP column available from Chromtech Ltd. (United Kingdom). In addition, the present invention provides enantiomerically enriched organic iridium complexes comprising at least one cyclometallated ligand and at least one ketopyrrole ligand. Those skilled in the art will appreciate that enantiomerically enriched organic iridium complexes may be prepared from the corresponding racemic mixture via a variety of means such as by high performance liquid chromatography (hplc) using a chiral stationary phase. Thus in one embodiment, the present invention provides an organic iridium complex represented by structure I which is enantiomerically pure, for example compounds 1a-1d (Table 1) possessing the absolute stereochemistry depicted in structure I. In an alternate embodiment, the present invention provides an organic iridium complex represented by structure I which is enantiomerically pure, for example compounds 1a-1d (Table 1) possessing the absolute stereochemistry which is the mirror image of that depicted in structure I. In addition to racemic mixtures, pure enantiomers, and enantiomerically enriched compositions, the present invention also provides organic iridium complexes in the form of diastereomeric mixtures, materials which at times may present solubility or other advantages. In addition, although structures I and XIII show the nitrogen atoms of the cyclometallated ligands as occupying coordination positions having a trans-relationship, alternate configurations are possible. For example, the nitrogen atoms of the cyclometallated ligands of structure I,

may also occupy coordination positions having a cis-relationship.

As noted, the organic iridium complexes provided by the present invention comprise at least one cyclometallated ligand. The compositions of Entries 1a-1e of Table 1 illustrate a variety of cyclometallated ligands which may be present in the organic iridium complexes of the present invention. In one embodiment, the cyclometallated ligand is derived from a phenylisoquinoline having structure II

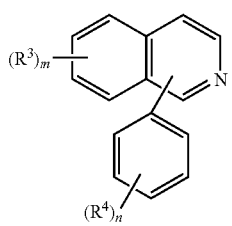

II wherein $R^3$ and $R^4$ are independently at each occurrence a deuterium atom, a halogen, a nitro group, an amino group, a $C_3$-$C_{40}$ aromatic radical, a $C_1$-$C_{50}$ aliphatic radical, or a $C_3$-$C_4$ cycloaliphatic radical;

"m" is an integer from 0 to 6; and "n" is an integer ranging from 0 to 5.

The compositions of Entries 2a-2h of Table 2 illustrate a variety of neutral isoquinolines having structure II which may serve as precursors to the cyclometallated ligands of the organic iridium compositions of the present invention. For instance, Entry 2a of Table 2 represents the parent (unsubstituted) 1-phenylisoquinoline which may serve as the precursor to the cyclometallated ligand present in certain embodiments of the present invention. Entry 2a also shows the numbering scheme used herein to describe phenylisoquinoline systems. Entry 2b represents the parent 3-phenylisoquinoline which may serve as the precursor to the cyclometallated ligand present in certain embodiments of the present invention.

TABLE 2

Phenylisoquinoline Precursors to Cyclometallated Ligands

| Entry | $R^3$ | $R^4$ | m | n | Structure |
|-------|-------|-------|---|---|-----------|
| 2a | — | — | 0 | 0 | 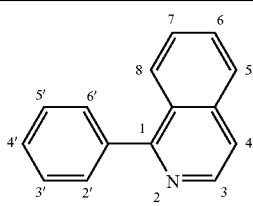 |
| 2b | — | — | 0 | 0 | 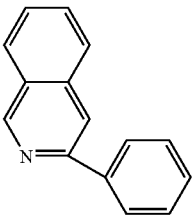 |
| 2c | — | Me | 0 | 1 | 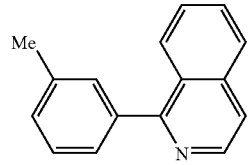 |
| 2d | $CF_3$ | Me | 1 | 1 | 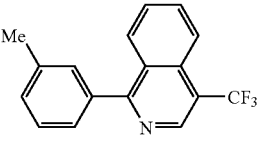 |
| 2e | — | sec-butyl | 0 | 1 | 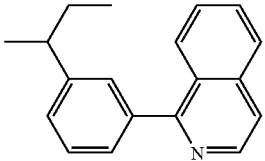 |
| 2f | iso-propyl | — | 1 | 0 | 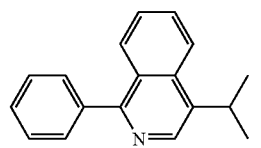 |
| 2g | phenyl | — | 1 | 0 | 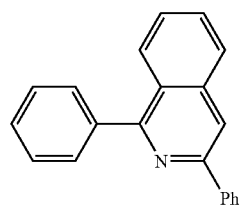 |
| 2h | phenyl | phenyl | 1 | 1 | 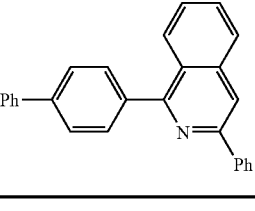 |

In one embodiment, the present invention provides an organic iridium complex comprising at least one cyclometallated ligand derived from a 2-phenyl pyridine compound having structure III

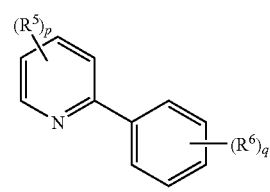

III wherein $R^5$ and $R^6$ are independently at each occurrence a deuterium atom, a halogen, a nitro group, an amino group, $C_3$-$C_{40}$ aromatic radical, a $C_1$-$C_{50}$ aliphatic radical, or a $C_3$-$C_{40}$ cycloaliphatic radical;

"p" is an integer from 0 to 4: and "q" is on integer from 0 to 5.

The compositions of Entries 3a-3f of Table 3 illustrate a variety of 2-phenylpyridines III which may serve as precursors to the cyclometallated ligands of the organic iridium compositions of the present invention. The composition of Entry 3a illustrates the parent 2-phenylpyridine and the numbering scheme used to describe phenylpyridines. The composition of Entry 3b illustrates 2,6-diphenylpyridine. The composition of Entry 3e illustrates a polysubstituted 2-phenylpyridine in which with reference to generic structure III, $R^5$ is a trifluoromethyl group, "p" is 1, and $R^6$ is independently a bromine group and a methyl group and "q" is 2. The composition of Entry 3f illustrates an embodiment in which $R^5$ is independently a chlorine group and a methyl group, and "p" is 2. The composition of Entry 3f further illustrates an embodiment in which $R^6$ is a divalent $C_1$ aliphatic radical, —$OC_1H_2O$—, which is attached at the 3'- and 4'-positions of the phenyl ring.

TABLE 3

2-Phenylpyridine Precursors to Cyclometallated Ligands

| Entry | $R^5$ | $R^6$ | p | q | Structure |
|---|---|---|---|---|---|
| 3a | — | — | 0 | 0 | 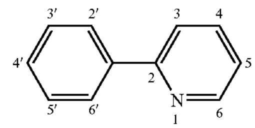 |
| 3b | Ph | — | 1 | 0 | 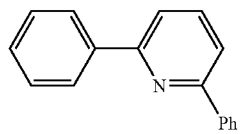 |
| 3c | $Me_2N$— | — | 1 | 0 | 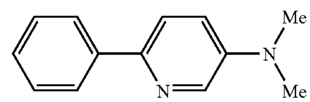 |
| 3d | — | Me | 0 | 1 | 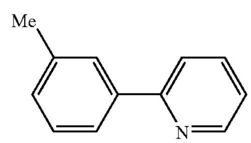 |
| 3e | $CF_3$ | Br, Me | 1 | 2 | 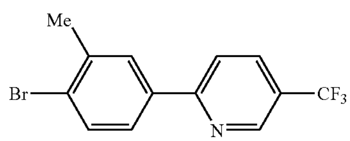 |
| 3f | Cl, Me | $OC_1H_2O$ | 2 | 1 | 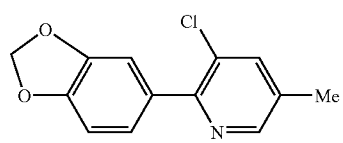 |

In one embodiment, the present invention provides an organic iridium complex comprising at least one cyclometallated ligand derived from a styryl-isoquinoline compound having structure IV

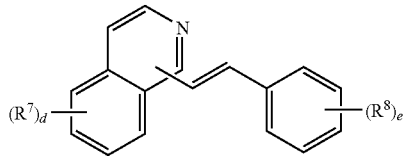

IV wherein $R^7$ and $R^8$ are independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"d" is an integer from 0 to 6; and "e" is an integer from 0 to 5.

The composition of Entry 4a illustrates the parent 1-styryl-isoquinoline and the numbering system used to describe styrylisoquinolines generally. The composition of Entry 4b illustrates 3-styrylisoquinoline. The compositions of Entries 4c and 4d illustrate a substituted 3-styrylisoquinoline and a substituted 1-styrylisoquinoline respectively.

TABLE 4

Styrylisoquinoline Precursors to Cyclometallated Ligands

| Entry | $R^7$ | $R^8$ | d | e | Structure |
|---|---|---|---|---|---|
| 4a | — | — | 0 | 0 | 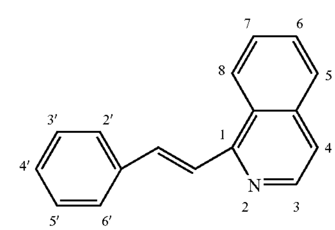 |
| 4b | — | — | 0 | 0 | 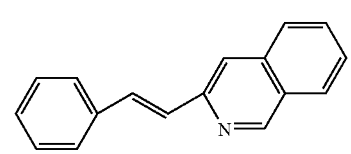 |

TABLE 4-continued

Styrylisoquinoline Precursors to Cyclometallated Ligands

| Entry | R[7] | R[8] | d | e | Structure |
|---|---|---|---|---|---|
| 4c | — | CF$_3$ | 0 | 1 | (structure shown) |
| 4d | Cl | Et | 1 | 1 | (structure shown) |

From the foregoing discussion it will be understood by those skilled in the art that in one embodiment, the cyclometallated ligand may be derived from a 1-phenylisoquinoline derivative (e.g. 1-phenylisoquinoline), a 3-phenylisoquinoline derivative (e.g. 3-phenylisoquinoline), a 2-phenylpyridine derivative (e.g. 2-phenylpyridine), 1-styrylisoquinoline derivative (e.g. 1-styrylisoquinoline), a 3-styrylisoquinoline derivative (e.g. 3-styrylisoquinoline), or a combination thereof. In the present context the phrase "or a combination thereof" means that two or more cyclometallated ligands are derived from two or more of the enumerated precursors; a 1-phenylisoquinoline, a 3-phenylisoquinoline, a 2-phenylpyridine, a 1-styrylisoquinoline, and a 3-styrylisoquinoline. Generally, as used herein, when it follows an enumerated group of choices, the phrase "or a combination thereof" means that that two or more of the choices may be combined in an embodiment.

It will be apparent to those skilled in the art that a wide variety of additional precursors to cyclometallated ligands are possible, for example 2-phenylquinoline, 2-styrylpyridine; 2-phenyl-4,4'-bipyridine; 2-(2'-thienyl)pyridine; and like compositions which juxtapose a chelating nitrogen atom with a C—H bond susceptible to metallation in a manner analogous to that observed in systems like 1-phenylisoquinoline, 2-phenylpyridine, 1-styrylpyridine, and 3-styrylisoquinoline. Additional precursors to cyclometallated ligands are illustrated in Table 5.

TABLE 5

Additional Examples of Neutral Precursors to Cyclometallated Ligands 5a (structure shown)

5b (structure shown)

TABLE 5-continued

Additional Examples of Neutral Precursors to Cyclometallated Ligands 5c (structure shown)

5d (structure shown)

5e (structure shown)

"coumarin 6" 5f (structure shown)

5g (structure shown)

5h (structure shown)

5i (structure shown)

5j (structure shown)

5k (structure shown)

TABLE 5-continued

Additional Examples of Neutral Precursors to Cyclometallated Ligands

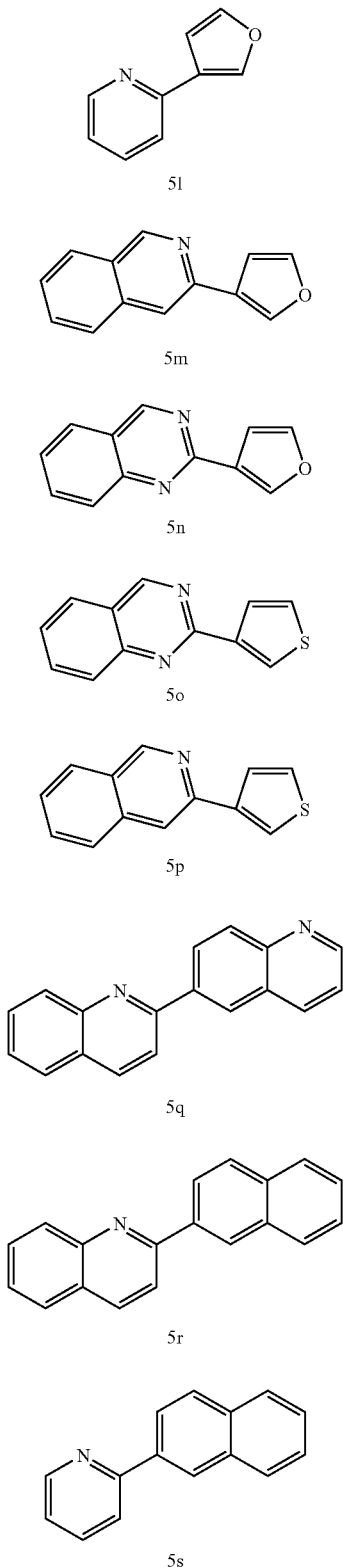

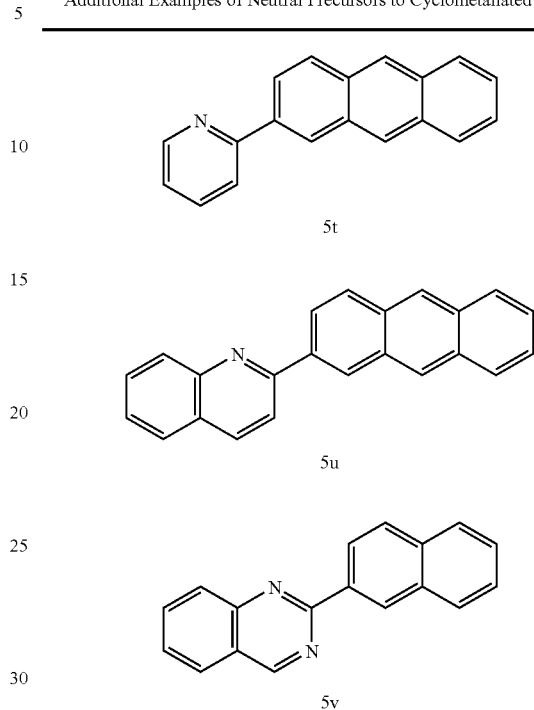

Among the precursors to cyclometallated ligands presented in Table 5 above, Entry 5f (coumarin 6, CAS No. 38215-36-0), is a highly fluorescent compound displaying a fluorescence maximum at about 500 nanometers (nm) in ethanol solution at an excitation wavelength of 420 (nm) with a quantum yield of about 0.78. In one embodiment, the present invention provides an organic iridium composition comprising at least one ketopyrrole ligand and at least one cyclometallated ligand derived from coumarin 6.

Precursors from which the cyclometallated ligands may be derived are in many instances available commercially. Alternately, cyclometallated ligand precursors may be prepared by methods known to those skilled in the art. For, example, 1-phenylisoquinoline may be made by reacting 1,1-diphenyl methylamine and 2,2-diethoxy acetaldehyde in the presence of an acid catalyst, as shown in Scheme 1.

Scheme 1

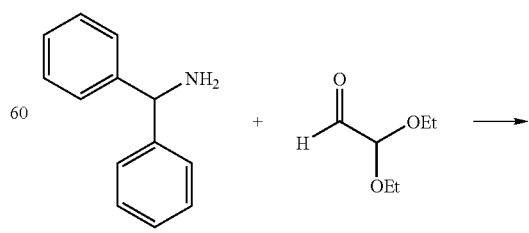

-continued

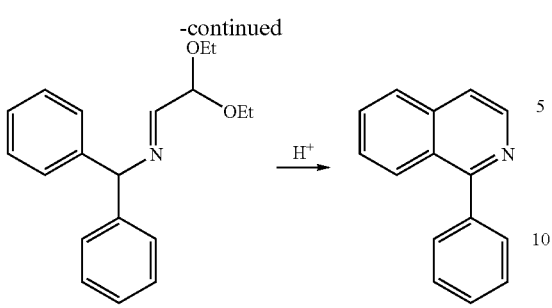

The cyclometallated ligand precursor 3-phenylisoquinoline may be prepared via an acid catalyzed reaction between benzaldehyde and 1-phenyl-2,2-diethoxy ethyl amine, as shown in Scheme 2.

Scheme 2

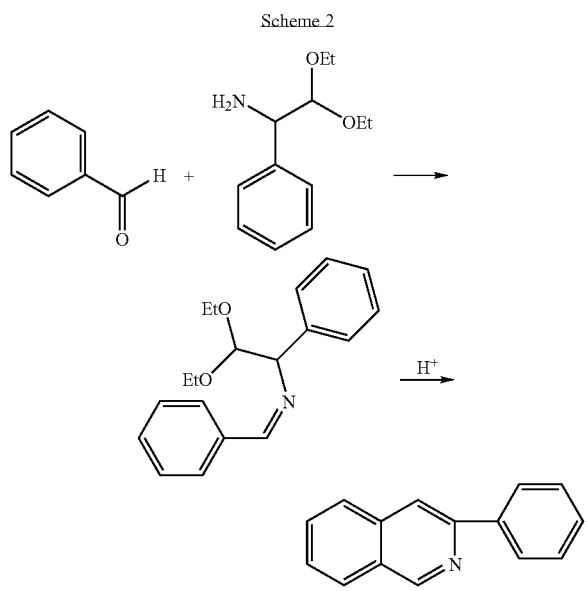

Those skilled in the art will understand that the transformations depicted in Schemes 1 and 2 may be applied to the preparation of a wide variety of substituted 1-phenylisoquinolines and 3-phenylisoquinolines, and additional synthetic routs to cyclometallated ligand precursors are readily available in the chemical literature.

Alternate methods for the preparation of cyclometallated ligand precursors include reaction of a bromoisoquinoline with a phenyl boronic acid using the well known Suzuki coupling methodology. Phenylpyridines may be prepared analogously. Other methods known to those skilled in the art include the Bischler-Napieralski reaction, Pictet-Gams isoquinoline synthesis, and the like.

Numerous 2-phenylpyridine derivatives III which may serve as precursors to the cyclometallated ligands of the organic iridium compositions of the present invention are commercially available or may be synthesized following standard synthetic procedures known to those skilled in the art.

Similarly, numerous styrylisoquinoline derivatives IV which may serve as the precursors to the cyclometallated ligands of the organic iridium compositions of the present invention are commercially available or may be synthesized following standard synthetic procedures known to those skilled in the art.

In one embodiment, the present invention provides an organic iridium complex comprising at least one cyclometallated ligand; and at least one ketopyrrole ligand, wherein the ketopyrrole ligand is derived from a ketopyrrole having structure V

V

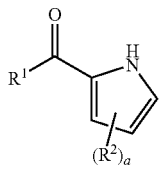

wherein $R^1$ is a $C_3$-$C_{40}$ aromatic radical, a $C_1$-$C_{50}$ aliphatic radical, or a $C_3$-$C_{40}$ cycloaliphatic radical;

$R^2$ is independently at each occurrence a deuterium atom, a halogen, a nitro group, on amino group, a $C_3$-$C_{40}$ aromatic radical, a $C_1$-$C_{50}$ aliphatic radical, or a $C_3$-$C_{40}$ cycloaliphatic radical; and "a" is an integer from 0 to 3.

The compositions of Entries 6a-6d of Table 6 illustrate a variety of ketopyrroles from which the ketopyrrole ligand of the organic iridium compositions of the present invention may be derived. For example, the composition of Entry 6a illustrates 2-acetylpyrrole. The composition of Entry 6b illustrates 2-pivaloylpyrrole. The composition of Entry 6c, 2-cyclohexanoyl-5-methylpyrrole, illustrates a ketopyrrole in which $R^1$ is cyclohexyl and $R^2$ is methyl, and "a" is 1. The composition of Entry 6d, 2-cyclopropanoyl-3-chloro-5-methylpyrrole, illustrates a ketopyrrole in which $R^1$ is cyclopropyl, and $R^2$ is independently chloro and methyl, and "a" is 2. Those skilled in the art will appreciate that the individual species presented in Table 6 are illustrative only, and that many additional ketopyrrole structures are possible, and that in light of the teachings herein, these additional ketopyrroles would be useful in the preparation of the organic iridium complexes provided by the present invention.

TABLE 6

Ketopyrrole Precursors to Ketopyrrole Ligands

| Entry | $R^1$ | $R^2$ | a | Structure |
|---|---|---|---|---|
| 6a | $CH_3$ | — | 0 | 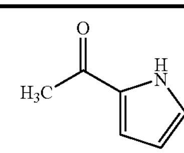 |
| 6b | t-Bu | — | 0 | 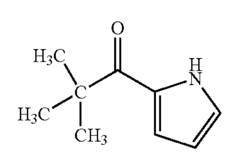 |

TABLE 6-continued

Ketopyrrole Precursors to Ketopyrrole Ligands

| Entry | $R^1$ | $R^2$ | a | Structure |
|---|---|---|---|---|
| 6c | Cyclohexyl | $CH_3$ | 1 | 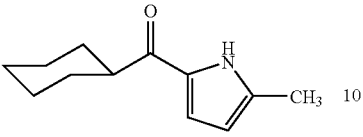 |
| 6d | Cyclopropyl | Cl, $CH_3$ | 2 | 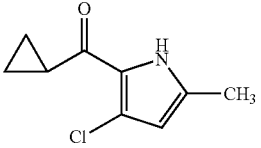 |

In another embodiment, the present invention provides an organic iridium complex comprising at least one cyclometallated ligand; and at least one ketopyrrole ligand, wherein the ketopyrrole ligand is derived from a benzoylpyrrole having structure VI

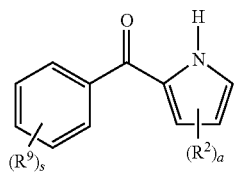

VI wherein $R^2$ and $R^9$ are independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3; and "s" is an integer from 0 to 5.

The compositions of Entries 7a-7f of Table 7 illustrate a variety of benzoylpyrroles from which the ketopyrrole ligand of the organic iridium compositions of the present invention may be derived. The composition of Entry 7a illustrates the parent (unsubstituted) 2-benzoylpyrrole (See also Table 1, Entry 1b) and the numbering scheme used for benzoylpyrroles generally. The composition of Entry 7b illustrates a 2-(4-bromobenzoyl)pyrrole wherein "a" is 0, "s" is 1 and $R^9$ is bromo. The composition of Entry 7c illustrates a 2-(3,5-dibromobenzoyl)-4-tert-butypyrrole wherein $R^2$ is tert-butyl, "a" is 1, $R^9$ is bromo, and "s" is 2. The composition of Entry 7d, 2-(3-phenylbenzoyl)pyrrole, illustrates a benzoylpyrrole in which "a" is 0, $R^9$ is phenyl and "s" is 1. In certain instances, the benzoylpyrroles themselves represent novel chemical structures, for example the compositions of Entries 7e and 7f. Benzoylpyrroles 7e and 7f are useful in the preparation of the organic iridium complexes of the present invention as is demonstrated herein. Those skilled in the art will appreciate that the individual species presented in Table 7 are illustrative only, and that many additional ketopyrrole structures are possible, and that in light of the teachings herein, these additional ketopyrroles would be useful in the preparation of the organic iridium complexes provided by the present invention.

TABLE 7

Benzoylpyrrole Precursors to Ketopyrrole Ligands

| Entry | $R^2$ | $R^9$ | a | s | Structure |
|---|---|---|---|---|---|
| 7a | — | — | 0 | 0 | 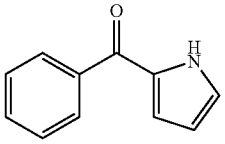 |
| 7b | — | Br | 0 | 1 | 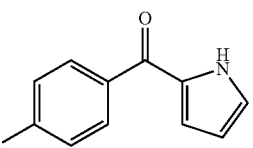 |
| 7c | t-Bu | Br, Br | 1 | 2 | 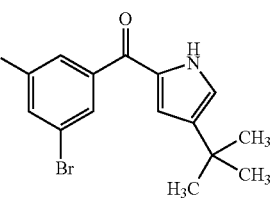 |
| 7d | — | Ph | 0 | 1 | 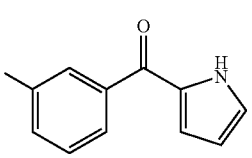 |
| 7e | — | Br, Br | 0 | 2 | 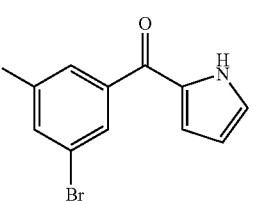 |
| 7f | — | OH, OH | 0 | 2 | 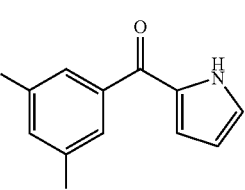 |

Ketopyrroles, for example 2-benzoylpyrrole, may be synthesized by methods known to those skilled in the art. A common method of preparation includes electrophilic addition of a suitable carbonyl reagent to a pyrrole ring. For example, benzoylpyrrole may be prepared by Vilsmeier-Hack aroylation of pyrrole with N,N-diethylbenzamide (See Examples section herein). The Examples section of this disclosure provides detailed guidance on the preparation of a wide variety of ketopyrroles which may be used to make the organic iridium compositions of the present invention.

In one embodiment, the organic iridium complexes of the present invention may be prepared using the ligand precursors discussed herein as follows. First, a cyclometallated ligand precursor such as 1-phenylisoquinoline is heated with iridium (III) chloride (IrCl₃) in the presence of a solvent such as aqueous 2-methoxyethanol, to afford the chloride-bridged cyclometallated iridium dimer intermediate (e.g. {(piq)₂Ir(μ-

Cl)}$_2$). The chloride-bridged cyclometallated iridium dimer intermediate may be reacted with a ketopyrrole in the presence of a base to afford the corresponding organic iridium complex comprising two cyclometallated ligands and an ancillary ligand derived from a ketopyrrole (a ketopyrrolic ligand).

In one embodiment, the present invention provides an organic iridium complex having structure VII

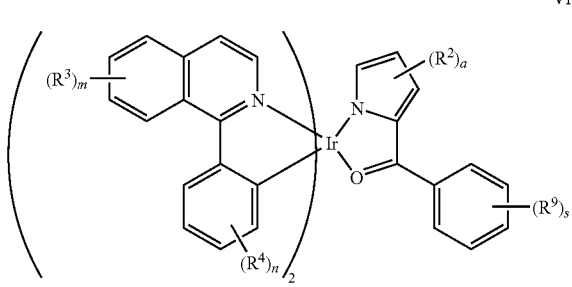

wherein $R^2$, $R^3$, $R^4$, $R^9$ are independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ radical;

"a" is an integer from 0 to 3: "m" is an integer from 0 to 6: "n" is an integer from 0 to 4; and "s" is an integer from 0 to 5.

Exemplary organic iridium complexes having structure VII are provided in Table 8. The composition of Entry 8a illustrates an organic iridium complex of the present invention wherein the ketopyrrole ligand comprises a trifluoromethyl group ("a"=0, $R^9$=$CF_3$, "s"=1) and the cyclometallated ligands are derived from 1-phenylisoquinoline ("m"=0, "n"=0). The composition of Entry 8b illustrates an organic iridium complex of the present invention wherein the ketopyrrole ligand comprises a methyl group and a trifluoromethyl group ($R^2$=$CH_3$ "a"=1, $R^9$=$CF_3$, "s"=1) and the cyclometallated ligands are derived from 7-hydroxy-1-phenylisoquinoline ($R^3$=OH, "m"=1, "n"=0). The composition of Entry 8c illustrates an organic iridium complex of the present invention wherein the ketopyrrole ligand comprises a methyl group and a divalent —O($CH_2$)O-radical ($R^2$=$CH_3$ "a"=1, $R^9$=—O($CH_2$)O—, "s"=1) and the cyclometallated ligands are derived from 7-dimethylamino-1-phenylisoquinoline ($R^3$=$NMe_2$, "m"=1, "n"=0). The composition of Entry 8d illustrates an organic iridium complex of the present invention wherein the ketopyrrole ligand comprises a nonyloxy group ("a"=0, $R^9$=$CH_3(CH_2)_8$—O—, "s"=1) and the cyclometallated ligands are derived from 1-phenylisoquinoline ("m"=0, "n"=0). The composition of Entry 8e illustrates an organic iridium complex of the present invention wherein the ketopyrrole ligand comprises two bromine groups ("a"=0, $R^9$=Br, "s"=2) at the 3- and 5-positions of the benzoyl moiety, and the cyclometallated ligands are derived from the 7-nonyloxy-1-phenylisoquinoline ($R^3$=$CH_3(CH_2)_8$—O—, "m"=1, "n"=0). Finally, the composition of Entry 8f illustrates an organic iridium complex of the present invention wherein the ketopyrrole ligand comprises two hydroxy groups ("a"=0, $R^9$=OH, "s"=2) at the 3- and 5-positions of the benzoyl moiety, and the cyclometallated ligands are derived from 7-nonyloxy-1-(3'-trifluoromethylphenyl)isoquinoline ($R^3$=$CH_3(CH_2)_8$—O—, "m"=1, $R^4$=$CF_3$, "n"=1).

TABLE 8

Exemplary Organic Iridium Complexes VII

| Entry | Ketopyrrole Ligand Structure | Cyclometallated Ligand Structure |
|---|---|---|
| 8a | | |
| 8b | | |
| 8c | | |

TABLE 8-continued

Exemplary Organic Iridium Complexes VII

| Entry | Ketopyrrole Ligand Structure | Cyclometallated Ligand Structure |
|---|---|---|
| 8d | $H_3C(CH_2)_8-O-$phenyl-C(=O)-pyrrole | 1-phenylisoquinoline |
| 8e | 3,5-dibromophenyl-C(=O)-pyrrole | 7-($H_3C(H_2C)_8O$)-1-phenylisoquinoline |
| 8f | 3,5-dihydroxyphenyl-C(=O)-pyrrole | 7-($H_3C(H_2C)_8O$)-1-(3-$F_3C$-phenyl)isoquinoline |

In one embodiment, the present invention provides an organic iridium complex having structure VIII.

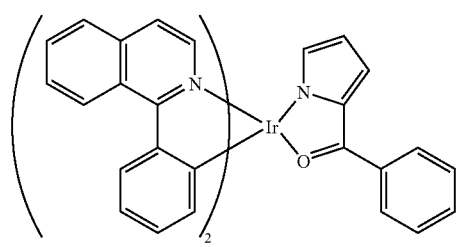

VIII

Exemplary organic iridium complexes of the present invention having structure VIII are provided in Table 9. The composition of Entry 9a illustrates an organic iridium complex of the present invention which is a racemic mixture comprising equal amounts of the two enantiomers shown, Enantiomer A, and Enantiomer B. Those skilled in the art will appreciate that Enantiomer A represents the mirror image of Enantiomer B, Enantiomer B represents the mirror image of Enantiomer A, and each enantiomer has $C_1$ symmetry. The composition of Entry 9b illustrates an organic iridium complex of the present invention which is a single enantiomer (Enantiomer A). The composition of Entry 9c illustrates an organic iridium complex of the present invention which is a single enantiomer (Enantiomer B) which is the mirror image of Enantiomer A. As noted, the present invention also provides organic iridium complexes which are not enantiomerically pure (i.e. do not consist of a single enantiomer) but which are enantiomerically enriched, for example an enantiomerically enriched organic iridium complex composition comprising 90 percent by weight Enantiomer A (Table 9) and 10 percent by weight Enantiomer B. (Table 9). The composition of Entry 9d illustrates an organic iridium complex of the present invention wherein one of the coordinating nitrogens of the cyclometallated ligand (those nitrogens marked †) are in a cis-relationship (as opposed to a trans-relationship featured in Enantiomers A and Enantiomer B) which is a racemic mixture. The non-tapered bold lines shown in the structure depicted in Entry 9d do not depict absolute stereochemistry.

TABLE 9

Exemplary Organic Iridium Complexes VIII

| Entry | Structure |
|---|---|
| 9a | 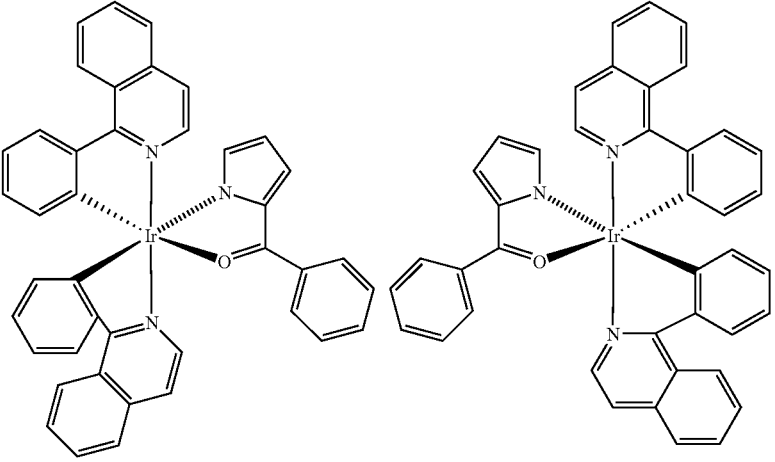<br>Enantiomer A      Enantiomer B |
| 9b | Single Enantiomer A |
| 9c | Single Enantiomer B |
| 9d | 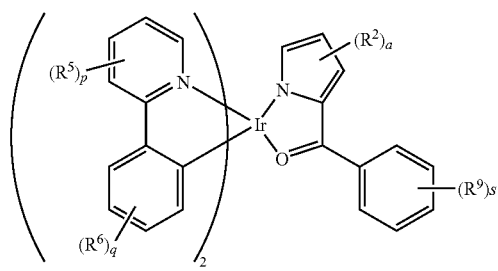<br>cis (racemic) |

In yet another embodiment, the present invention provides organic iridium complexes having structure IX

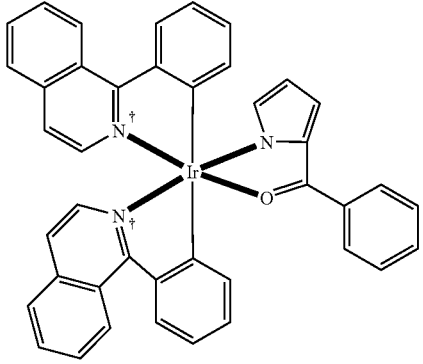

IX wherein $R^2$, $R^5$, $R^6$, and $R^9$ are independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3; "p" is an integer from 0 to 4; "q" is an integer from 0 to 4; and "s" is an integer from 0 to 5.

Exemplary organic iridium complexes having structure IX are provided in Table 10. The composition of Entry 10a illustrates an organic iridium complex of the present invention wherein the ketopyrrole ligand is unsubstituted ("a"=0, "s"=0) and the cyclometallated ligands are derived from 2-phenyl-5-trifluoromethylpyridine ($R^5$=$CF_3$, "p"=1, "q"=0). The composition of Entry 10b illustrates an organic iridium complex of the present invention wherein the ketopyrrole ligand comprises a 3,5-dihydroxybenzoyl moiety ("a"=0, $R^9$=OH, "s"=2) and the cyclometallated ligands are derived from 2-phenyl-5-trifluoromethylpyridine ($R^5$=$CF_3$, "p"=1, "q"=0). The composition of Entry 10c illustrates an organic iridium complex of the present invention wherein the ketopyrrole ligand comprises a methylacryloyloxy group and ("a"=0, $R^9$=methacryloyloxy, "s"=1) and the cyclometallated ligands are derived from 2-(3-dimethylaminophenyl)pyridine ("p"=0, R=$NMe_2$, "q"=1). The composition of Entry 10d illustrates an organic iridium complex of the present invention wherein the ketopyrrole ligand comprises a 1,1-dimethyl-1-butyl group and a chloroformate group ("a"=1, $R^2$=

$(CH_3)_2(CH_3CH_2CH_2)C—$, $R^9=ClCOO—$, "s"=1) and the cyclometallated ligands are unsubstituted ("p"=0, "q"=0). The composition of Entry 10e illustrates an organic iridium complex of the present invention wherein the ketopyrrole ligand comprises a 4-phenylbenzoyl moiety ("a"=0, $R^9$=phenyl, "s"=1).

TABLE 10

Exemplary Organic Iridium Complexes Having Structure IX

| Entry | Structure |
|---|---|
| 10a | [structure with CF₃ group on pyridine, phenyl on ketopyrrole] |
| 10b | [structure with CF₃ on pyridine, 3,5-dihydroxyphenyl on ketopyrrole] |
| 10c | [structure with dimethylamino on quinoline, methacrylate ester phenyl on ketopyrrole] |
| 10d | [structure with phenylpyridine, t-pentyl pyrrole, chloroformate phenyl ester] |

TABLE 10-continued

Exemplary Organic Iridium Complexes Having Structure IX

| Entry | Structure |
|---|---|
| 10e | [structure with phenylpyridine, 4-phenylbenzoyl ketopyrrole] |

In one embodiment, the present invention provides an organic iridium complex having structure X.

X

[structure X: bis(phenylpyridine)iridium with phenyl ketopyrrole ligand]

In yet another embodiment, the present invention provides organic iridium complexes having structure XI

XI

[structure XI showing isoquinoline with $(R^7)_d$ substituents, styryl group with $(R^8)_e$ substituents, pyrrole with $(R^2)_a$, phenyl with $(R^9)_b$]

wherein $R^2$, $R^7$, $R^8$, and $R^9$ are independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3; "d" is on integer from 0 to 6: "e" is an integer from 0 to 5; and "s" is an integer from 0 to 5.

Exemplary organic iridium complexes having structure XI are provided in Table 11. The composition of Entry 11a illustrates an organic iridium complex of the present invention wherein the ketopyrrole ligand is unsubstituted ("a"=0, "s"=0) and the cyclometallated ligands are derived from 1-(3', 5'-dibromostyryl)isoquinoline ("d"=0, $R^8$=Br, "e"=2). The composition of Entry 11b illustrates an organic iridium complex of the present invention wherein the cyclometallated ligands are derived from 1-(3',5'-dibromostyryl)-7-t-butyldimethylsilyloxyisoquinoline ($R^7$=t-butyldimethylsilyloxy, "d"=1, $R^8$=Br, "e"=2). The composition of Entry 11c illustrates an organic iridium complex of the present invention wherein the ketopyrrole ligand comprises a t-butyldimethylsilyloxybenzoyl moiety and ("a"=0, $R^9$=t-butyldimethylsilyloxy, "s"=1) and the cyclometallated ligands are derived from 1-styryl-7-t-butyldimethylsilyloxyisoquinoline ($R^7$=t-butyldimethylsilyloxy, "d"=1, "e"=0). The composition of Entry 11d illustrates an organic iridium complex of the present invention wherein the ketopyrrole ligand comprises a 4-n-hexanoyloxybenzoyl moiety ("a"=0, $R^9$=—OCO(CH$_2$)$_4$CH$_3$, "s"=1) and the cyclometallated ligands are derived from 1-styryl-7-bromoisoquinoline ($R^7$=Br, "d"=1, "e"=0). The composition of Entry 1e illustrates an organic iridium complex of the present invention wherein the ketopyrrole ligand comprises a 4-vinylbenzoyl moiety ("a"=0, $R^9$=vinyl, "s"=1) and the cyclometallated ligands are derived from 1-styrylisoquinoline ("d"=0, "e"=0).

TABLE 11

Exemplary Organic Iridium Complexes XI

| Entry | Structure |
| --- | --- |
| 11a | 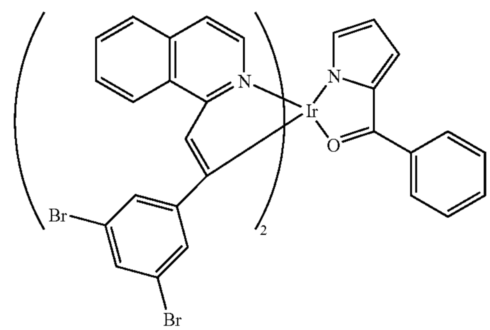 |
| 11b | 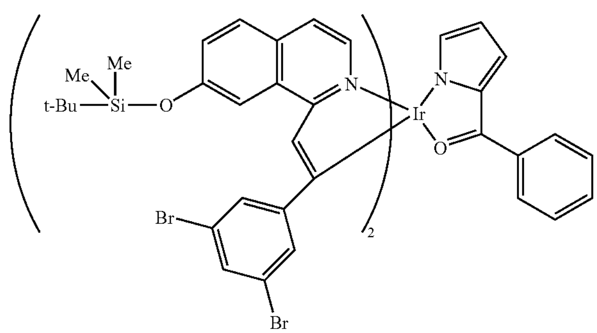 |
| 11c | 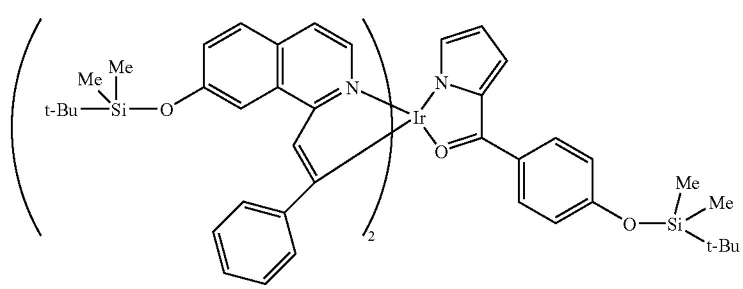 |
| 11d | 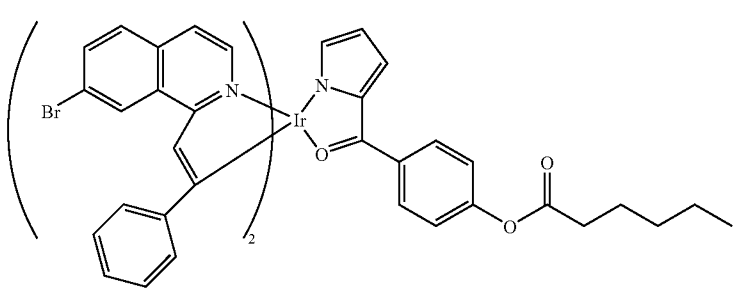 |

TABLE 11-continued

Exemplary Organic Iridium Complexes XI

| Entry | Structure |
|---|---|
| 11e | 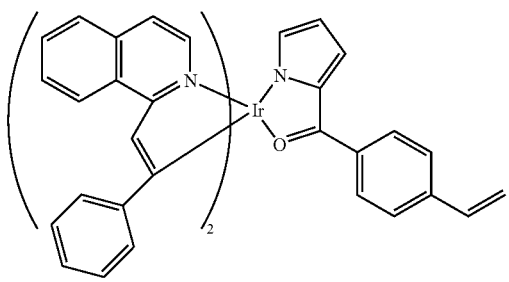 |

In one embodiment, the present invention provides an organic iridium complex having structure XII.

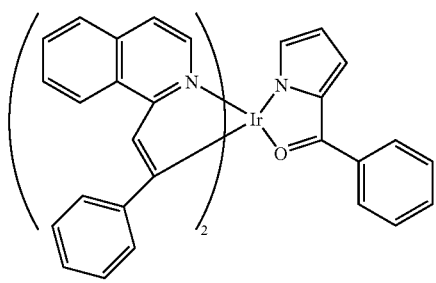

XII

In one embodiment, the present invention provides a composition comprising at least one organic iridium complex having structure XIII

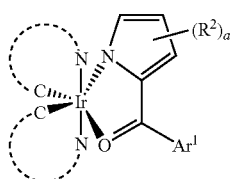

XIII wherein each of the ligands

is independently at each occurrence a cyclometallated ligand which may be the some or different;

$Ar^1$ is a $C_3$-$C_{50}$ aromatic radical;

$R^2$ is independently at each occurrence a deuterium atom, a halogen, a nitro group, on amino group, a $C_4$-$C_{40}$ aromatic radical, a $C_1$-$C_{50}$ aliphatic radical, or a $C_3$-$C_{40}$ cycloaliphatic radical;

"a" is an integer from 0 to 3.

Those skilled in the art will appreciate that structure XIII represents a subgenus of structure I wherein the group $R^1$ is a $C_3$-$C_{40}$ aromatic radical. Exemplary organic iridium complexes having structure XIII are provided in Table 12.

The exemplary organic iridium complexes 12a-12e in Table 12 illustrate instances in which the ketopyrrole ligand, may be derived from an aroyl pyrrole (See Entry 12a, derived from 2-(2-thienylcarbonyl)pyrrole (CAS No. 13169-77-2). The exemplary organic iridium complexes 12a-12e in Table 12 further illustrate instances in which the cyclometallated ligands are identical. For example, in Entry 12a each of the cyclometallated ligands is derived from 1-(3'-methoxyphenyl)isoquinoline. The exemplary organic iridium complex of Entry 12b comprises a ketopyrrole ligand derived from 2-(2, 5-dimethyl-3-thienylcarbonyl)pyrrole wherein $Ar^1$ is a $C_6$ aromatic radical. The iridium complex of Entry 12d comprises a ketopyrrole ligand which may be derived from 2-(3, 5-dimethacroyloxybenzoyl)pyrrole wherein $Ar^1$ is a $C_{14}$ aromatic radical. The organic iridium complex of Entry 12e comprises a ketopyrrole ligand which may be derived from 2-(1-azulenylcarbonyl)pyrrole wherein $Ar^1$ is a $C_{10}$ aromatic radical. Synthetic methodologies useful for the preparation of the ketopyrrole precursors which may be used to prepare the organic iridium complexes 12a-12e are known to those skilled in the art. Similarly, synthetic methodologies useful for the preparation of the cyclometallated ligand precursors which may be used to prepare organic iridium complexes 12a-12e are likewise known to those skilled in the art.

TABLE 12

Exemplary Organic Iridium Complexes Having Structure XIII

| Entry | Ketopyrrole Ligand Structure | Cyclometallated Ligand Structure |
|---|---|---|
| 12a | | |
| 12b | | |
| 12c | | |
| 12d | | |
| 12e | | |

In one embodiment, the present invention provides an organic iridium complex having structure XIV.

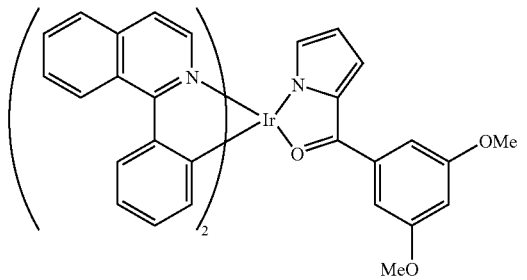

XIV

As illustrated in the case of organic iridium complexes VII, the organic iridium compositions provided by the present invention may, in various embodiments, be a single enantiomer, a racemic mixture, a mixture of diastereomers, or an enantiomerically enriched composition. Thus in one embodiment, the present invention provides organic iridium complex XIV as an enantiomerically enriched composition.

In one aspect the present invention provides organic iridium compositions which are deuterated. A compound is deuterated when it comprises deuterium in an amount which exceeds the natural abundance level of deuterium ordinarily anticipated. For example, the natural abundance level of deuterium in an organic iridium complex such as compound VIII would be such that about 0.015% of the sites in compound VIII nominally occupied by hydrogen would in fact be occupied by deuterium. (Compound VIII comprises 28 sites nominally occupied by hydrogen, the default substituent.) Deuterated organic iridium complexes may be prepared from deuterated cyclometallated ligand precursors and/or deuterated ketopyrrole ligand precursors. In certain embodiments, deuterated organic iridium complexes display enhanced quantum efficiencies relative to the corresponding material containing deuterium at natural abundance deuterium levels (i.e. about 0.015%).

Thus, in one embodiment, the present invention provides a deuterated organic iridium complex comprising at least one cyclometallated ligand and at least one ketopyrrole ligand. In one embodiment, the organic iridium complex is at least 10 percent deuterated. In another embodiment, the organic iridium complex is at least 40 percent deuterated. In an alternate embodiment, the organic iridium complex is at least 60 percent deuterated. In yet another embodiment, the organic iridium complex is at least 80 percent deuterated.

In a further embodiment, the present invention provides an electrophosphorescent composition comprising at least one electroactive host material and at least one organic iridium complex. An electrophosphorescent composition is a composition which emits light by radiative decay of a triplet excited state formed as a result of the application of a voltage bias. In one embodiment, the present invention provides an electrophosphorescent composition which when subjected to a voltage bias, emits light primarily from a triplet excited state of an organic iridium complex formed by energy transfer from the host material to the organic iridium complex. The organic iridium complexes provided by the present invention are well suited for use in electrophosphorescent compositions because energy transfer from the excited state of the host material to the organic iridium complex is in many instances exceedingly efficient. Suitable electroactive host materials include electroluminescent materials and otherwise electroactive materials. Suitable non-polymeric host materials are exemplified in Table 13 together with their Chemical Abstracts Registry Number (CAS No.).

TABLE 13

Exemplary Non-Polymeric Host Materials

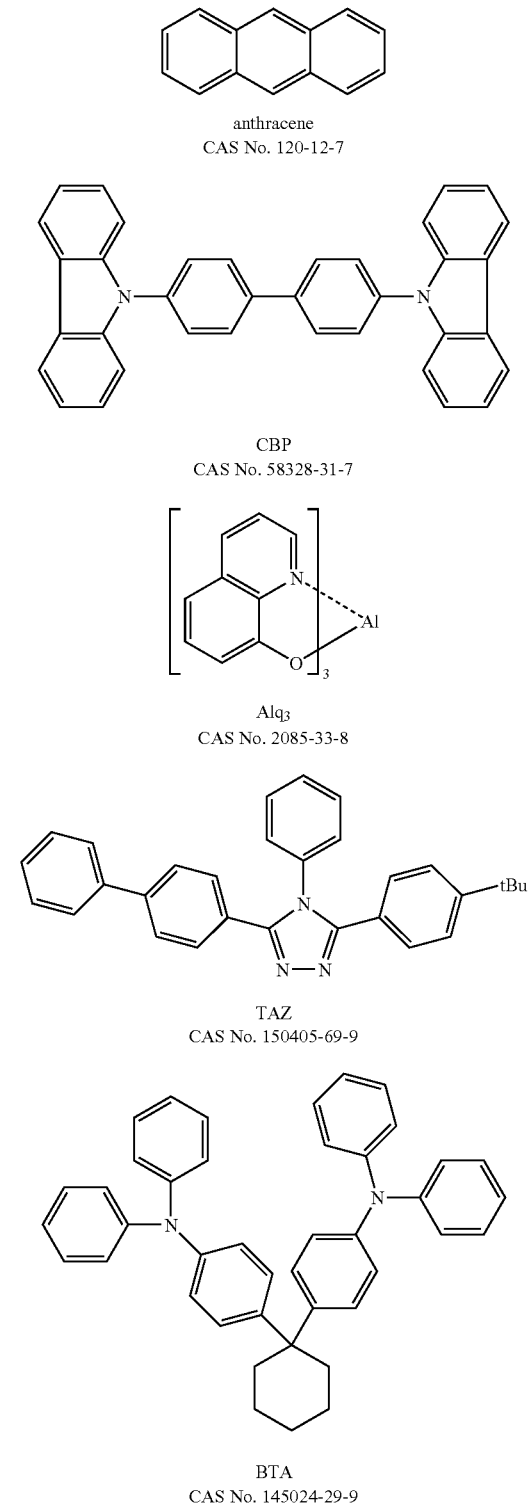

TABLE 13-continued

Exemplary Non-Polymeric Host Materials

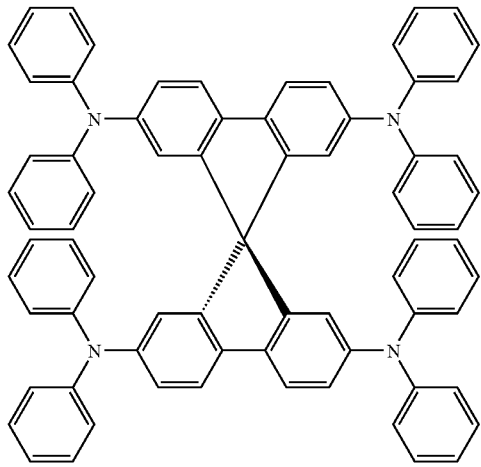

Spiro-TAD
CAS No. 189363-47-1

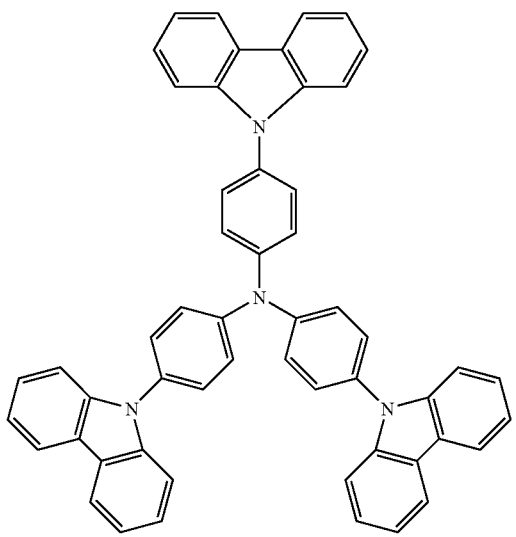

TCTA
CAS No. 139092-78-7

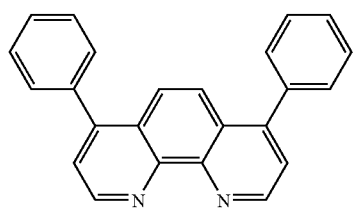

Bphen
CAS No. 1662-01-7

In an alternate embodiment, the host material is an electroactive polymeric material. Suitable electroactive polymeric materials include polyvinylcarbazole (PVK), polyphenylenevinylene (PPV), phenyl-substituted polyphenylenevinylene (PhPPV), poly(9,9-dioctyl fluorene), and the like.

Thus, in one embodiment, the present invention provides an electrophosphorescent composition comprising at least one electroactive host material and at least one organic iridium complex having structure I. In an alternate embodiment, the present invention provides an electrophosphorescent composition comprising at least one electroactive host material and at least one organic iridium complex having structure VII. In yet another embodiment, the present invention provides an electrophosphorescent composition comprising at least one electroactive host material and at least one organic iridium complex having structure IX. In yet still another embodiment, the present invention provides an electrophosphorescent composition comprising at least one electroactive host material and at least one organic iridium complex having structure XI.

In one embodiment, the electrophosphorescent composition comprises a host material which is a blue light emitting electroluminescent organic material, for example, poly(9,9-dioctyl fluorene).

In one embodiment, the organic iridium complex is characterized by a lowest accessible triplet state energy T1 and the electroactive host material is characterized by a lowest accessible triplet state energy T2. As will be appreciated by those skilled in the art, energy transfer from the electroactive host material to the organic iridium complex can be especially favorable under circumstances wherein T1 is less than T2. Thus, in one embodiment, the electrophosphorescent composition comprises a blue light emitting electroluminescent material and an organic iridium complex, wherein the organic iridium complex is characterized by a lowest accessible triplet state energy T1 and the blue light emitting electroluminescent organic material is characterized by a lowest accessible triplet state energy T2, and wherein T1 is less than T2.

In one embodiment, the present invention provides an electrophosphorescent composition comprising an electroactive host material and an organic iridium complex comprising at least one cyclometallated ligand and at least one ketopyrrole ligand, wherein the organic iridium complex is present in an amount corresponding to from about 0.01 percent to about 50 percent by weight of the entire weight of the electrophosphorescent composition. In another embodiment, the organic iridium complex is present in an amount corresponding to from about 0.1 percent to about 10 percent by weight of the entire weight of the electrophosphorescent composition. In yet another embodiment another embodiment, the organic iridium complex is present in an amount corresponding to from about 0.5 percent to about 5 percent by weight of the entire weight of the electrophosphorescent composition.

Exemplary electrophosphorescent compositions comprising at least one electroactive host material and at least one organic iridium complex are given in Table 14. For example, the composition of Entry 14a is an electrophosphorescent composition suitable for use in an electronic device such as an OLED, said electrophosphorescent composition containing 4 percent by weight organic iridium complex VIII and 96% by weight of carbazole derivative TCTA. The composition of Entry 14d is an electrophosphorescent composition suitable for use in an electronic device, said electrophosphorescent composition containing 5 percent by weight organic iridium complex XIV, 40 percent by weight of triazole derivative TAZ, 40 percent by weight of dicarbazole derivative CBP, and 15 percent by weight of bis(triarylamine) BTA.

TABLE 14

Electroactive Host-Organic iridium complex Compositions

| Entry | Organic iridium complex (wt %*) | Host Material (wt %*) | Component 3 (wt %*) | Component 4 (wt %*) |
|---|---|---|---|---|
| 14a | VIII (4%) | TCTA (96%) | — (0%) | — (0%) |
| 14b | X (5%) | BTA (95%) | — (0%) | — (0%) |
| 14c | XIV (50%) | Alq$_3$ (50%) | — (0%) | — (0%) |
| 14d | XIV (5%) | TAZ (40%) | CBP (40%) | BTA (15%) |
| 14e | XII (10%) | CBP (90%) | — (0%) | — (0%) |
| 14f | XII (5%) | Anthracene (80%) | Bphen (15%) | — (0%) |

*"Wt %" refers to the weight percentage of a component relative to the entire weight of the electroactive host-organic iridium complex composition as a whole.

In one embodiment, the present invention provides a polymer composition comprising (1) a polymeric component, and (2) at least one organic iridium complex, the at least one organic iridium complex comprising at least one cyclometallated ligand and at least one ketopyrrole ligand. The polymeric component comprises at least one polymeric material having a number average molecular weight ($M_n$) greater than 2,000 grams per mole as determined by gel permeation chromatography. The polymeric component is not an organic iridium complex having an overall number average molecular weight greater than 2,000 grams per mole. Nor is the polymeric component a polymeric organic iridium complex comprising at least one ligand having a number average molecular weight of greater than 2,000 grams per mole. Those skilled in the art will appreciate that number average molecular weight of polymeric materials may also be determined by other techniques such as $^1$H-NMR spectroscopy. In one embodiment, the polymeric component comprises at least one polymeric material having a number average molecular weight ($M_n$) greater than about 5,000 grams per mole as determined by gel permeation chromatography. In another embodiment, the polymeric component comprises at least one polymeric material having a number average molecular weight ($M_n$) greater than about 15,000 grams per mole as determined by gel permeation chromatography. In yet another embodiment, the polymeric component comprises at least one polymeric material having a number average molecular weight ($M_n$) greater than about 25,000 grams per mole as determined by gel permeation chromatography.

The polymeric component may be, for example, a bisphenol A polycarbonate, a polymer blend comprising a bisphenol A polycarbonate, a bisphenol A copolycarbonate, a blend comprising a bisphenol A copolycarbonate, or like polymeric materials. Other suitable polymers include vinyl polymers such as polyvinyl chloride, polystyrene, poly(methyl methacrylate), poly(methyl acrylate), polymerized polyacrylates such as Sartomer 454, and the like; acetal polymers; polyesters such as poly(ethylene terephthalate); polyamides such as nylon 6; polyimides; polyetherimides such as ULTEM; polyethertherketones; polysulfones; polyethersulfones such as RADEL and UDEL, and the like. The polymeric component may be homopolymer, a random copolymer, a block copolymer, a terpolymer, a graft-copolymer, an alternating copolymer, or like polymeric material. Polymeric blends useful as the polymeric component may be prepared using standard techniques known in the art, for example extrusion blending.

In one embodiment, the polymeric component comprises an electroactive polymer. Electroactive polymers are polymers which are susceptible to charge conduction when subjected to a voltage bias, for example polymeric materials which conduct electrons and or holes in an organic light emitting device (OLED). Electroactive polymers include, for example, organic semiconducting polymers. Those skilled in the art will appreciate that while electroluminescent polymers represent a class of electroactive polymers, a material need not be electroluminescent to be electroactive. Electroactive polymers generally possess a delocalized π-electron system, which typically enables the polymer chains to support positive charge carriers (holes) and negative charge carriers (electrons) with relatively high mobility. Suitable electroactive polymers are illustrated by poly(n-vinylcarbazole) ("PVK", emitting violet-to-blue light in a wavelength range of from about 380 to about 500 nanometers) and poly(n-vinylcarbazole) derivatives; polyfluorene and polyfluorene derivatives such as poly(dialkyl fluorene), for example poly(9,9-dihexyl fluorene) (emitting light in a wavelength range of from about 410 to about 550 nanometers), poly(dioctyl fluorene) (wavelength at peak electroluminescent (EL) emission of about 436 nanometers), and poly{9,9-bis(3,6-dioxaheptyl)-fluorene-2,7-diyl} (emitting light in a wavelength range of from about 410 to about 550 nanometers); poly(paraphenylene) ("PPP") and its derivatives such as poly(2-decyloxy-1,4-phenylene) (emitting light in a wavelength range of from about 400 to about 550 nanometers) and poly(2,5-diheptyl-1,4-phenylene); poly(p-phenylene vinylene) ("PPV") and its derivatives such as dialkoxy-substituted PPV and cyano-substituted PPV; polythiophene and its derivatives such as poly(3-alkylthiophene), poly(4,4'-dialkyl-2,2'-bithiophene), and poly(2,5-thienylene vinylene); poly(pyridine vinylene) and its derivatives; polyquinoxaline and its derivatives; and polyquinoline and its derivatives. Mixtures of these polymers and/or copolymers comprising structural units common to two or more of the aforementioned polymers may be used as the polymeric component.

Additionally, polysilanes may in some circumstances be suitable electroactive polymers which may serve as the polymeric component in various aspects of the present invention. Typically, polysilanes are linear silicon-backbone polymers substituted with a variety of alkyl and/or aryl groups. Polysilanes are quasi one-dimensional materials with delocalized sigma-conjugated electrons along polymer backbone. Examples of suitable polysilanes include, but are not limited to, poly(di-n-butylsilane), poly(di-n-pentylsilane), poly(di-n-hexylsilane), poly(methylphenylsilane), and poly{bis(p-butylphenyl)silane}. The polysilanes generally emit light in a wavelength in a range from about 320 nanometers to about 420 nanometers.

In one embodiment, the present invention provides a polymer composition comprising a poly(dialkyl fluorene) polymeric component and an organic iridium complex comprising at least one cyclometallated ligand and at least one ketopyrrole ligand.

Thus, in one aspect, the present invention provides a polymer composition which is a light emitting polymer composition, said light emitting polymer composition comprising an electroluminescent polymer and at least one organic iridium complex, said organic iridium complex comprising at least one cyclometallated ligand and at least one ketopyrrole ligand. In one embodiment, the light emitting polymer composition comprises an electroluminescent polymer selected from the group consisting of poly(n-vinylcarbazole) (PVK), poly(n-vinylcarbazole) derivatives, poly(dialkyl fluorene), poly(9,9-dihexyl fluorene), poly(9,9-dioctyl fluorene), poly{9,9-bis(3,6-dioxaheptyl)-fluorene-2,7-diyl}, poly(paraphenylene) ("PPP"), poly(2-decyloxy-1,4-phenylene), poly(2,5-diheptyl-1,4-phenylene), poly(p-phenylene vinylene) ("PPV"), and mixtures thereof.

As noted, in one aspect the present invention provides a polymer composition comprising a polymeric component and an organic iridium complex. The organic iridium complex can be any one of the various organic iridium complexes of the present invention comprising at least one cyclometallated ligand and at least one ketopyrrole ligand. In addition, the polymer composition provided by the present invention may comprise more than one organic iridium complex. In one embodiment, the polymer composition provided by the present invention comprises at least two different organic iridium complexes. In an alternate embodiment, the present invention provides a polymer composition comprising a plurality of organic iridium complexes.

As noted, the organic iridium complex can be any one of the various cyclometallated iridium complexes discussed herein comprising at least one cyclometallated ligand and at least one ketopyrrole ligand. For example, in one embodiment, the present invention provides a polymer composition comprising a polymeric component and an organic iridium complex having structure I, and in another embodiment the present invention provides a polymer composition comprising a polymeric component and an organic iridium complex wherein the cyclometallated ligand is derived from a phenylisoquinoline having structure II. In another embodiment, at least one component of the polymer composition is deuterated. In one embodiment, the organic iridium complex is deuterated. In an alternate embodiment, the polymeric component is deuterated.

In one aspect, the present invention provides a polymer composition comprising an electroluminescent polymer and an organic iridium complex said organic iridium complex comprising at least one cyclometallated ligand and at least one ketopyrrole ligand, wherein the organic iridium complex is characterized by a lowest accessible triplet state energy T1, and the electroluminescent polymer is characterized by a lowest accessible triplet state energy T2, and wherein T1 is less than T2. As noted earlier, energy transfer from the electroluminescent polymer to the organic iridium complex can be especially favorable under circumstances wherein T1 is less than T2. In one embodiment, the electroluminescent polymer is a blue light emitting electroluminescent polymer characterized by a lowest accessible triplet state energy T2, wherein T2 is greater than the lowest accessible triplet state energy, T1, of the organic iridium complex.

Polymer compositions comprising a polymeric component and at least one organic iridium complex can be prepared using conventional melt blending techniques, such as dispersing the organic iridium complex into a polymer melt. Alternately, the polymer composition may be prepared by mixing a solution of the polymer with a solution of the organic iridium complex and evaporating the solvent to prepare, for example, the polymer composition in the form of a film. In yet another embodiment, the polymer composition may be prepared by dispersing the organic iridium complex in a monomer such as a mixture of methyl methacrylate and Sartomer 454 and subsequently polymerizing the monomer mixture in the presence of the organic iridium complex. The Examples section of this disclosure provides additional guidance on the preparation of polymer compositions provided by the present invention.

Exemplary compositions comprising a polymeric component and an organic iridium complex comprising at least one cyclometallated ligand and at least one ketopyrrole ligand are given in Table 15. The composition of Entry 15a is a polymer composition comprising a bisphenol A polycarbonate and organic iridium complex VIII in an amount corresponding to 3 weight percent of the total weight of the polymer composition. The polymer composition of Entry 15b comprises polystyrene and organic iridium complex VIII in an amount corresponding to 5 weight percent of the total weight of the polymer composition. The compositions of Entries 15e and 15f comprise respectively poly(n-vinylcarbazole) and ODX-7 (CAS No. 138372-67-5) and poly(N-vinylcarbazole) and PBD (CAS No. 15082-28-7) respectively. The composition of Entry 15g comprises poly(9,9-dioctyl fluorene) as an electroactive polymeric component, and organic iridium complex XII.

TABLE 15

Exemplary Polymer Compositions Of The Invention

| Entry | Organic iridium complex (wt %*) | Polymeric Component Polymer Type (wt %*) | $M_n$ |
|---|---|---|---|
| 15a | VIII (3%) | Bisphenol A polycarbonate (97%) | 12,000 |
| 15b | VIII (5%) | polystyrene (95%) | 225,000 |
| 15c | VIII (5%) | PMMA (95%) | 15,000 |
| 15d | XIV (5%) | poly(ethylene terephthalate) (95%) | 22,500 |
| 15e | XII (3%) | poly(n-vinylcarbazole) (90%), ODX-7 (7%) | 17,000 |
| 15f | XII (3%) | poly(n-vinylcarbazole) (90%), PBD (7%) | 17,000 |
| 15g | XII (5%) | poly(9,9-dioctyl fluorene) (98%) | 8,500 |

*Weight percentage based on the total weight of the composition

In another aspect, the present invention provides a composition comprising a polymeric organic iridium complex, said polymeric organic iridium complex comprising at least one cyclometallated ligand and at least one ketopyrrole ligand, wherein at least one of said cyclometallated ligand or said ketopyrrole ligand is a polymeric ligand. As noted, an organic iridium composition of the present invention is a polymeric organic iridium complex when it comprises at least one cyclometallated ligand and at least one ketopyrrole ligand wherein at least one ligand of the composition has a number average molecular weight of at least 2,000 grams per mole as measured by gel permeation chromatography. Those skilled in the art will understand that the molecular weight of the ligand can be determined prior to formation of the organic iridium complex, for example by analysis of the ligand precursor by gel permeation chromatography. Alternatively, the molecular weight of may be determined indirectly by analysis of the polymeric organic iridium complex itself by gel permeation chromatography. In one embodiment, the cyclometallated ligand is derived from a 1-phenylisoquinoline, a 2-phenylpyridine, a 1-styryl isoquinoline, or a combination thereof.

Any of the ligands of the ligands present in the polymeric organic iridium complex may be deuterated. In one embodiment, all of the ligands of the polymeric organic iridium complex are deuterated. In one embodiment, at least one of the cyclometallated ligand and ketopyrrole ligand is at least 10 percent deuterated. In another embodiment, at least one of the cyclometallated ligand and ketopyrrole ligand is at least 50 percent deuterated.

In one embodiment, polymeric organic iridium complex comprises a polymeric ligand derived from a polymeric cyclometallated ligand precursor, for example a polymeric 1-phenylisoquinoline. In another embodiment, the polymeric organic iridium complex comprises a polymeric ligand derived from a polymeric ketopyrrole ligand precursor (e.g. a polymeric ketopyrrole). In one embodiment, the polymeric organic iridium complex comprises at least two polymeric ligands. In one embodiment, the present invention provides a polymeric organic iridium complex comprising a polymeric cyclometallated ligand derived from a cyclometallated ligand precursor selected from the group consisting of a polymeric 1-phenylisoquinoline, a polymeric 1-styrylisoquinoline, a polymeric 2-phenylpyridine, and a combination thereof.

In another embodiment, the polymeric organic iridium complex is prepared from a non-polymeric organic iridium complex of the present invention. It is stressed that the terms "organic iridium complex" and "non-polymeric organic iridium complex" are interchangeable terms, have the same meaning, and are distinct from the polymeric organic iridium complexes of the present invention. In one embodiment, a non-polymeric organic iridium complex comprises one or more reactive functional groups which are used to incorporate the non-polymeric organic iridium complex into a polymer chain in a polymerization step. For example, treatment of the non-polymeric organic iridium complex shown in Entry 8f of Table 8 with bisphenol A and phosgene under interfacial polycarbonate polymerization conditions (i.e. in a mixture comprising water, methylene chloride, a stoichiometric amount of sodium hydroxide, and a catalytic amount of hexaethylguanidinium chloride phase transfer catalyst) affords a copolycarbonate comprising structural units derived from bisphenol A and structural units derived from the non-polymeric organic iridium complex, the two hydroxy groups of the ketopyrrole ligand present in the composition of Entry 8f (Table 8) serving as points of attachment to the polymer chain. As those skilled in the art will appreciate, under such circumstances, it is possible for a single polymer chain to comprise multiple iridium complexes arrayed along the polymer backbone. In instances where the non-polymeric organic iridium complex comprises but a single functional group susceptible to reaction under polymerization conditions, the non-polymeric organic iridium complex may serve as an organometallic endcapping agent, providing a polymeric species incorporating organic iridium complexes at the polymer chain ends. In one embodiment, the non-polymeric organic iridium complex used to prepare the polymeric organic iridium complex is enantiomerically enriched. Further examples of polymeric organic iridium complexes provided by the present invention are provided in the Examples section of this disclosure.

As noted, in one embodiment, the polymeric organic iridium complex incorporates a polymeric ligand having a number average molecular weight ($M_n$) of at least 2,000 grams per mole as determined by gel permeation chromatography. In another embodiment, the polymeric organic iridium complex incorporates a polymeric ligand having a $M_n$ of at least 5,000 grams per mole as determined by gel permeation chromatography. In yet another embodiment, the polymeric organic iridium complex incorporates a polymeric ligand having a $M_n$ of at least 10,000 grams per mole as determined by gel permeation chromatography.

From the preceding discussion it will be apparent that in one aspect, the polymeric organic iridium complexes of the present invention comprise one or more polymer chains incorporating a polymeric ligand. A wide variety of polymer types may comprise the polymer chains. Suitable polymer types may include homopolymers, alternating copolymers, block copolymers, terpolymers, graft copolymers, star-burst polymers, condensation polymers, addition polymers, branched polymers, crosslinked polymers, thermoplastic polymers, thermosetting polymers, and the like. Exemplary polymer types which may comprise the polymer chain include, but are not limited to, conjugated polymers, olefin polymers, polycarbonates, ABS, EVA, HDPE, nylon, PET, PEN, and the like. In one embodiment, the polymeric ligand is selected from the group consisting of polycarbonates, polyarylates, polyacrylates, and polyamides. In another embodiment, the polymeric ligand is an electroactive polymer. In yet another embodiment, polymeric ligand comprises an electroluminescent polymer. In certain embodiments, the polymeric organic iridium complex comprises at least one ligand which is electroluminescent, for example a ligand which is a polyfluorene. Those skilled in the art will understand that the polymeric ligand must comprise appropriate functionality to bind to the iridium ion present in the polymeric organic iridium complex. Thus, it will be understood that a ligand which is, for example, a polyfluorene will be bound to the iridium ion either by a cyclometallated ligand moiety or a ketopyrrolic ligand moiety.

In one embodiment, the polymeric organic iridium complex has structure XV

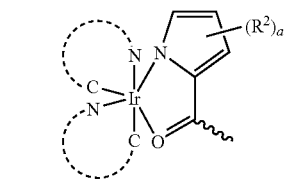

XV wherein each of the ligands

is independently at each occurrence a cyclometallated ligand which may be the some or different;

$R^2$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical; and "a" is an integer from 0 to 3;

and wherein the substructure is a polymer chain.

Exemplary polymeric organic iridium complexes of the present invention are given in Table 16. Each of Entries 16a-16e represents a chemical species encompassed by generic formula XV and each of these compositions comprises a polymer chain terminated at each chain end by an organic iridium complex. Each of the compositions Entries 16a-16e may be derived from a non-polymeric organic iridium complex XVI via Suzuki coupling in which the non-polymeric organic iridium complex acts as a endcapping agent in the polymerization. The composition of Entry 16a, for example, comprises a poly(9,9-dioctyl fluorene)polymer chain having a number average molecular weight of about 8,000 grams per mole, said polymer chain being terminated at each end by a benzoylpyrrole ligand bound to an iridium ion, the iridium ion being bound to two "ppy" ligands. Thus, the composition of Entry 16a contains two benzoylpyrrole ligands, two iridium ions, and four "ppy" ligands. It should be noted that the composition of Entry 16a (and also those of Entries 16b-16e) is a species encompassed by generic structure XV wherein the polymer chain ~~of structure XV, itself comprises an organic iridium complex. For convenience of representation, this second organic iridium complex is not shown, but it will be understood to be part of the polymer chain ~~of structure XV when this structure is used to represent the composition of Entry 16a (or 16b-16e). The composition of Entry 16a can be prepared by copolymerizing, via Suzuki coupling, organic iridium complex XVI, wherein the cyclometallated ligands are each derived from 2-phenylpyridine (i.e. "ppy" ligands), with a mixture of 2,7-dibromo-9,9-dioctylfluorene and 9,9-dioctylflouren-2,7-diyl-bistrimethyleneborate. The composition of Entry 16b comprises four fully deuterated cyclometallated ($D_8$)ppy ligands derived from perdeutero-2-phenylpyridine ($C_{11}D_9N$) and may be prepared analogously to Entry 16a via Suzuki coupling. The polymeric organic iridium complexes of Entries 16c and 16d are similarly prepared from the non-polymeric organic iridium complex XVI wherein the cyclometallated ligands are derived from 1-phenylisoquinoline and hexadeutero 1-phenylisoquinoline ("($D_6$)piq") respectively. The polymer chain structure shown for the composition of Entry 16c is designated "F8-TFB copolymer". ($D_6$)piq refers to a partially deuterated "piq" ligand and is derived from 1-phenylisoquinoline comprising a perdeutero-isoquinoline ring ($C_{15}D_6H_5N$). ($D_{10}$)piq refers to a fully deuterated "piq" ligand and is derived from perdeutero 1-phenylisoquinoline ($C_{15}D_{11}N$). The composition of Entry 16e is prepared analogously to the composition of Entry 16a.

Thus, in one embodiment, polymeric organic iridium complexes such as XV are derived from a non-polymeric organic iridium complex having a single functional group that is reacted with a corresponding reactive group on a unit that is part of a polymer, an oligomer, or a monomer susceptible to polymerization. In some embodiments, the organic iridium complex represents a pendant group, rather than a terminal group, on a polymer chain. For example, copolymerization of styrene with an organic iridium complex having structure XVII will produce an olefin copolymer comprising pendant organic iridium complexes and phenyl rings as substructures arrayed along a polyethylene chain. Exemplary non-polymeric organic iridium complexes from which polymeric organic iridium complexes having structure XV may be derived include compounds having structures XVI-XVIII

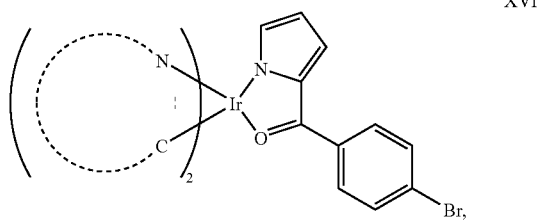

XVI

TABLE 16

Exemplary Polymeric Organic Iridium Complexes XV Comprising Terminal Organic Iridium Complexes

| Entry | C͡N | $R^2$ | "a" | Polymer Chain | $Mn^†$ |
|---|---|---|---|---|---|
| 16a | ppy | — | 0 | poly(9,9-dioctyl fluorene) | 8,000 |
| 16b | ($D_8$)ppy | — | 0 | poly(9,9-dioctyl fluorene) | 15,000 |
| 16c | piq | — | 0 | F8-TFB copolymer | 7,000 |
| 16d | ($D_6$)piq | — | 0 | F8-TFB copolymer | 10,000 |
| 16e | ($D_{10}$)piq | — | 0 | poly(9,9-dioctyl fluorene) | 5,000 |

†number average molecular weight of the polymer chain ~~

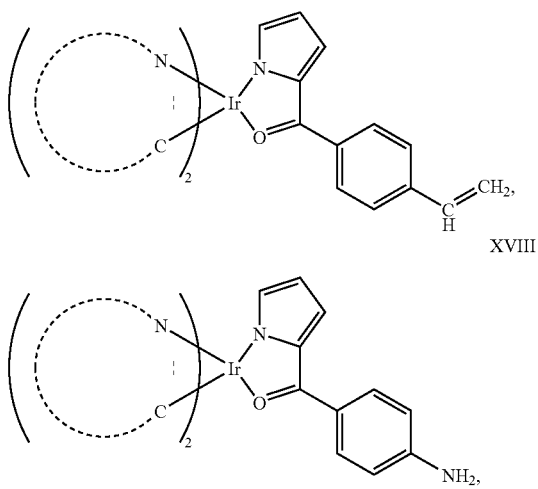

and combinations thereof.

Further exemplary polymeric organic iridium complexes of the present invention encompassed by structure XV are given in Table 17. Each of the polymeric organic iridium complex compositions illustrated in Table 17 (Entries 17a-17c) represents a species encompassed by generic formula XV comprising structural units derived from non-polymeric organic iridium complex XVII arrayed along a polymer chain. Those skilled in the art will appreciate that generic structure XV does not impose a condition that the structural unit comprising an iridium center be attached at the end of polymer chain. Structure XV merely indicates that the structural unit comprising an iridium center forms some part of a polymer chain. Thus, generic structure XV encompasses polymeric organic iridium complexes such as the compositions of Entries 17a-17c in which the structural units comprising an iridium center are arrayed along the length of a polymer chain. Also generic structure XV encompasses polymeric organic iridium complexes comprising structural units comprising an iridium center which are present only at the polymer chain ends. From this discussion it will be understood by those skilled in the art that the polymeric organic iridium complex may comprise multiple structural units comprising an iridium center.

TABLE 17

Polymeric Organic Iridium Complexes XV Comprising Pendant Organic Iridium Complexes

| Entry | C︵N | $R^2$ | "a" | Polymer Chain | $M_n^\dagger$ |
|---|---|---|---|---|---|
| 17a | ppy | 0 | — | Copolymer prepared by polymerization of a mixture comprising 4 mole percent vinyl monomer XVII and 96 mole percent styrene | 35,000 |
| 17b | ppy | 0 | — | Copolymer prepared by polymerization of a mixture comprising 3 mole percent vinyl monomer XVII and 97 mole percent N-vinylcarbazole | 9,000 |
| 17c | piq | 0 | — | Copolymer prepared by polymerization of a mixture comprising 5 mole percent vinyl monomer XVII and 94 mole percent N-vinylcarbazole and 2 mole percent divinylbenzene | 27,000 |

$M_n^\dagger$ is the number average molecular weight (GPC) of the polymer chain inclusive of the molecular weight contributions of pendant organic iridium complex subunits.

Those skilled in the art will appreciate that the functional groups shown in structure XVI (aryl bromide), structure XVII (vinyl), and structure XVIII (amino) may be reacted with functional groups having a complimentary reactivity to form polymeric species. Groups having complementary reactivity to the aryl bromide group include, for example, boronic acid groups under Suzuki coupling conditions. Groups having complementary reactivity to the vinyl group of structure XVII include, for example, vinyl monomers such as styrene, acrylonitrile, methyl methacrylate, methyl acrylate, polyacrylates such as Sartomer 454, and the like under olefin polymerization conditions. Groups having complementary reactivity to the amino group of structure XVIII include the anhydride groups of an anhydride-terminated polymeric species, for example an anhydride-terminated polyetherimide having a number average molecular weight of about 10,000 grams per mole as determined by gel permeation chromatography, prepared by reaction of a molar excess of bisphenol A dianhydride (BPADA) with meta-phenylene diamine. Those skilled in the art will appreciate that many additional conventional functional groups are available for use in the preparation of polymeric organic iridium complexes from organic iridium complexes analogous to compounds XVI-XVIII.

Conventional polymerization conditions may be used to provide many of the polymeric organic iridium complexes of the present invention. For example, in one embodiment, an organic iridium complex comprising a amine group (e.g. monomeric organic iridium complex XVIII wherein the two cyclometallated ligands are derived from 2-phenylpyridine) may be added as a co-reactant to a reaction mixture comprising toluene diisocyanate and N,N'-dimethyl hexamethylenediamine in toluene to form a polyurea comprising chain terminal structural units derived from the iridium complex XVIII.

In certain embodiments, the polymeric organic iridium complex may be prepared from a multifunctional organic iridium complex selected from the group consisting of organic iridium complexes XIX, XX, XXI, and a combination thereof. Organic iridium complexes susceptible to incorporation into polymer structural units other than the end groups of the polymer (e.g. polymer repeat units) are at times herein referred to as monomeric organic iridium complexes. For example, organic iridium complex XVII may be employed as a vinyl monomer in a copolymerization reaction with styrene wherein the product copolymer comprises repeat units derived from styrene and repeat units derived from the organic iridium complex XVII. Similarly, organic iridium complexes XIX, XX, XXI are at times herein referred to as monomeric organic iridium complexes. The generic cyclometallated ligands of monomeric organic iridium complexes XIX, XX, XXI may be, for example, any of the cyclometallated ligands discussed herein. In one embodiment, the cyclometallated ligands are derived from 1-phenylisoquinoline. In an alternate embodiment, the cyclometallated ligands are derived from 2-phenylpyridine.

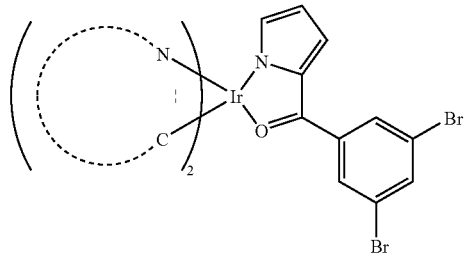

XIX

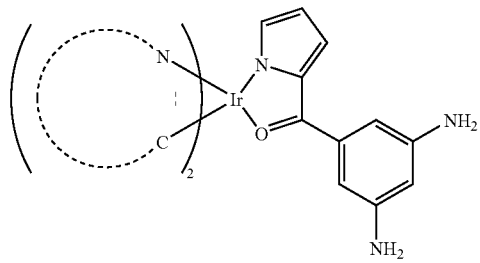

XX

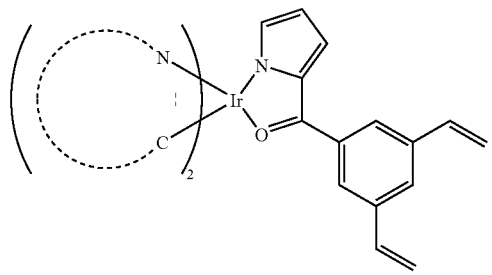

XXI

While monomeric organic iridium complexes XIX-XXI feature a substituted phenyl moiety bearing two reactive groups in the ketopyrrole ligand, those skilled in the art will appreciate that a variety of other substituted moieties bearing reactive groups are possible are possible, for example a multifunctional naphthyl moiety, a multifunctional tolyl moiety, a multifunctional 2-anthracenyl moiety, and the like. Those skilled in the art will understand that divinyl monomers such as organic iridium complex XXI may be useful as crosslinking agents in the preparation of olefin polymers comprising organic iridium complexes.

In one embodiment, the present invention provides a polymeric organic iridium complex prepared by condensation polymerization of a monomeric organic iridium complex with suitable co-monomers under conventional condensation polymerization conditions. In one embodiment, a polyimide may be synthesized by reacting a diamine containing iridium complex XX with a suitable dianhydride.

As noted, in one embodiment, the present invention provides a polymeric organic iridium complex comprising a polymeric cyclometallated ligand. Polymeric organic iridium complexes of this type may be prepared, for example, via Suzuki coupling of for example, 2,7-dibromo-9,9-dioctylfluorene with 9,9-dioctylflouren-2,7-diyl-bistrimethyleneborate in the presence of an organic iridium complex having structure XXII. Those skilled in the art will understand that under such circumstances the product polymer will comprise structural units derived from organic iridium complex XXII.

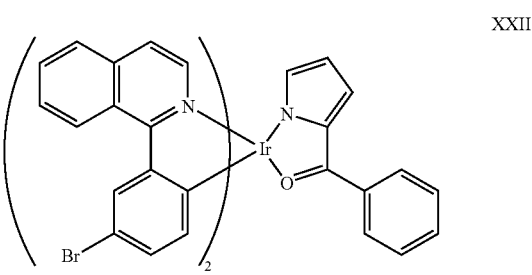

XXII

In one embodiment, the present invention provides a light emitting polymer composition comprising one or more of the polymeric organic iridium complexes disclosed herein.

In one embodiment, the light emitting polymer composition comprises at least one polymeric component in addition to the polymeric organic iridium complex. The polymeric component in addition to the polymeric organic iridium complex is not particularly limited and may for example be any of the polymer compositions disclosed herein. In one embodiment, the polymeric component in addition to the polymeric organic iridium complex is an electroactive polymer, for example an electroluminescent polymer such as poly(9,9-dioctyl fluorene).

In one embodiment, the present invention provides a light emitting polymer composition comprising a polymeric organic iridium complex, wherein the polymeric organic iridium complex comprises at least one cyclometallated ligand derived from a 1-phenylisoquinoline, a 2-phenylpyridine, a 1-styrylisoquinoline, or a mixture thereof; and at least one polymeric ketopyrrole ligand. In one embodiment, the present invention provides a polymeric organic iridium complex comprising structural units XXIII

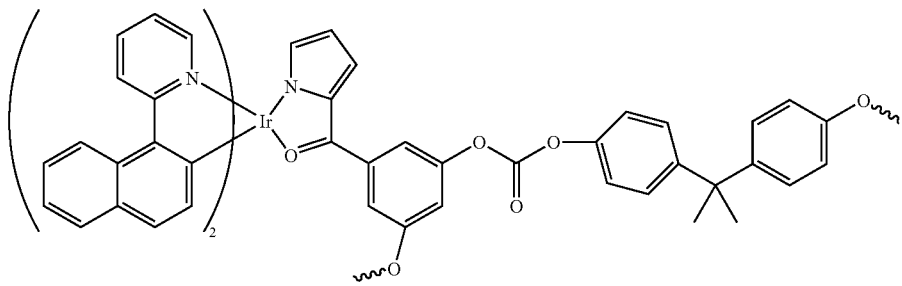

XXIII wherein each of the substructures ~~~ is a polymer chain. In one embodiment, the polymer chains are bisphenol A polycarbonate chains terminated by groups derived from para-cumylphenol. In an alternate embodiment of the present invention the polymer chains each comprise at least one organic iridium complex substructure derived from the monomeric organic iridium complex of Entry 8f in Table 8.

As noted, in one embodiment, the present invention provides novel ketopyrroles which are useful, for example. In the preparation of the organic iridium complexes of the present invention. Thus, in one embodiment, the present invention provides a composition comprising ketopyrrole XXIV

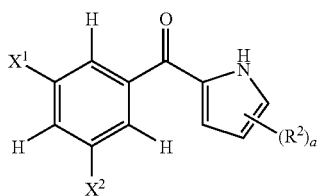

XXIV wherein $R^2$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is on integer from 0 to 3; and $X^1$ and $X^2$ are independently at each occurrence a bromine atom, a hydroxy group, or the group $OR^{10}$;

wherein the group $R^{10}$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical.

Ketopyrroles encompassed by generic structure XXIV are illustrated by 2-(3,5-dimethoxybenzoyl)-5-methylpyrrole, 2-(3,5-dimethoxybenzoyl)pyrrole, 2-(3,5-dihydroxybenzoyl)-5-methylpyrrole, 2-(3,5-dihydroxybenzoyl)pyrrole, 2-(3,5-dimethoxybenzoyl)-5-t-butylpyrrole, 2-(3,5-dimethoxybenzoyl)-3,4,5-trideuteriopyrrole, 2-(3,5-dibromobenzoyl)-5-methylpyrrole, 2-(3,5-dibromobenzoyl)-pyrrole 2-(3,5-bis(trimethylsilyloxy)benzoyl)pyrrole, bis(t-butyldimethylsilyloxy)benzoyl)pyrrole, and the like.

In a particular embodiment, the group $R^{10}$ is a $C_1$-$C_{50}$ aliphatic radical, for example a methacryloyl group. In another embodiment, the group $R^{10}$ is deuterated, i.e. $R^{10}$ comprises deuterium in an amount which exceeds the natural abundance level of deuterium ordinarily anticipated. In one embodiment, the group $R^{10}$ is at least 10 percent deuterated. In another embodiment, the group $R^{10}$ is at least 50 percent deuterated. In yet another embodiment, the present invention provides a ketopyrrole XXIV in which $R^2$ is deuterium, "a" is 3, and at least one of $X^1$ and $X^2$ are the group $OR^{10}$ wherein $R^{10}$ is at least 50 percent deuterated.

As the illustrative examples show, in certain embodiments the groups $X^1$ and $X^2$ are identical, for example when both $X^1$ and $X^2$ are bromine atoms as in 2-(3,5-dibromobenzoyl)-5-bromopyrrole, hydroxy groups as in 2-(3,5-dihydroxybenzoyl)pyrrole, methoxy groups as in 2-(3,5-dimethoxybenzoyl)pyrrole, or methacryloyloxy groups as in 2-(3,5-dimethacryloyloxybenzoyl)pyrrole.

In one embodiment, the present invention provides novel deuterated ketopyrroles having structure XXV

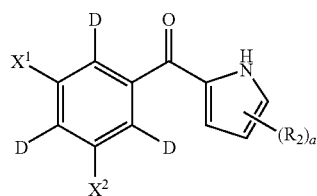

XXV wherein $R^2$, "a", $X^1$, and $X^2$ are defined as in structure XXIV. Ketopyrroles encompassed by generic structure XXV are illustrated by 2-(3,5-dimethoxy-2,4,6-trideuteriobenzoyl)-5-methylpyrrole, 2-(3,5-dimethoxy-2,4,6-trideuteriobenzoyl)-pyrrole, 2-(3,5-dihydroxy-2,4,6-trideuteriobenzoyl)-5-methylpyrrole, 2-(3,5-dihydroxy-2,4,6-trideuteriobenzoyl)pyrrole, 2-(3,5-dimethoxy-2,4,6-trideuteriobenzoyl)-5-t-butylpyrrole, 2-(3,5-dimethoxy-2,4,6-trideuteriobenzoyl)-3,4,5-trideuteriopyrrole, 2-(3,5-dibromo-2,4,6-trideuteriobenzoyl)pyrrole, 2-(3,5-dibromo-2,4,6-trideuteriobenzoyl)-3,4,5-trideuteriopyrrole, 2-(3,5-bis(trimethylsilyloxy)-2,4,6-trideuteriobenzoyl)pyrrole, bis(trimethylsilyloxy)-2,4,6-trideuteriobenzoyl)-3,4,5-trideuteriopyrrole, bis(t-butyldimethylsilyloxy)-2,4,6-trideuteriobenzoyl)pyrrole, and bis(t-butyldimethylsilyloxy)-2,4,6-trideuteriobenzoyl)-3,4,5-trideuteriopyrrole.

In one embodiment, the present invention provides an organic iridium complex comprising structural units derived from at least one of benzoylpyrroles XXIV or XXV. Thus, in one embodiment, the present invention provides an organic iridium complex comprising (i) at least one cyclometallated ligand and (ii) at least one ketopyrrole ligand, wherein said ketopyrrole ligand is derived from ketopyrrole XXIV or XXV.

The organic iridium compositions of the present invention whether polymeric or non-polymeric typically display strong charge transfer bands in their UV-Vis absorption spectra. Such absorption bands are believed to result from the transfer of electrons from molecular orbitals that are primarily ligand in character to molecular orbitals that are primarily metal in character, or alternatively, transfer of electrons from molecular orbitals that are primarily metal in character to molecular orbitals that are primarily ligand in character. Such charge transfer events are designated variously as Ligand-to-Metal Charge Transfer (LMCT) or Metal-to-Ligand Charge Transfer (MLCT). In certain embodiments the organic iridium compositions provided by the present invention are characterized by highly emissive excited states that may be produced when a voltage is applied. Materials possessing such properties are useful in the preparation of electronic devices, for example organic light emitting diodes (OLEDs). Other applications in which the organic iridium complexes of the present invention may be used include light emitting electrochemical cells, photo detectors, photoconductive cells, photo switches, phototransistors, and phototubes. Thus, in one embodiment, the present invention provides an electronic device comprising at least one electroactive layer comprising an organic iridium composition of the present invention.

The organic iridium compositions of the present invention are particularly well suited for use in an electroactive layers in organic light emitting devices. In one embodiment, the present invention provides an organic light emitting device comprising an electroactive layer which consists essentially of the organic iridium composition. In another embodiment, the present invention provides an organic light emitting device comprising the organic iridium composition as a constituent of an electroactive layer of an organic light emitting device. In one embodiment, the present invention provides an organic light emitting device comprising the organic iridium composition as a constituent of a light emitting electroactive layer of an organic light emitting device.

In one embodiment, the present invention provides an electronic device comprising a one or more of the polymer compositions of the invention. It has been found that in certain embodiments device performance may depend upon the physical properties of these polymer compositions, for example good film-forming abilities, good film strength, high glass transition temperature, good temperature resistance, and the like. In certain embodiments, the polymeric compositions provided by the present invention show enhanced solubility allowing the preparation of solvent cast films properties using techniques such as spin casting.

In one embodiment, the invention provides an organic light emitting device comprising at least one of the organic iridium compositions provided by the present invention. An organic light emitting device typically comprises multiple layers which include in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet excitons transfer energy to the environment by radiative decay. Triplet excitons, unlike singlet excitons, typically cannot undergo radiative decay and hence do not emit light except at very low temperatures. Theoretical considerations dictate that triplet excitons are formed about three times as often as singlet excitons. Thus the formation of triplet excitons, represents a fundamental limitation on efficiency in organic light emitting devices which are typically operated at or near ambient temperature. In one aspect, the organic iridium compositions provided by the present invention may serve as precursors to light emissive, short-lived excited state species which form as the normally unproductive triplet excitons encounter and transfer energy to the organic iridium composition. Thus, in one aspect, the present invention provides more efficient organic light emitting devices comprising at least one of the organic iridium compositions of the present invention.

In this disclosure, the organic electroluminescent layer is at times referred to as a "bipolar emission layer" and, as the previous discussion suggests, is a layer within an organic light emitting device which when in operation contains a significant concentration of both electrons and holes and provides sites for exciton formation and light emission. Other components which may be present in an organic light emitting device include: a "hole injection layer" which is defined as a layer in contact with the anode which promotes the injection of holes from the anode into the interior layers of the OLED; and an "electron injection layer" which is defined as a layer in contact with the cathode that promotes the injection of electrons from the cathode into the OLED; an "electron transport layer" which is defined as a layer which facilitates conduction of electrons from cathode to a charge recombination site. The electron transport layer need not be in contact with the cathode, and frequently the electron transport layer is not an efficient hole transporter and thus it serves to block holes migrating toward the cathode. During operation of an organic light emitting device comprising an electron transport layer, the majority of charge carriers (i.e. holes and electrons) present in the electron transport layer are electrons and light emission can occur through recombination of holes and electrons present in the electron transport layer. Additional components which may be present in an organic light emitting device include: a "hole transport layer" which is defined as a layer which when the OLED is in operation facilitates conduction of holes from the anode to charge recombination sites and which need not be in contact with the anode; and an "exciton-hole transporting layer" which is defined as layer which when the OLED is in operation facilitates the conduction of holes from the anode to charge recombination sites, and in which the majority of charge carriers are holes, and further in which excitons, typically triplet excitons, are also present and mobile, but do not emit light. Yet an additional component which may be present in an organic light emitting device is an "exciton-electron transporting layer" which is defined as a layer which when the OLED is in operation facilitates the conduction of electrons from the cathode to charge recombination sites, and in which the majority of charge carriers are electrons, and in which excitons, typically triplet excitons, are present and mobile, but do not emit light. Still yet additional components which may be present in an organic light emitting device include: a "hole transporting emission layer" which is defined as a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device; and an "electron transporting emission layer" which is defined as a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

FIGS. 1-11 illustrate various embodiments of organic light emitting devices provided by the present invention. FIG. 1 illustrates a simple organic light emitting device comprising an anode 10 and a cathode 20 with composition 30, a bipolar emissive material comprising an organic iridium composition of the present invention, disposed as a layer between the anode 10 and the cathode 20. Materials suitable for use as the anode 10 are illustrated by materials having a bulk conductivity of at least about 100Ω/(ohms per square), as measured by a four-point probe technique. Indium tin oxide (ITO) is typically used as the anode because it is substantially transparent to light transmission and thus facilitates the escape of light emitted from electro-active organic layer. Other materials which may be utilized as the anode layer include tin oxide, indium oxide, zinc oxide, indium zinc oxide, zinc indium tin oxide, antimony oxide, and mixtures thereof.

Materials suitable for use as the cathode 20 are illustrated by zero valent metals which can inject negative charge carriers (electrons) into the inner layer(s) of the OLED. Various zero valent metals suitable for use as the cathode 20 include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed as the cathode, for example a thin layer of a metal such as calcium, or a metal fluoride, such as LiF, covered by a thicker layer of a zero valent metal, such as aluminum or silver. In one embodiment, the cathode consists essentially of a single zero valent metal, for example a cathode consisting essentially of aluminum metal. The cathode may be deposited on the underlying element by physical vapor deposition, chemical vapor deposition, sputtering, or like technique. In one embodiment the cathode is transparent. The term "transparent" means allowing at least 50 percent, commonly at least 80 percent, and more commonly at least 90 percent, of light in the visible wavelength range to be transmitted through at an incident angle of less than or equal to 10 degrees. This means that a device or article, for example a cathode, described as being "transparent" will transmit at least 50 percent of light in the visible range which impinges on the device or article at an incident angle of about 10 degrees or less.

Composition 30, a bipolar emissive material comprising an organic iridium composition of the present invention, is illustrated by any of the non-polymeric and polymeric iridium compositions of the present invention. For example, composition 30 may consist entirely of a non-polymeric organic iridium complex (e.g. organic iridium complex X). Or, composition 30 may be a polymer composition comprising both a non-polymeric organic iridium complex (e.g. organic iridium complex X) and a polymeric component (e.g. poly(9,9-dioctyl fluorene) having a number average molecular weight of about 8,000 grams per mole). Or composition 30 may consist essentially of a polymeric organic iridium complex (e.g. the polymeric organic iridium complex of Example 34). Or composition 30 may comprise a polymeric organic iridium complex and an additional component (e.g. a mixture of the polymeric organic iridium complex of Example 34 and PDOT:PSS). In one embodiment, composition 30 may comprise any of the bipolar emissive materials 33 described herein together with at least one organic iridium complex or polymeric organic iridium complex of the invention.

Figure 2:
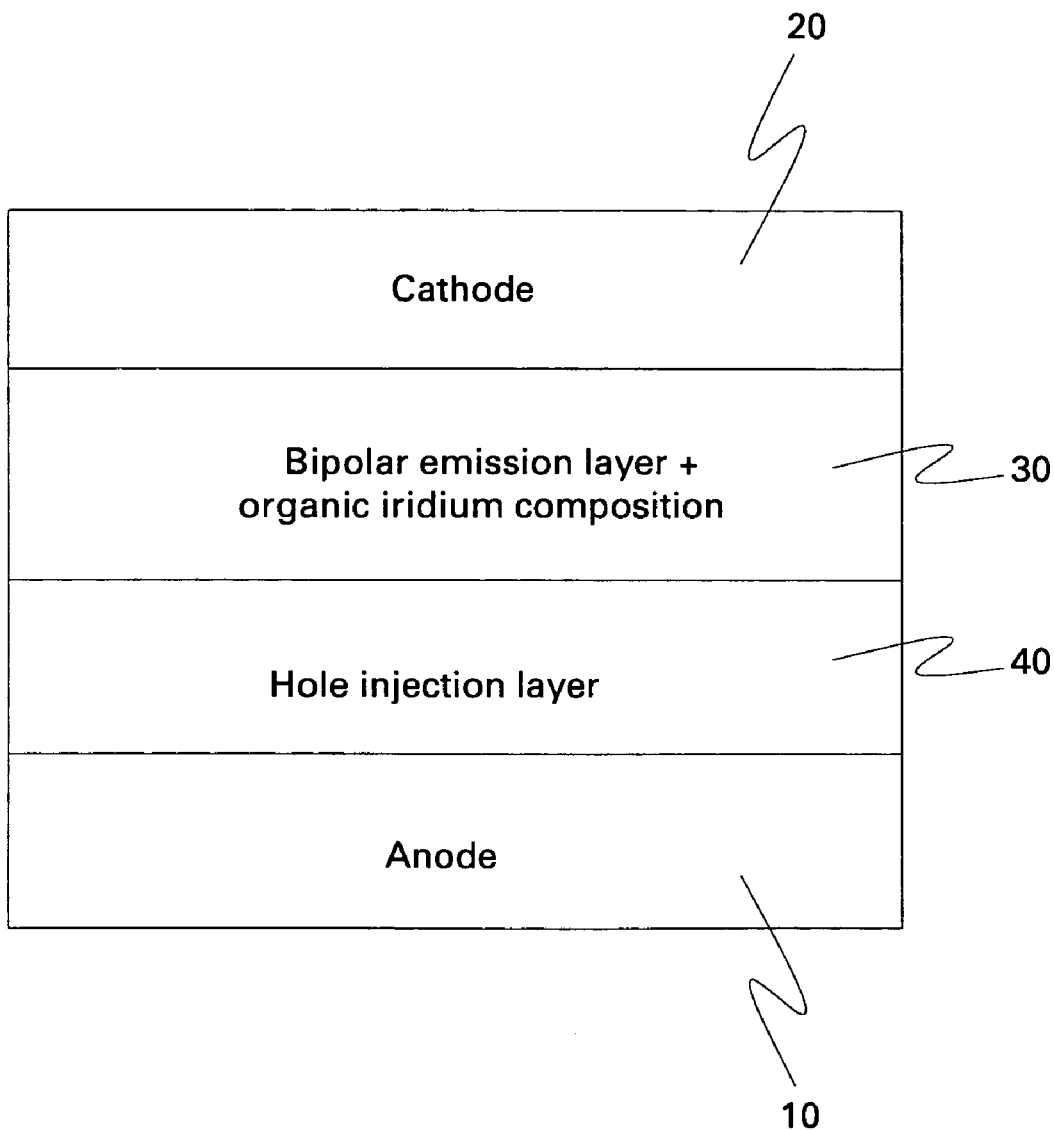
FIG. 2 represents an OLED device provided by the present invention.

FIG. 2 illustrates a organic light emitting device provided by the present invention further comprising a hole injection layer 40 disposed between the anode 10 and the bipolar emissive layer 30, of the organic light emitting device of FIG. 1. Materials suitable for use as hole injection layers are illustrated by BAYTRON commercially available from H.C. Stark, Inc. and hole injection layer (HIL) materials available from Air Products Corporation. Hole injection layer materials obtained from Air Products, Inc. are also referred to at times herein (or in supporting laboratory notebook records) as "AP-71", "AP-82" and "Air Products HIL conducting polymer".

Figure 3:
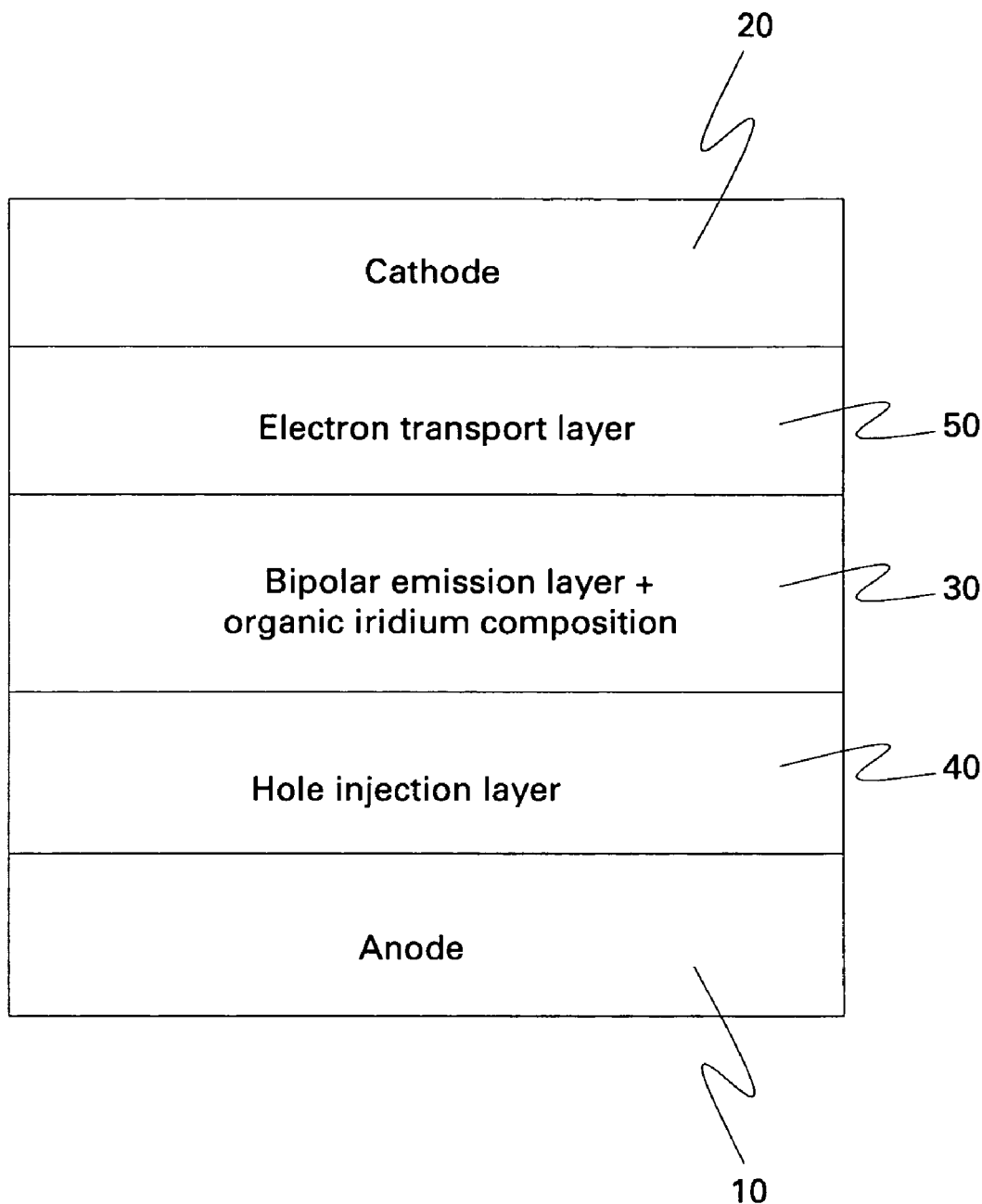
FIG. 3 represents an OLED device provided by the present invention.

FIG. 3 illustrates an organic light emitting device provided by the present invention further comprising an electron transport layer 50 disposed between the cathode 20 and the bipolar emissive layer 30, of the organic light emitting device of FIG. 2. Materials suitable for use as the electron transport layer are illustrated by poly(9,9-dioctyl fluorene); tris(8-hydroxyquinolato) aluminum ($Alq_3$); 2,9-dimethyl-4,7-diphenyl-1,1-phenanthroline; 4,7-diphenyl-1,10-phenanthroline; 2-(4-biphenylyl)-5-(4-t-butylphenyl)-1,3,4-oxadiazole; 3-(4-biphenylyl)-4-phenyl-5-(4-t-butylphenyl)-1,2,4-triazole, and the like.

Figure 4:
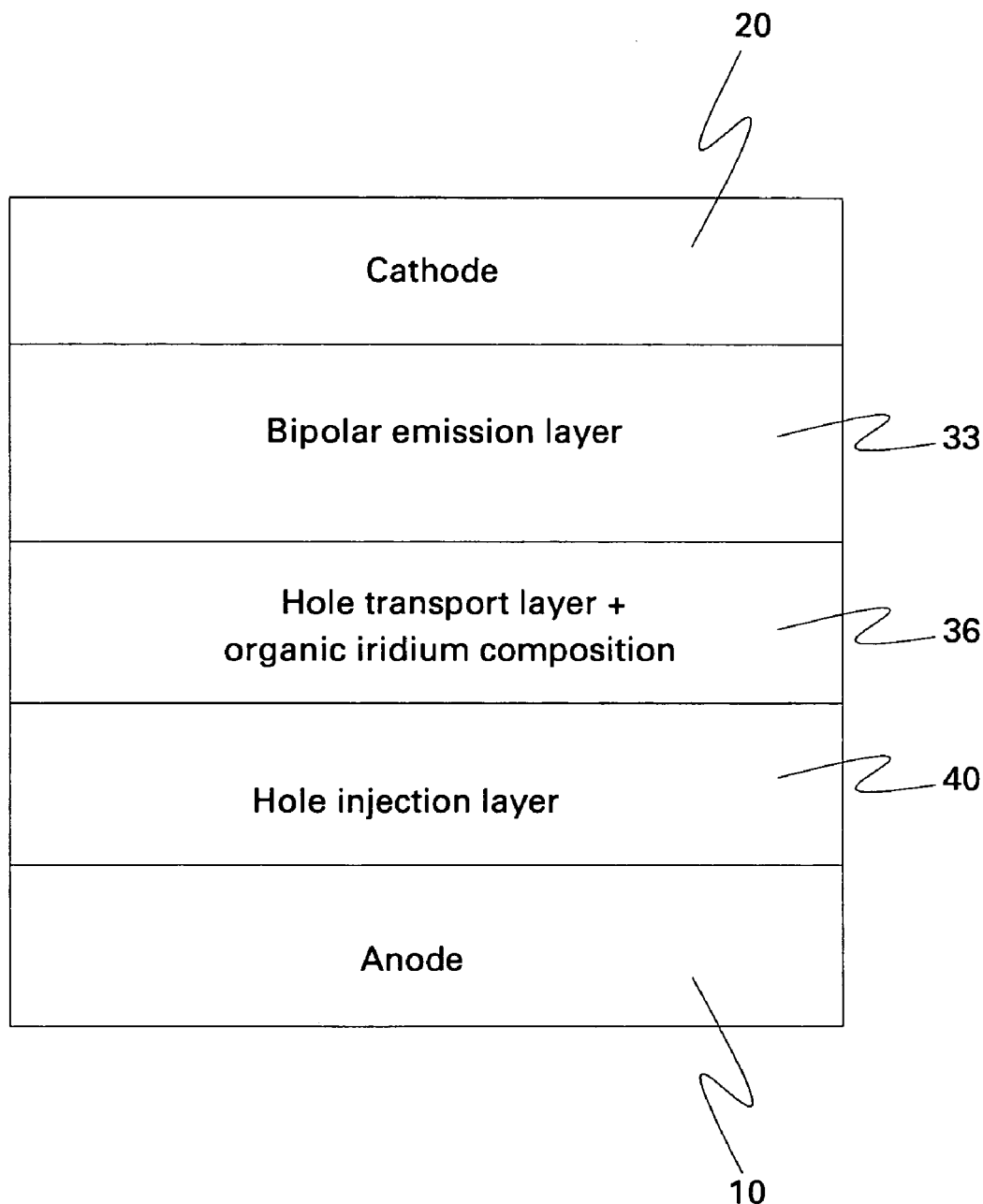
FIG. 4 represents an OLED device provided by the present invention.

FIG. 4 illustrates an organic light emitting device provided by the present invention comprising an anode 10 and a cathode 20, a bipolar emissive layer 33, a hole injection layer 40, and a hole transport layer 36 comprising at least one of the organic iridium compositions provided by the present invention. Materials suitable for use in the bipolar emission layer 33 are illustrated by electroluminescent polymers such as poly(9,9-dioctyl flourene), F8-TFB copolymer, and the like. Materials suitable for use in layer 36 include compositions comprising a hole transport material such as 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino)benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis(4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, and the like; and at least one organic iridium composition provided by the present invention.

Figure 5:
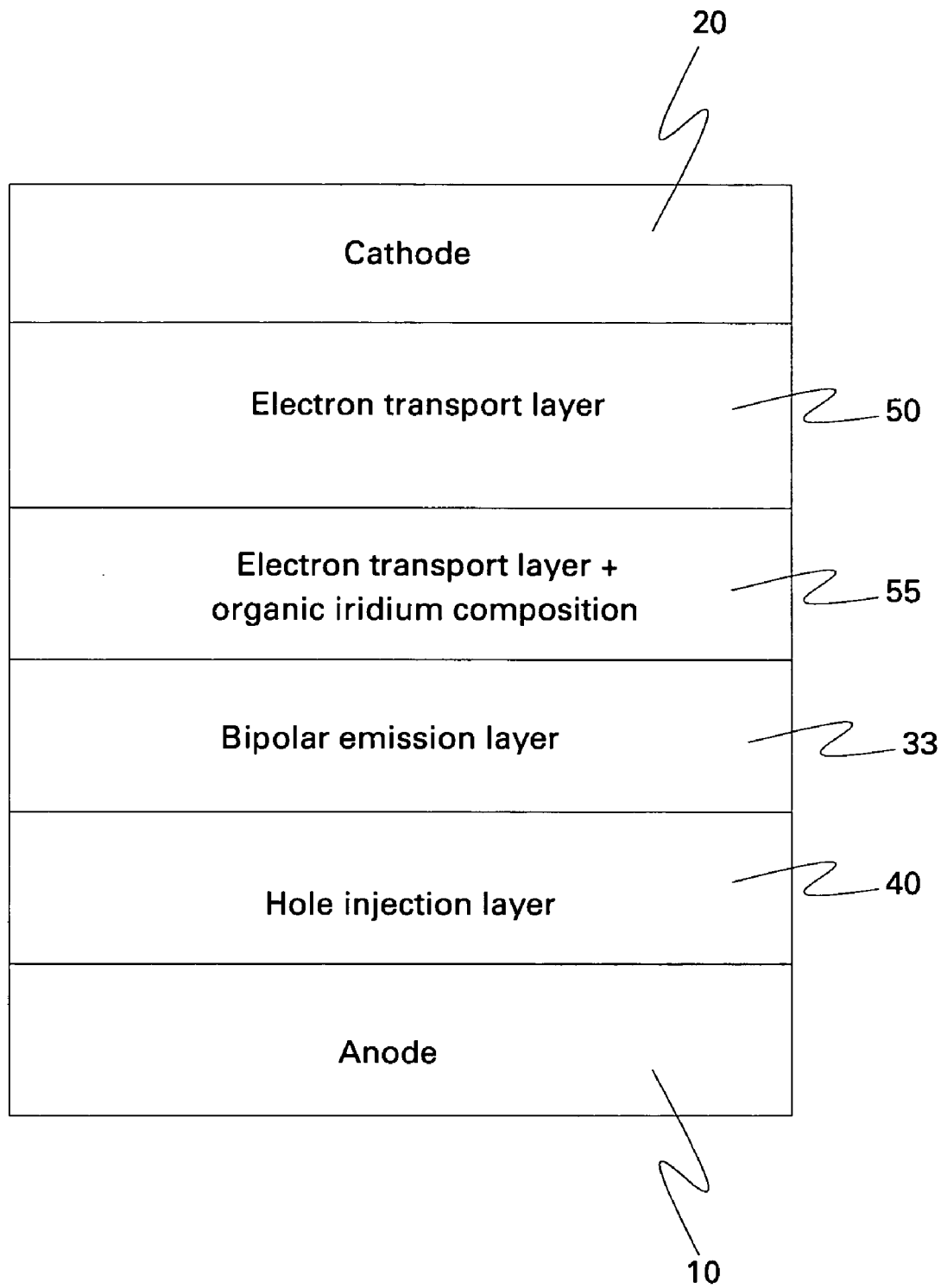
FIG. 5 represents an OLED device provided by the present invention.

FIG. 5 illustrates an organic light emitting device provided by the present invention comprising an anode 10, a cathode 20, a bipolar emissive layer 33, a hole injection layer 40, an electron transport layer 50, and an electron transport layer 55 comprising at least one of the organic iridium compositions provided by the present invention. Materials suitable for use in layer 55 include compositions comprising at least one electron transport material (e.g. $Alq_3$) and at least one organic iridium composition of the present invention (e.g. organic iridium complex VIII).

Figure 6:
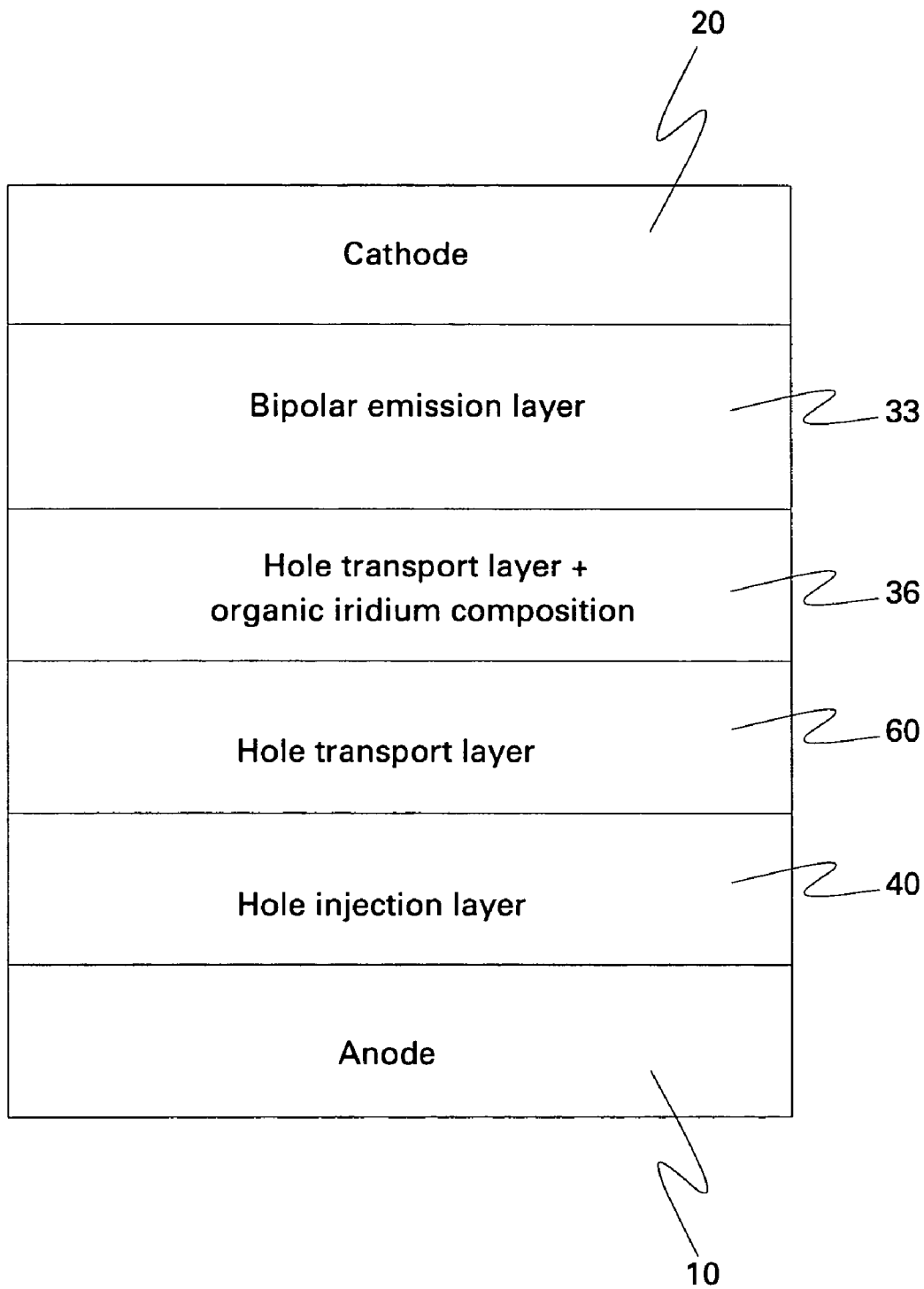
FIG. 6 represents an OLED device provided by the present invention.

FIG. 6 illustrates the organic light emitting device of FIG. 4 further comprising a second hole transport layer 60 disposed between the hole injection layer 40 and the first hole transport layer 36, said hole transport layer 36 comprising at least one organic iridium composition of the present invention and a hole transport material. Materials suitable for use in hole transport layer are illustrated by the listing of hole transport materials presented in the discussion of FIG. 4.

Figure 7:
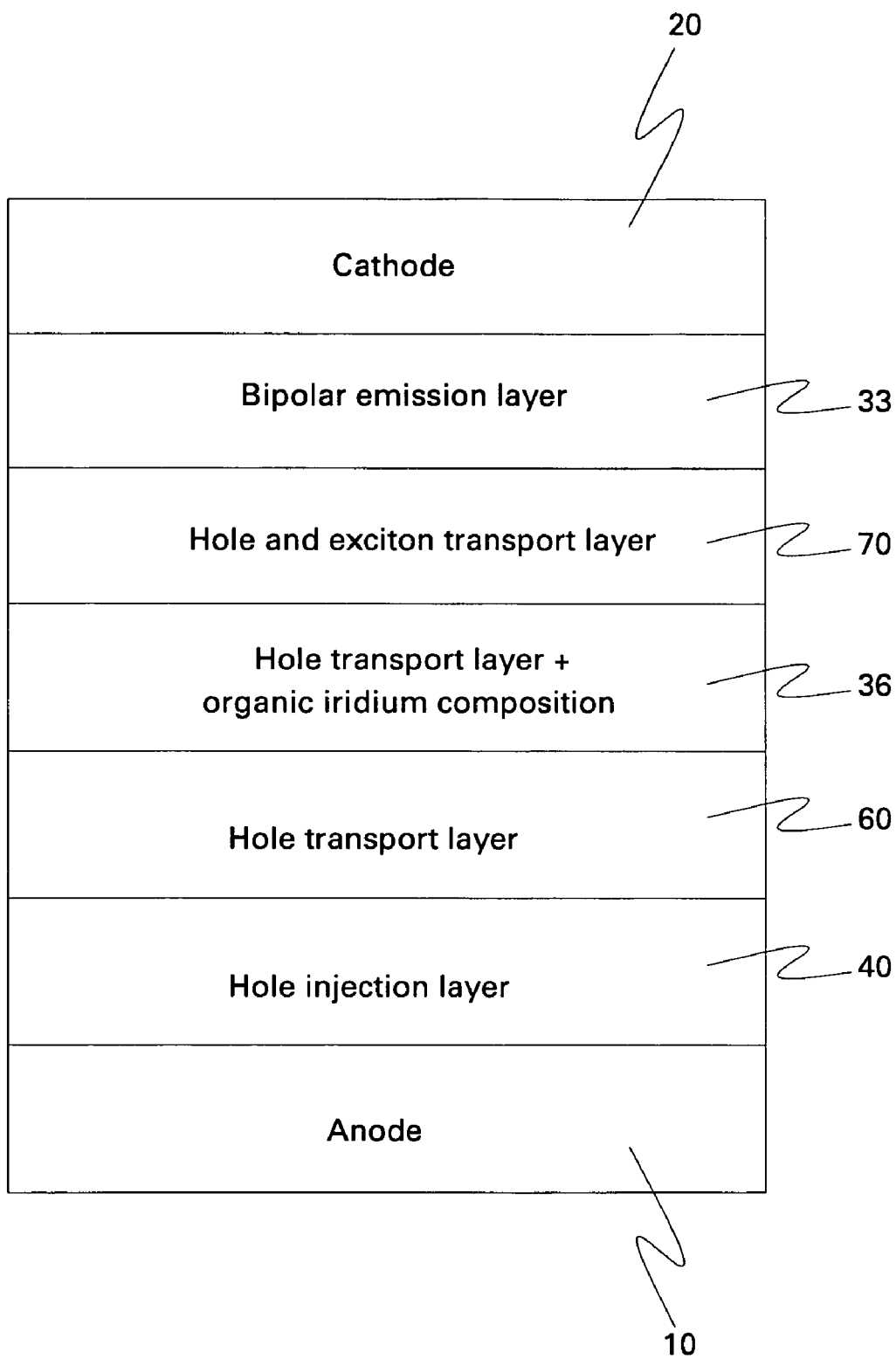
FIG. 7 represents an OLED device provided by the present invention.

FIG. 7 illustrates the organic light emitting device of FIG. 6 further comprising a exciton-hole transporting layer 70. Materials suitable for use in exciton-hole transporting layer are illustrated by F8-TFB copolymer.

Figure 8:
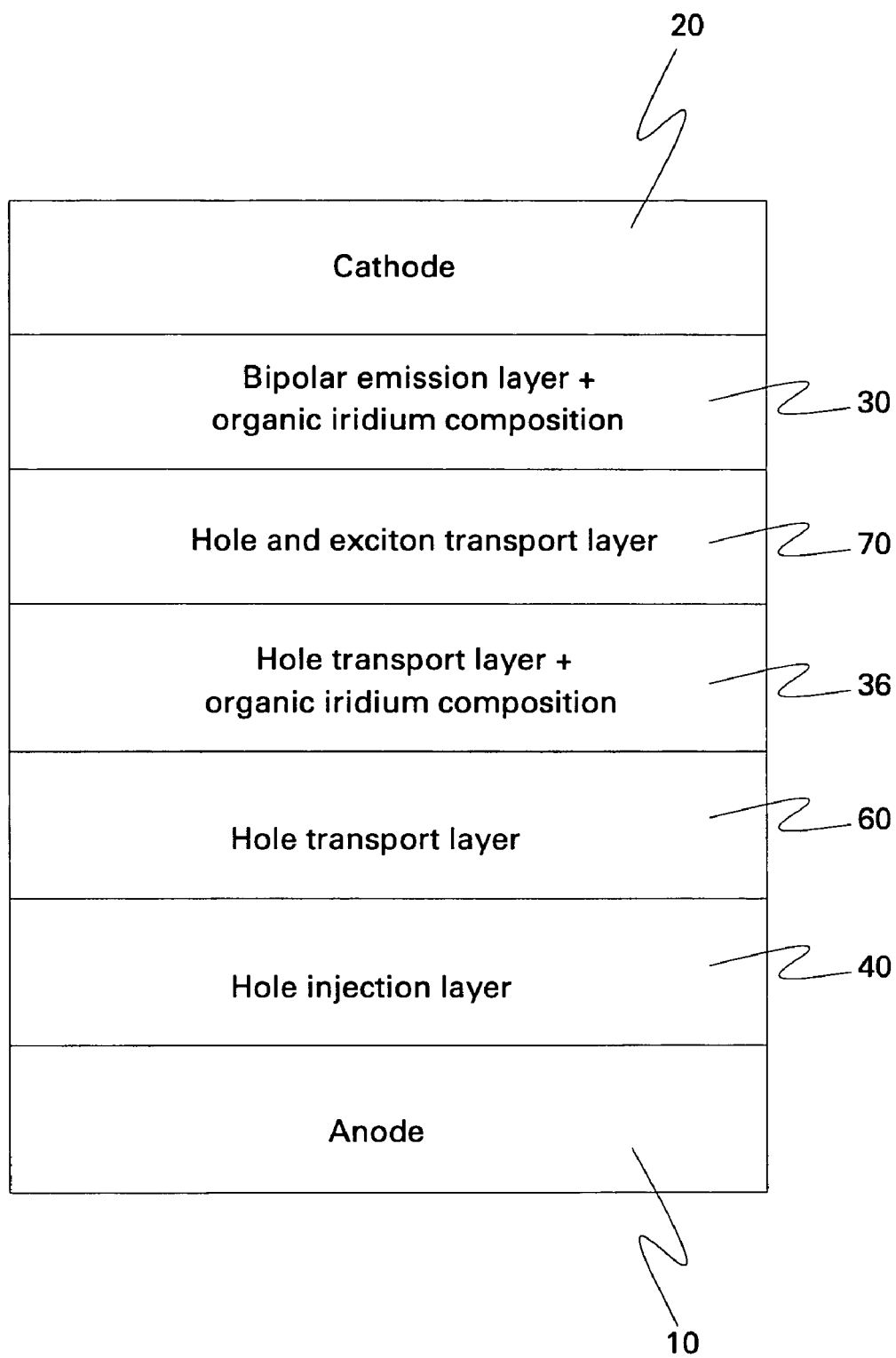
FIG. 8 represents an OLED device provided by the present invention.

FIG. 8 illustrates the organic light emitting device of FIG. 7 wherein the bipolar emission layer 33 is replaced by 30, a bipolar emissive material comprising an organic iridium composition of the present invention.

Figure 9:
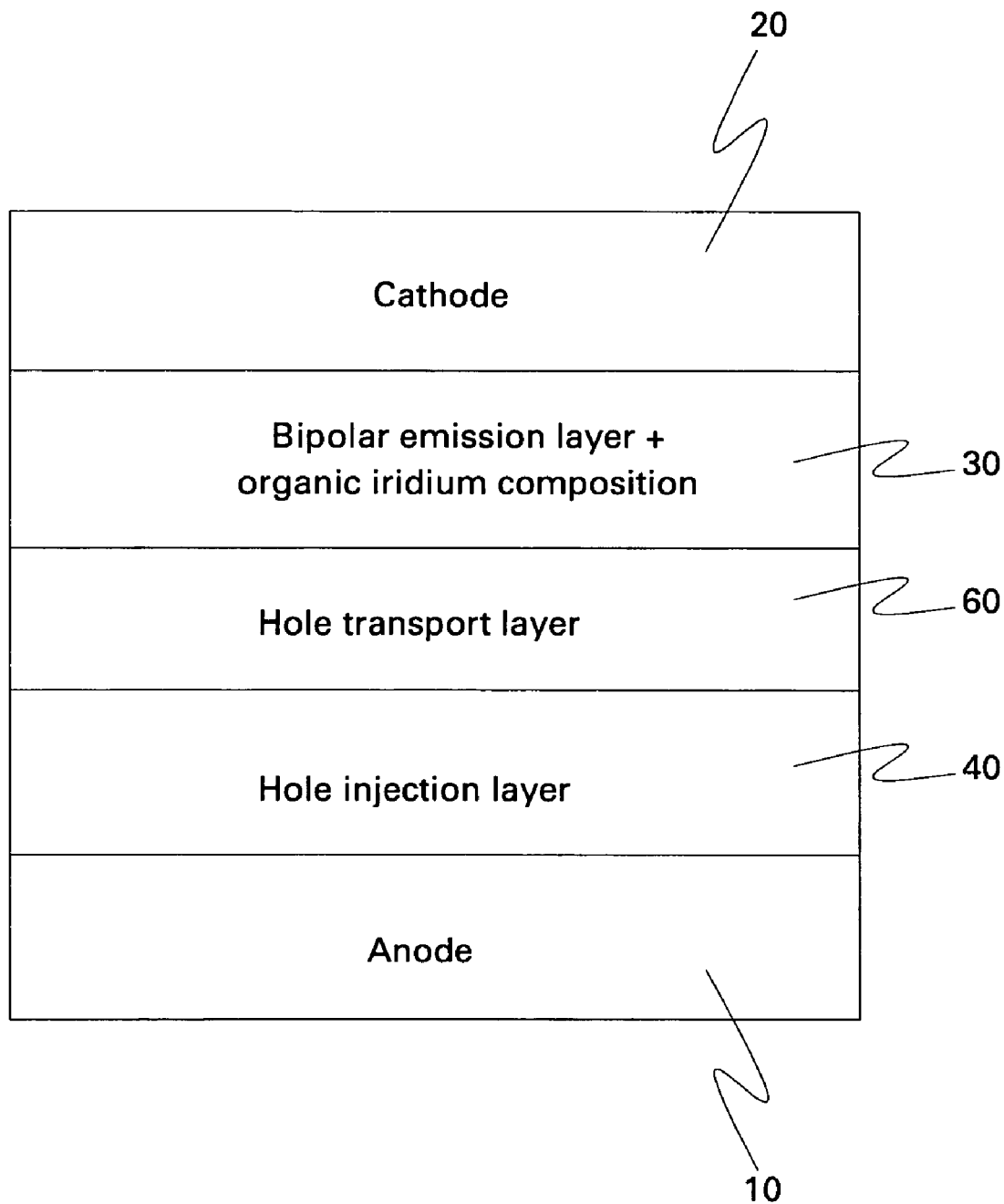
FIG. 9 represents an OLED device provided by the present invention.

FIG. 9 illustrates an organic light emitting device provided by the present invention comprising an anode 10, a cathode 20, a bipolar emissive composition 30 comprising an organic iridium composition of the present invention disposed between the cathode and a hole transport layer 60, and a hole injection layer 40.

Figure 10:
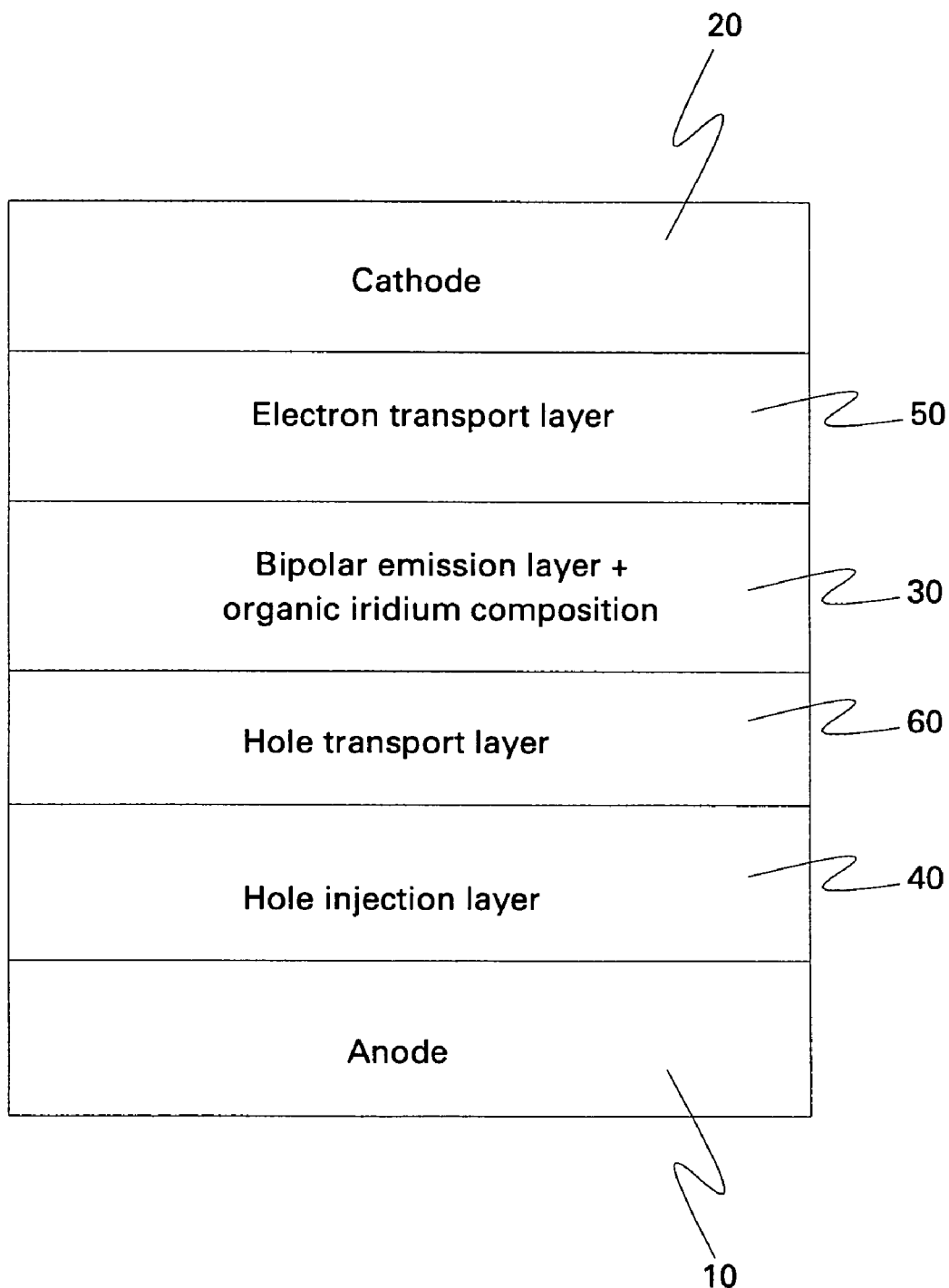
FIG. 10 represents an OLED device provided by the present invention.

FIG. 10 illustrates the organic light emitting device of FIG. 9 wherein an electron transport layer 50 is disposed between the cathode 20 and the bipolar emissive composition 30 comprising an organic iridium composition of the present invention.

Figure 11:
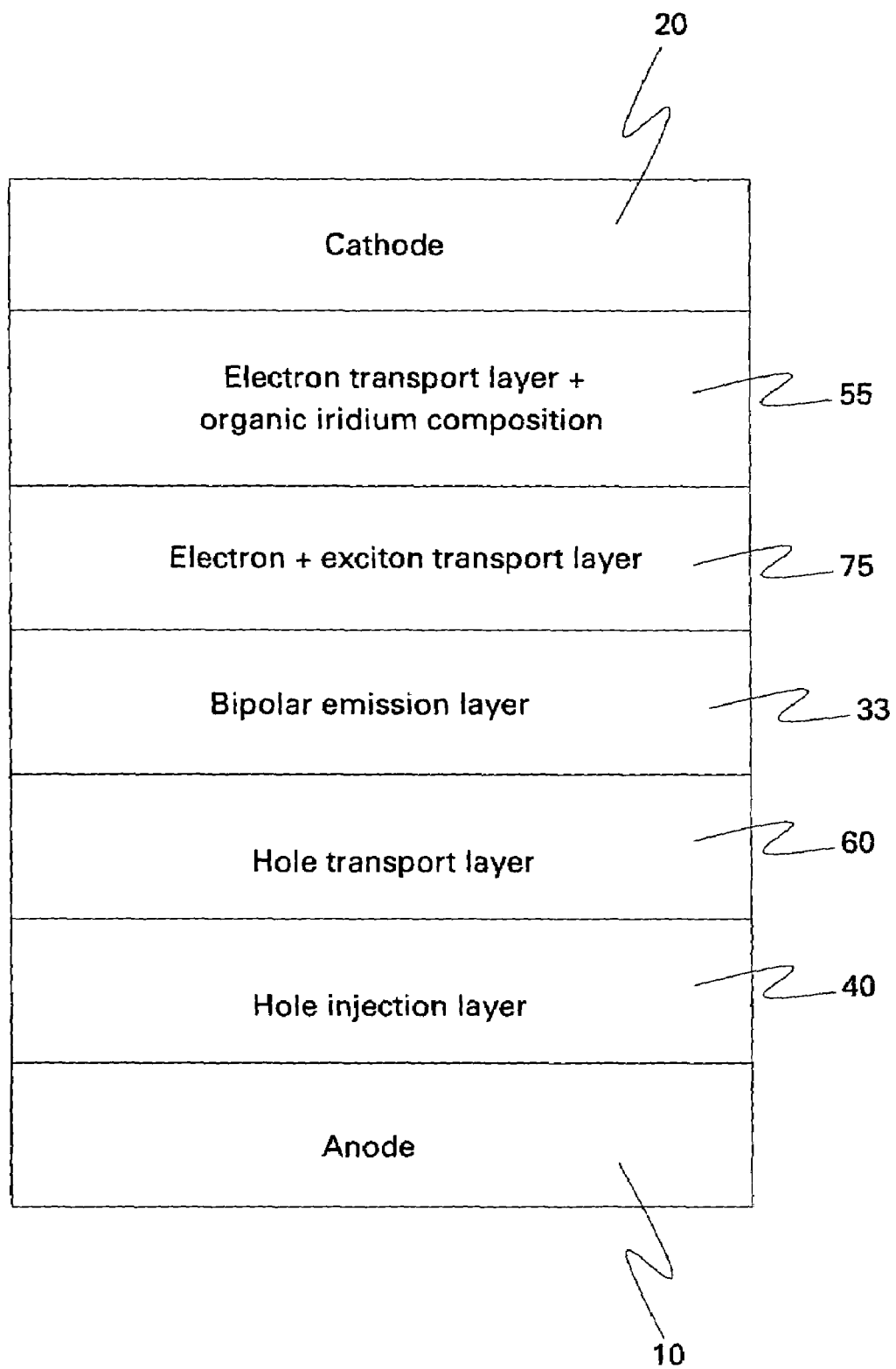
FIG. 11 represents an OLED device provided by the present invention.

FIG. 11 illustrates an organic light emitting device provided by the present invention comprising an anode 10, a cathode 20, a bipolar emissive layer 33, hole injection layer 40, a hole transport layer 60, and an exciton-electron transporting layer 75. Materials suitable for use in the exciton-electron transporting layer 75 include polyfluorene and derivatives of polyfluorene, e.g. poly(9,9-dioctyl fluorene).

EXAMPLES

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. While only certain features of the invention have been illustrated and described herein, many modifications and changes will occur to those skilled in the art. Accordingly, these examples are not intended to limit the invention, as defined in the appended claims, in any manner.

Thin layer chromatography (TLC) was performed on glass plates coated with silica-gel 60F (Merck 5715-7). The plates were inspected using UV light. Column chromatography was carried out using silica-gel 60 (Merck 9358, 230-400 mesh). All $^1$H- and $^{13}$C NMR spectra were recorded on a Bruker Advance 500 NMR spectrometer (at 500 MHz and 125 MHz, respectively) or a Bruker 400 NMR spectrometer (at 400 and 100 MHz, respectively). Chemical shifts were determined relative to tetramethylsilane using the residual solvent peak as a reference standard. High Resolution Mass spectra were measured with MALDI or EI ion sources. MALDI Mass spectra were obtained using dithranol as the supporting matrix.

Preparation of Chloride-Bridged Iridium Dimer Intermediates General Procedure

To a nitrogen purged solution containing a mixture of 2-methoxyethanol and water was added $IrCl_3 \cdot xH_2O$ (Strem Chemicals) followed by the addition of the cyclometallating ligand precursor (2.5-3.8 equiv.). The resulting mixture was heated at reflux for 15-48 h and the product was collected by vacuum filtration. In the following examples, the abbreviations "ppy", "piq", "F$_2$ppy" and "C6" have the following structures shown in Table 18. The asterisks (*) signal the point of attachment of the cyclometallated ligand to iridium.

TABLE 18

| Ligand Abbreviation | Ligand Chemical Structure | Chemical Name of Ligand Precursor |
|---|---|---|
| "ppy" | (structure) | 2-phenylpyridine |
| "piq" | (structure) | 1-phenylisoquinoline |
| "F$_2$ppy" | (structure) | 2-(2,4-difluorophenyl)-pyridine |
| "C6" | (structure) | Coumarin 6 |

Example 1

{(ppy)$_2$Ir(μ-Cl)}2: A mixture of 2-methoxyethanol and water (30 ml:10 mL) was degassed with N$_2$ for 15 min. To this solvent mixture was added $IrCl_3 \cdot xH_2O$ (0.388 g, 1.30 mmol) followed by 2-phenylpyridine (0.766 g, 4.94 mmol) and the mixture was heated at reflux for 24 h under an atmosphere of N$_2$. The reaction mixture was cooled to room temperature and the yellow precipitate was collected by filtration and washed with EtOH (50 mL), acetone (50 mL), and dried in air. The yellow precipitate was dissolved in CH$_2$Cl$_2$ and filtered to remove an insoluble material. The solution was concentrated to dryness and filtered after being suspended in hexanes. Yield: 0.539 g, 77%. $^1$H-NMR (400 MHz, CD$_2$Cl$_2$, 25° C.) δ 5.88 (d, 2H), 6.60 (m, 2H), 6.82 (m, 4H), 7.56 (d, 2H), 7.80 (m, 2H), 7.94 (d, 2H), 9.25 (d, 2H).

Example 2

{(F$_2$ppy)$_2$Ir(μ-Cl)}$_2$: A mixture of 2-methoxyethanol and water (20 ml 10 mL) was degassed with N$_2$ for 15 min. To this solvent mixture was added $IrCl_3 \cdot xH_2O$ (0.388 g, 1.30 mmol) followed by 2-(2,4-difluorophenyl)-pyridine (0.766 g, 4.94 mmol) and the mixture was heated at reflux for 15 h under an atmosphere of N$_2$. The reaction mixture was cooled to room temperature and poured into MeOH (200 mL). The yellow precipitate was collected by filtration and washed with MeOH and hexanes until the filtrate washes were colorless. The yellow precipitate was recrystallized from a mixture of toluene and hexanes to afford yellow needles. Yield: 2.20 g, 44%. $^1$H-NMR (400 MHz, CD$_2$Cl$_2$, 25° C.) δ5.29 (m, 4H), 6.38 (m, 4H), 6.87 (m, 4H), 7.87 (m, 4H), 8.33 (m, 4H), 9.12 (m, 4H).

Example 3

{(piq)$_2$Ir(μ-Cl)}$_2$: A mixture of 2-methoxyethanol and water (80 ml 20 mL) was degassed with N$_2$ for 15 min. To this solvent mixture was added IrCl$_3$.xH$_2$O (4.00 g, 13.4 mmol) followed by 2-phenylisoquinoline (6.90 g, 33.5 mmol) and the mixture was heated at reflux for 15 h under an atmosphere of N$_2$. The reaction mixture was cooled to room temperature and poured into MeOH (200 mL). The red precipitate was collected by filtration and washed with MeOH until the filtrate washes were colorless and dried in air. Yield: 6.68 g, 77%. $^1$H-NMR (500 MHz, CD$_3$SOCD$_3$, 25° C.) δ5.57 (d, 2H), 6.32 (d, 2H), 6.63 (t, 2H), 6.78 (t, 2H), 6.91 (t, 2H), 7.02 (t, 2H), 7.89 (m, 10H), 8.03 (d, 2H), 8.18 (m, 8H), 8.90 (m, 4H), 9.58 (d, 2H), 9.76 (d, 2H).

Example 4

{(C6)$_2$Ir(μ-Cl)}$_2$: A mixture of 2-methoxyethanol and water (12 ml: 1 mL) was degassed with N$_2$ for 10 min. To this solvent mixture was added IrCl$_3$-xH$_2$O (0.254 g, 0.853 mmol) followed by Coumarin 6 (0.750 g, 2.13 mmol) and the mixture was heated at reflux for 48 h under an atmosphere of N$_2$. The reaction mixture was cooled to room temperature, poured into 500 ml of acetone and concentrated to dryness under reduced pressure. The residue was suspended in acetone (200 mL) and the insoluble orange product was collected by filtration and washed with acetone until the filtrate washes were colorless. Yield: 0.548 g, 69%. $^1$H NMR (400 MHz, CD$_2$Cl$_2$, 25° C.) δ0.90 (t, 24H), 3.09 (m, 16H), 4.97 (d, 4H), 5.34 (m, 4H), 6.12 (d, 4H), 7.06 (m, 8H), 7.37 (m, 4H), 7.84 (m, 4H).

Preparation of Ketopyrrole Ligands

General Procedure for the Preparation of N,N-Diethyl Benzamide Precursors to Ketopyrrole Ligands, Method A:

To a stirred CH$_2$Cl$_2$ solution (20 mL) of the benzoyl chloride at −10° C. was added triethylamine (4 mL), followed by the dropwise addition of diethylamine (1.4 equivalents). The heterogeneous reaction mixture was allowed to warm to room temperature and stirring was continued for 30 minutes. The reaction mixture was then transferred to a separatory funnel containing H$_2$O (20 mL). The organic layer was separated and washed with 5% HCl (2×25 mL), H$_2$O (25 ml), and dried over Na$_2$SO$_4$. Removal of the CH$_2$Cl$_2$ solvent afforded the product.

General Procedure for the Preparation of N,N-Diethyl Benzamide Precursors to Ketopyrrole Ligands, Method B:

A mixture of thionyl chloride (6 mL) and the benzoic acid was heated at reflux until the starting benzoic acid dissolved. Excess thionyl chloride was removed under reduced pressure leaving the crude acid chloride as a low melting solid which was used without further purification. The crude acid chloride was dissolved in CH$_2$Cl$_2$(20 mL) and cooled to −10° C. To this stirred solution was added triethylamine (4 mL), followed by the dropwise addition of diethylamine (1.4 equivalents). The heterogeneous reaction mixture was allowed to warm to room temperature and was stirred for 30 minutes. The reaction mixture was transferred to a separatory funnel containing H$_2$O (20 mL). The organic layer was separated and washed with 5% HCl (2×25 mL), H$_2$O (25 ml), and dried over Na$_2$SO$_4$. The solvent was removed under reduced pressure to afford the product N,N-diethyl benzamide.

Exemplary N,N-diethylbenzamides, precursors to ketopyrrole ligands, prepared during the course of this investigation are gathered in Table 19 along with the method of preparation employed and the yield of the N,N-diethylbenzamide product.

TABLE 19

| Product Benzamide | Method | Yield | $^{13}$C NMR (100 MHz, CD$_2$Cl$_2$, 25° C.) δ |
|---|---|---|---|
| N,N-diethyl-4-bromobenzamide | A | 98% | 13.1, 14.5, 39.9, 43.8, 123.5, 128.6, 132.1, 137.1, 170.4. |
| N,N-diethyl-4-hexylbenzamide | A | 96% | 13.2, 14.3, 14.4, 21.2, 29.5, 31.9, 32.3, 36.3, 39.8, 43.7, 126.8, 128.8, 135.5, 144.7, 171.6. |
| N,N-diethyl-4-fluorobenzamide | A | 96% | 13.2, 14.5, 39.8, 43.9, 157.8 (d)*, 129.0 (d)*, 134.3, 162.3, 164.7, 170.5. |
| N,N-diethyl-4-methylbenzamide | B | 96% | 13.2, 14.5, 21.6, 39.7, 43.8, 126.8, 129.4, 135.3, 139.6, 171.6. |
| N,N-diethyl-4-methoxybenzamide | B | 99% | 13.5, 39.9, 43.7, 55.8, 114.0, 128.6, 130.4, 160.8, 171.3 |
| N,N-diethyl-3,5-dibromobenzamide | B | 95% | 13.1, 14.5, 40.0, 43.9, 123.5, 128.7, 135.1, 141.4, 168.1. |
| N,N-diethyl-3,5-dimethoxybenzamide | B | 98% | 13.2, 14.6, 39.6, 43.7, 56.0, 101.4, 104.5, 140.1, 161.4. 171.0. |

*doublet

General Procedure for Preparation of Ketopyrroles

Method C: A series of 2-aryl-ketopyrrole ligand precursors was prepared employing the Vilsmeier-Hack aroylation of pyrrole with a N,N-diethylbenzamide. The benzamide derivative was treated with POCl$_3$ to afford the Vilsmeier salt which upon treatment with pyrrole afforded after workup the ketopyrrole product in good yield. Thus, the benzamide (20 mmol) was dissolved in POCl$_3$(4 mL) and stirred at room temperature for 15 h. A solution of pyrrole (1.50 mL, 20 mmol) in 1,2-dichloroethane (50 mL) was then added and the mixture was stirred for 15 h. The reaction mixture was then poured into stirred aqueous Na$_2$CO$_3$ (15.0 g in 150 mL of H$_2$O). To the resultant two-phase mixture was added ethyl acetate (EtOAc) and the mixture was heated at reflux for 4 h. After cooling to room temperature, the mixture was filtered and transferred to a separatory funnel and the layers were separated. The organic layer was washed with H$_2$O (2×50 mL), dried over Na$_2$SO$_4$, and decolorized with charcoal. The crude ketopyrrole was isolated as a solid upon removal of the solvents and was purified by recrystallization from CH$_2$Cl$_2$/hexanes.

Method D: Alternatively, ketopyrroles were prepared in a single step by reaction of a benzoic acid with N-tosylpyrrole in a mixture of trifluoroacetic anhydride (TFAA) and $CH_2Cl_2$ at reflux. Thus, to a stirred $CH_2Cl_2$(20 mL) solution containing N-tosyl pyrrole (CAS No. 17639-64-4), maintained at −10° C., was added TFAA (trifluoroacetic anhydride, 50 mL), followed by the addition of the benzoic acid derivative in portions. The mixture was heated at reflux until TLC analysis showed complete conversion (ca. 48 hrs) after which the solvents were removed under reduced pressure. The residue was dissolved in $CH_2Cl_2$(20 mL) and transferred to a separatory funnel. The organic layer was washed with 10% $NaHCO_3$(4×100 mL), $H_2O$ (2×100), dried over $Na_2SO_4$, filtered, and finally concentrated to dryness. The residue was purified by column chromatography ($SiO_2$, EtOAc:Hexanes).

Exemplary ketopyrroles, prepared during the course of this investigation are gathered in Table 20 along with the method of preparation employed and the yield of the ketopyrrole product.

TABLE 20

| Benzamide/Benzoic Acid Precursor | Ketopyrrole Product | Method | Yield |
|---|---|---|---|
| N,N-diethyl-4-bromobenzamide | 2-(4-bromobenzoyl)pyrrole | C | 62% |
| N,N-diethyl-4-hexylbenzamide | 2-(4-hexylbenzoyl)pyrrole | C | 70% |
| N,N-diethyl-4-fluorobenzamide | 2-(4-fluorobenzoyl)pyrrole | C | 65% |
| N,N-diethyl-4-methylbenzamide | 2-(4-methylbenzoyl)pyrrole | C | 40% |
| N,N-diethyl-4-methoxybenzamide | 2-(4-methoxybenzoyl)pyrrole | C | 60% |
| N,N-diethyl-3,5-dibromobenzamide | 2-(3,5-dibromobenzoyl)pyrrole | C | 49% |
| N,N-diethyl-3,5-dimethoxybenzamide | 2-(3,5-dimethoxybenzoyl)pyrrole | C | 41% |
| 4-(trifluoroacetylamino)-benzoic acid | 1-toluenesulfonyl-2-(4-(trifluoroacetylamino)-benzoyl)pyrrole | D | 99% |
| 3,5-di(trifluoroacetylamino)-benzoic acid | 1-toluenesulfonyl-2-(3,5-di(trifluoroacetylamino)-benzoyl)pyrrole | D | 50% |
| 4-(trifluoroacetylaminomethyl)-benzoic acid | 1-toluenesulfonyl-2-(4-(trifluoroacetylaminomethyl)-benzoyl)pyrrole | D | 81% |

The product ketopyrroles could be further elaborated to other useful intermediates. In one instance, the dimethyl ether ketopyrrole derivative was converted into the corresponding bisphenol by treatment with $BBr_3$ in $CH_2Cl_2$. In addition to the preparation of simple ketopyrroles, more complex ketopyrroles such as 2-benzoyl-3,4-benzopyrrole derivatives were prepared in one step by reacting ortho-aminoacetophenone with alpha-bromo-4-bromoacetophenone in hot DMF (dimethyl formamide). 2-Benzoyl-4,5-benzopyrrole is also at times referred to herein as 2-benzoylindole.

Example 5

2-(3,5-Dihydroxybenzoyl)pyrrole: A solution of boron tribromide in $CH_2Cl_2$ was prepared by adding $BBr_3$(2.2 mL, 1 M in $CH_2Cl_2$) with stirring to $CH_2Cl_2$ (5 mL) at −78° C. under an inert atmosphere. To this solution was added (dropwise) a solution of 2-(3,5-dimethoxybenzoyl)pyrrole (200 mg, 0.864 mmol) in $CH_2Cl_2$(1 mL). The cooling bath was removed and the reaction mixture stirred overnight at room temperature. The reaction mixture was then poured into a separatory funnel containing $H_2O$ (20 mL) and EtOAc (20 mL). The layers were separated and the $H_2O$ layer was extracted with EtOAc (2×15 mL). The combined organic extracts were dried over $Na_2SO_4$, filtered and concentrated to afford the crude product as sticky solid. Yield (135 mg, 77%). $^1H$ NMR (400 MHz, $CD_3OD$, 25° C.) δ6.28 (m, 1H), 6.45 (t, 1H), 6.73 (d, 2H), 6.88 (m, 1H), 7.15 (m, 1H); $^{13}C$ NMR (100 MHz, $CD_3OD$, 25° C.) δ107.0, 108.5, 111.6, 121.5, 127.5, 132.3, 142.1, 159.8, 187.0; HRMS (EI): m/z 203.0560 (100) {M}$^+$.

Example 6

2-(4-Bromobenzoyl)-3-methylindole: A mixture of ortho-aminoacetophenone (2.70 g, 20 mmol) and alpha-bromo-4-bromoacetophenone (5.56 g, 20 mmol) was dissolved in anhydrous DMF (50 mL) and heated at 90° C. for 14 hrs. The mixture was poured over crushed ice (1000 mL) and the precipitate was collected by filtration. The crude product was subjected to flash chromatography through a column of silica gel using $CH_2Cl_2$:hexanes as the eluant. The product 2-(4-bromobenzoyl)-3-methylindole, also referred to as 2-benzoyl-4,5-benzopyrrole, was recrystallized from $CH_2Cl_2$/hexanes as yellow needles. Yield (2.70 g, 45%). $^1H$ NMR (400 MHz, $CD_2Cl_2$, 25° C.) δ2.27 (s, 3H), 7.16 (m, 1H), 7.35 (m, 1H), 7.42 (m, 1H), 7.67 (m, 5H), 8.98 (bs, 1H); $^{13}C$ NMR (100 MHz, $CD_2Cl_2$, 25° C.) δ11.6, 112.4, 120.8, 120.9, 121.8, 127.1, 127.2, 129.5, 131.0, 132.3, 137.2, 138.8, 188.4; HRMS (EI): m/z 313.0077 (100) {M}$^+$.

Example 7

2-(4-Aminobenzoyl)pyrrole: To a stirred EtOH (4 mL) solution containing N-toluenesulfonyl-2-(4-(trifluoroacetylamino)benzoyl)pyrrole (0.500 g, 1.15 mmol), was added 40% KOH solution (2 mL) and the mixture was heated at reflux until thin layer chromatography (TLC) analysis showed complete conversion of the starting material. The resulting solution was cooled to room temperature and diluted with EtOAc (20 mL), and the mixture was evaporated to dryness. The crude product was purified by column chromatography ($SiO_2$, EtOAc:Hexanes) to afford the purified product 2-(4-aminobenzoyl)pyrrole (196 mg, 94% yield). $^1H$ NMR (400 MHz, $CD_2Cl_2$, 25° C.) δ4.19 (bs, 2H), 6.33 (m, 1H), 6.72 (d, 2H), 6.88 (m, 1H), 7.10 (m, 1H), 7.82 (d, 2H), 9.90 (bs, 1H); $^{13}C$ NMR (100 MHz, $CD_2Cl_2$, 25° C.) δ110.9114.2, 118.0, 124.5, 128.5, 131.8, 131.9, 151.3, 183.5; HRMS (EI): m/z 186.0793 (100) {M}$^+$.,

Example 8

2-(3,5-Diaminobenzoyl)pyrrole: To a stirred EtOH (10 mL) solution of N-toluenesulfonyl-2-(3,5-di(trifluoroacetylamino)benzoyl)pyrrole (1.00 g, 1.83 mmol), was added 40% KOH solution (2 mL) and the mixture was heated at reflux until TLC analysis showed complete conversion. The resulting solution was cooled to room temperature and worked up as in Example 7. The crude product was purified by column chromatography (SiO$_2$, CH$_2$Cl$_2$:MeOH) to afford the purified product 2-(3,5-diaminobenzoyl)pyrrole (237 mg, 65% yield). $^1$H NMR (500 MHz, CD$_3$OD, 25° C.) δ 2.43 (s, 3H), 6.45 (m, 1H), 6.90 (m, 1H), 7.41 (d, 2H), 7.88 (m, 3H), 7.93 (d, 2H), 8.39 (t, 1H); $^{13}$C NMR (100 MHz, CD$_3$OD, 25° C.) δ 104.8, 105.7, 109.4, 119.5, 125.2, 130.5, 139.8, 147.8, 186.0; HRMS (EI): m/z 201.0896 (100) {M}$^+$.

Example 9

2-(4-Aminomethylbenzoyl)pyrrole: To a stirred EtOH (10 mL) solution containing N-toluenesulfonyl-2-(4-(trifluoroacetylaminomethyl)benzoyl)pyrrole (1.00 g, 2.20 mmol), was added 40% KOH solution (2 mL) and the mixture was heated at reflux until TLC analysis showed complete consumption of the starting material. The reaction mixture was then cooled to room temperature worked up as in Example 7. The crude product was suspended in H$_2$O, filtered and dried to afford the purified product 2-(4-aminomethylbenzoyl)pyrrole (381 mg, 86%). $^1$H NMR (500 MHz, CD$_3$OD, 25° C.) δ2.43 (s, 3H), 4.53 (s, 2H), 6.42 (m, 1H), 6.77 (m, 1H), 7.41 (d, 2H), 7.72 (d, 2H), 7.85 (m, 1H), 7.95 (d, 2H), 8.39 (t, 1H); $^{13}$C NMR (100 MHz, CD$_3$OD, 25° C.) δ44.6, 109.7, 119.4, 125.6, 126.5, 128.4, 130.4, 136.8, 146.1, 184.6; HRMS (EI): m/z 200.0940 (100) {M}$^+$.

Example 10

2-(3,5-Di(allyloxy)benzoyl)pyrrole: To a solution of 2-(3,5-dihydroxybenzoyl)pyrrole (100 mg, 0.492 mmol) in DMF (2.0 mL) at room temperature was added successively potassium carbonate (272 mg, 1.97 mmol) and allyl bromide (236 mg, 1.97 mmol). The mixture was stirred for 24 h, poured into water, and then extracted with Et$_2$O. The extract was washed with brine, dried over Mg$_2$SO$_4$, and concentrated to dryness. The resulting residue was subjected to column chromatography on silica gel using CH$_2$Cl$_2$ as the eluant to give the purified product as a colorless oil. Yield (123 mg, 88%). $^1$H NMR (400 MHz, CD$_2$Cl$_2$, 25° C.) δ 4.58 (m, 4H), 5.30 (m, 2H), 5.43 (m, 2H), 6.08 (m, 2H), 6.34 (m, 1H), 6.70 (t, 1H), 6.92 (m, 1H), 7.03 (d, 2H), 7.17 (m, 1H), 9.8.3 (bs, 1H); $^{13}$C NMR (100 MHz, CD$_2$Cl$_2$, 25° C.) δ69.7, 106.1, 108.2, 111.5, 118.0, 119.7, 125.9, 131.6, 133.7, 140.8, 160.2, 184.4; HRMS (EI): m/z 283.1179 (100) {M}$^+$.

Preparation of Organic Iridium Complexes

General Methods: The organic iridium complexes (Ir(III) complexes) provided by the invention were prepared by contacting the N-tosyl- or unprotected ketopyrrole ligand precursor in 2-methoxyethanol with excess sodium hydride (NaH) at or below room temperature followed by addition of a chloride-bridged cyclometallated iridium dimer intermediate {(ppy)$_2$Ir(μ-Cl)}$_2$, {(F$_2$ppy)$_2$Ir(μ-Cl)}2, {(C6)$_2$Ir(μ-Cl$_2$)}$_2$ or {(piq)$_2$Ir(μ-Cl)}$_2$ and heating the reaction mixture. Typically, 2.2 equivalents of the N-tosyl- or the unprotected ketopyrrole ligand precursor was used per mole of the iridium dimer intermediate.

Example 11

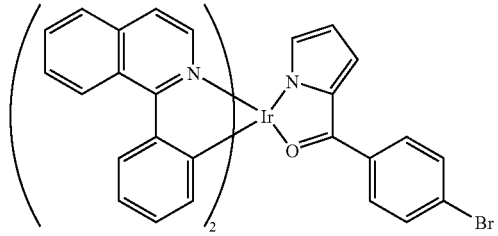

XXVI

Iridium Complex XXVI: To a stirred solution of 2-(4-bromobenzoyl)pyrrole (106 mg, 0.428 mmol) in 2-methoxyethanol (4 mL) was added solid sodium hydride (40.0 mg, 1.67 mmol) and the resultant yellow solution was stirred for 5 minutes at ambient temperature. The chloride-bridged cyclometallated iridium dimer intermediate {(piq)$_2$Ir(μ-Cl)} 2 (260 mg, 0.200 mmol) was then added and the mixture was heated at 70° C. for 1 h. The dark red product mixture was cooled to room temperature and poured into MeOH (150 mL) causing the product to precipitate. The product cyclometallated ketopyrrole complex XXVI was collected by filtration, washed with MeOH, and dried in air. Yield (327 mg, 96%). $^1$H NMR (400 MHz, CD$_2$Cl$_2$, 25° C.) δ6.32 (d, 1H), 6.42 (m, 2H), 6.55 (t, 1H), 6.70 (m, 1H), 6.79 (m, 1H) 7.01 (m, 2H), 7.18 (d, 1H), 7.44 (d, 1H), 7.56 (d, 2H), 7.73 (m, 4H), 7.83 (d, 2H), 7.87 (m, 1H), 7.93 (m, 1H), 8.27 (d, 2H), 8.31 (d, 1H), 8.98 (m, 2H); HRMS (MALDI): m/z 849.0899 (100) {M}$^+$.

Example 12

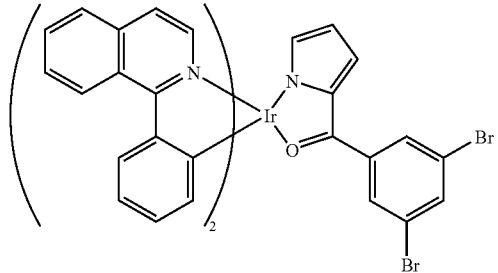

XXVII

Iridium Complex XXVII: 2-(3,5-Dibromobenzoyl)pyrrole (1.31 g, 3.39 mmol) was converted to cyclometallated ketopyrrole complex XXVII as in Example 11. The product was collected by filtration, washed with MeOH, and dried in air. Yield (2.74 g, 96%). $^1$H NMR (400 MHz, CD$_2$Cl$_2$, 25° C.) δ6.36 (d, 1H), 6.42 (m, 2H), 6.59 (t, 1H), 6.74 (m, 1H), 6.79 (m, 1H) 7.01 (m, 2H), 7.18 (m, 1H), 7.35 (d, 1H), 7.46 (d, 1H), 7.54 (d, 1H), 7.75 (m, 4H), 7.78 (t, 1H), 7.92 (m, 2H), 8.03 (d, 2H), 8.28 (m, 3H), 9.00 (m, 2H); HRMS (MALDI): m/z 928.9338 (100) {M}+.

2H), 8.35 (d, 1H), 8.99 (m, 2H); HRMS (MALDI): m/z 855.2345 (100) {M}+Yield (248 mg, 98%).

Example 13

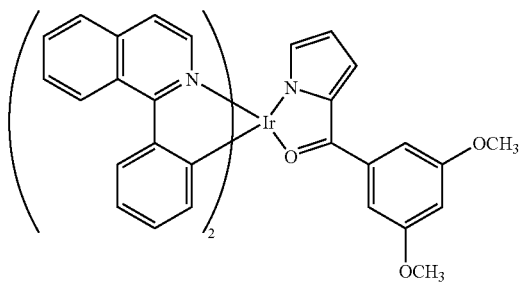

XIV

Iridium Complex XIV: 2-(3,5-Dimethoxybenzoyl)pyrrole (85.0 mg, 0.367 mmol) was converted to cyclometallated ketopyrrole complex XIV as in Example 11. Yield (254 mg, 97%). $^1$H NMR (400 MHz, CD$_2$Cl$_2$, 25° C.) δ3.77 (s, 6H), 6.30 (m, 1H), 6.41 (m, 1H), 6.46 (m, 1H), 6.53 (t, 1H), 6.57 (t, 1H), 6.73 (m, 1H), 6.79 (m, 1H), 7.00 (m, 4H), 7.18 (m, 1H), 7.34 (d, 1H), 7.45 (d, 1H), 7.52 (d, 1H), 7.74 (m, 4H), 7.91 (m, 2H), 8.28 (d, 2H), 8.34 (d, 1H), 8.99 (m, 2H); HRMS (MALDI): m/z 831.1916 (100) {M}+.

Example 14

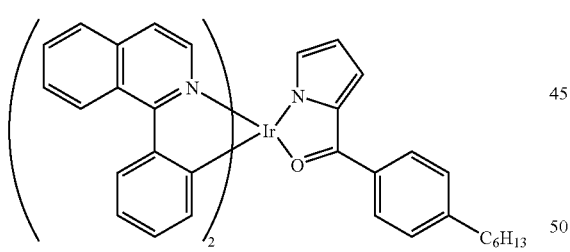

XXVIII

Iridium Complex XXVIII: To a stirred solution of 2-(4-hexylbenzoyl)pyrrole (98.0 mg, 0.385 mmol) in 2-methoxyethanol (5 mL) was added sodium hydride (12.0 mg, 0.500 mmol) causing the solution to turn yellow in color. After letting this solution stir for 5 min, {(piq)$_2$Ir(μ-Cl)}$_2$ (200 mg, 0.154 mmol) was added and the mixture was then heated at 80° C. for 1.5 hrs. The dark red reaction mixture was cooled to room temperature and poured into MeOH (150 mL) causing the product to precipitate. The product was collected by filtration, washed with MeOH, and dried in air. Yield (248 mg, 98%). $^1$H NMR (400 MHz, CD$_2$Cl$_2$, 25° C.) δ 0.87 (t, 2H), 1.29 (m, 6H), 1.59 (m, 2H), 2.65 (t, 2H), 6.31 (m, 1H), 6.42 (m, 1H), 6.46 (m, 1H), 6.52 (t, 1H), 6.73 (m, 1H), 6.79 (m, 1H), 7.00 (m, 2H), 7.20 (m, 1H), 7.25 (d, 2H), 7.31 (d, 1H), 7.43 (d, 1H), 7.53 (d, 1H), 7.72 (m, 4H), 7.89 (m, 4H), 8.28 (d,

Example 15

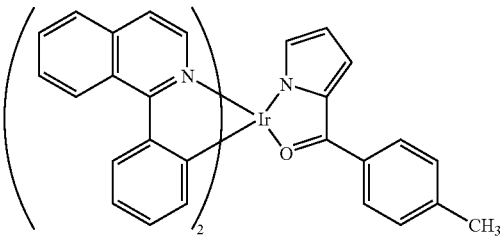

XXIX

Iridium complex XXIX: 2-(4-Methylbenzoyl)pyrrole (71.0 mg, 0.385 mmol) was converted to cyclometallated ketopyrrole complex XXIX as in Example 11. Yield (221 mg, 98%). $^1$H NMR (400 MHz, CD$_2$Cl$_2$, 25° C.) δ 2.39 (s, 3H), 6.30 (m, 1H), 6.43 (m, 2H), 6.52 (t, 1H), 6.71 (m, 1H), 6.79 (m, 1H), 7.00 (m, 2H), 7.18 (m, 1H), 7.25 (d, 2H), 7.32 (d, 1H), 7.44 (d, 1H), 7.53 (d, 1H), 7.73 (m, 4H), 7.88 (m, 4H), 8.27 (d, 2H), 8.34 (d, 1H), 8.99 (m, 2H); HRMS (MALDI): m/z 785.2699 (100) {M}+.

Example 16

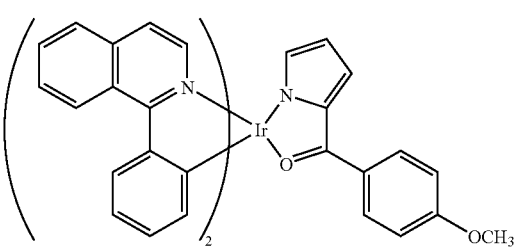

XXX

Iridium Complex XXX: 2-(4-Methoxybenzoyl)pyrrole (77.0 mg, 0.385 mmol) was converted to cyclometallated ketopyrrole complex XXX as in Example 11. Yield (229 mg, 96%). $^1$H NMR (400 MHz, CD$_2$Cl$_2$, 25° C.) δ3.83 (s, 3H), 6.30 (m, 1H), 6.42 (m, 2H)<6.50 (t, 1H), 6.73 (m, 1H), 6.78 (m, 1H), 6.93 (m, 2H), 7.00 (m, 2H), 7.19 (m, 1H), 7.32 (d, 1H), 7.44 (d, 1H), 7.52 (d, 1H), 7.72 (m, 4H), 7.90 (m, 2H), 7.97 (m, 2H), 8.27 (d, 2H), 8.34 (d, 1H), 8.98 (m, 2H); HRMS (MALDI): m/z 801.2710 (100) {M}+.

Example 17

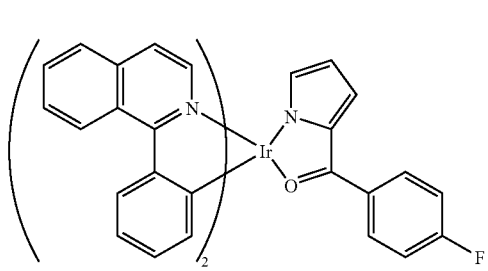

XXXI

Iridium Complex XXXI: 2-(4-Fluorobenzoyl)-pyrrole (73.0 mg, 0.385 mmol) was converted to cyclometallated ketopyrrole complex XXXI as in Example 11. Yield (228 mg, 97%). $^1$H NMR (400 MHz, CD$_2$Cl$_2$, 25° C.) δ6.32 (m, 1H), 6.42 (m, 2H), 6.54 (t, 1H), 6.73 (m, 1H), 6.79 (m, 1H), 7.02 (m, 2H), 7.12 (m, 2H), 7.17 (m, 1H), 7.33 (d, 1H), 7.44 (d, 1H), 7.53 (d, 1H), 7.73 (m, 4H), 7.88 (m, 2H), 7.98 (m, 2H), 8.27 (m, 2H), 8.32 (d, 1H), 8.99 (m, 2H); HRMS (MALDI): m/z 789.2371 (100) {M}+.

Example 18

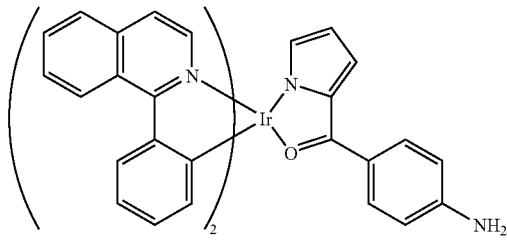

XXXII

Iridium Complex XXXII: To a stirred solution of N-toluenesulfonyl-2-(4-trifluoroacetylamino)benzoyl)pyrrole (352 mg, 0.806 mmol) in 2-methoxyethanol (4 mL) was added solid sodium hydride (50.0 mg, 2.08 mmol) and the solution was stirred for 5 minutes. The bridged dimer intermediate {(piq)$_2$Ir(μ-Cl)}$_2$ (420 mg, 0.322 mmol) was then added and the mixture was heated at 80° C. for 4 hrs. The dark red reaction mixture was cooled to room temperature and concentrated to dryness. The product was chromatographed on silica (EtOAc:Hexanes). Yield (355 mg, 69%). $^1$H NMR (400 MHz, CD$_2$Cl$_2$, 25° C.) δ4.08 (bs, 2H), 6.28 (m, 1H), 6.41 (m, 3H), 6.65 (d, 2H), 6.72 (m, 1H), 6.78 (m, 1H), 7.00 (m, 2H), 7.19 (m, 1H), 7.31 (d, 1H), 7.42 (d, 1H), 7.50 (d, 1H), 7.71 (m, 4H), 7.87 (m, 4H), 8.27 (d, 2H), 8.33 (d, 1H), 8.98 (m, 2H); HRMS (MALDI): m/z 786.1066 (100) {M}+.

Example 19

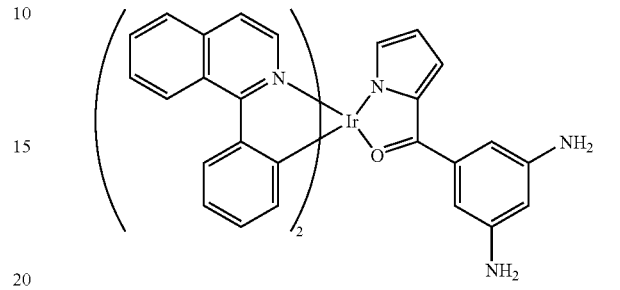

XXXIII

Iridium Complex XXXIII: N-Toluenesulfonyl-2-(3,5-di (trifluoroacetylamino)benzoyl)-pyrrole (211 mg, 0.385 mmol) was converted to cyclometallated ketopyrrole complex XXXIII as in Example 18. Yield (115 mg, 70%). $^1$H NMR (400 MHz, CD$_2$Cl$_2$, 25° C.) δ3.68 (bs, 4H), 6.11 (t, 1H), 6.29 (m, 1H), 6.43 (m, 2H), 6.51 (t, 1H), 6.63 (d, 2H), 6.74 (m, 2H), 7.00 (m, 2H), 7.22 (d, 1H), 7.33 (d, 1H), 7.45 (d, 1H), 7.50 (d, 1H), 7.73 (m, 4H), 7.89 (m, 2H), 8.29 (m, 3H), 8.98 (m, 2H); HRMS (MALDI): m/z 801.1026 (100) {M}+.

Example 20

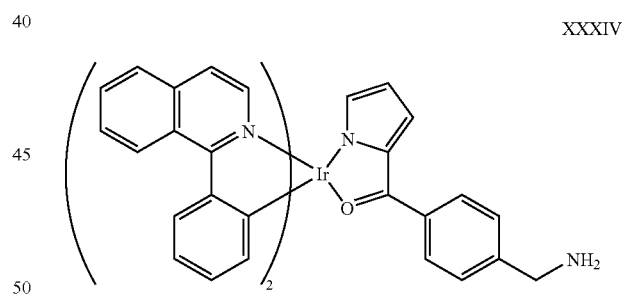

XXXIV

Iridium complex XXXIV: To a stirred solution of 2-(4-aminomethylbenzoyl)pyrrole (106 mg, 0.522 mmol) in DMF (4 mL) was added potassium carbonate (62.0 mg, 2.61 mmol) and the yellow solution was stirred for 5 minutes. The chloride-bridged iridium dimer {(piq)$_2$Ir(μ-Cl)}$_2$ (271 mg, 0.208 mmol) was then added and the mixture was then heated at 70° C. for 1.5 hrs. The dark red reaction mixture was cooled to room temperature and poured into H$_2$O (50 mL) causing the product to precipitate. The product was collected by filtration, washed with H$_2$O, and dried in air and chromatographed on silica (MeOH:CH$_2$Cl$_2$). Yield (178 mg, 73%). $^1$H NMR (400 MHz, CD$_2$Cl$_2$, 25° C.) δ3.89 (bs, 2H), 6.31 (m, 1H), 6.42 (m, 1H), 6.45 (m, 1H), 6.53 (t, 1H), 6.73 (m, 1H), 6.79 (m, 1H), 7.01 (m, 2H), 7.20 (m, 1H), 7.32 (d, 1H), 7.37 (d, 2H), 7.44 (d, 1H), 7.53 (d, 1H), 7.72 (m, 4H), 7.89 (m, 4H), 8.28 (d, 2H), 8.35 (d, 1H), 8.99 (m, 2H); HRMS (MALDI): m/z 800.0403 (100) {M}$^+$.

Example 21

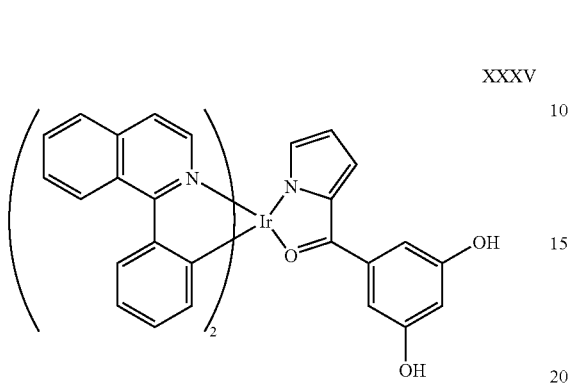

Iridium Complex XXXV: 2-(3,5-Dihydroxybenzoyl)-pyrrole (106 mg, 0.522 mmol) was treated at ambient temperature in 2-methoxyethanol (4 mL) with sodium hydride (62.0 mg, 2.61 mmol) and the resultant yellow solution was stirred for 5 minutes. The chloride-bridged cyclometallated iridium dimer intermediate, {(piq)$_2$Ir(μ-Cl)}$_2$(271 mg, 0.208 mmol), was added and the mixture was then heated at 70° C. for 1.5 hrs. The dark red reaction mixture was cooled to room temperature and concentrated to dryness. The product cyclometallated ketopyrrole complex XXXV was chromatographed on silica (MeOH:CH$_2$Cl$_2$, 2:98). Yield (282 mg, 84%). $^1$H NMR (400 MHz, CD$_2$Cl$_2$, 25° C.) δ5.21 (bs, 2H), 6.31 (m, 1H), 6.41 (m, 3H), 6.55 (t, 1H), 6.76 (m, 2H), 6.95 (d, 2H) 7.01 (m, 2H), 7.21 (d, 1H), 7.30 (d, 1H), 7.41 (d, 1H), 7.51 (d, 1H), 7.73 (m, 4H), 7.89 (m, 2H), 8.28 (m, 3H), 8.98 (m, 2H); HRMS (MALDI): m/z 803.0823 (100) {M}$^+$.

Example 22

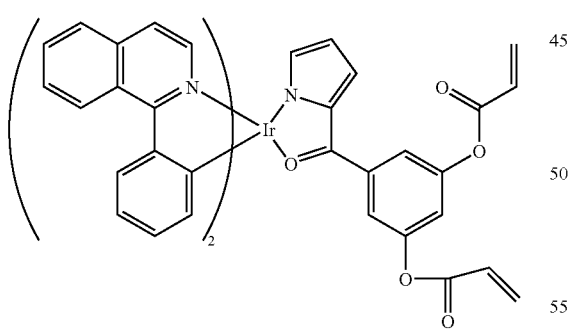

Iridium Complex XXXVI: To a stirred suspension of iridium complex XXXV (79 mg, 0.098 mmol) in CH$_2$Cl$_2$ (4 mL) was added triethylamine (100 μL, 0.72 mmol). To the resultant homogenous solution was added acryloyl chloride (100 μL, 1.2 mmol) and the reaction mixture was stirred for 1 hour at room temperature. Thereafter the dark red reaction mixture was concentrated to dryness. The crude product was chromatographed on silica gel using CH$_2$Cl$_2$ as the eluant. Yield (68 mg, 76%). $^1$H NMR (400 MHz, CD$_2$Cl$_2$, 25° C.) δ6.02 (m, 2H), 6.27 (d, 1H), 6.31 (d, 1H), 6.35 (m, 1H), 6.41 (m, 2H), 6.56 (m, 2H), 6.60 (d, 1H), 6.73 (m, 1H), 6.78 (m, 1H), 7.00 (m, 2H), 7.13 (t, 1H), 7.26 (m, 1H), 7.33 (d, 1H), 7.46 (d, 1H), 7.52 (d, 1H), 7.66 (d, 2H), 7.74 (m, 4H), 7.90 (m, 2H), 8.27 (d, 2H), 8.31 (d, 1H), 8.98 (m, 2H); HRMS (MALDI): m/z 911.1887 (100) {M}$^+$.

Example 23

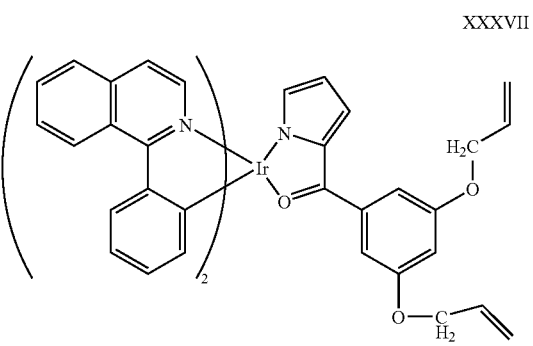

Iridium Complex XXXVII: To a solution of iridium complex XXXV (100 mg, 0.492 mmol) in DMF (2.0 mL) were added successively potassium carbonate (272 mg, 1.97 mmol) and allyl bromide (238 mg, 1.97 mmol) at room temperature. The mixture was stirred for 24 h, poured into water, and then extracted with Et$_2$O. The extract was washed with brine, dried over Mg$_2$SO$_4$, and concentrated to dryness. The resulting residue was chromatographed on silica gel (CH$_2$Cl$_2$) to give the product diallyl ether XXXVII as a colorless oil. Yield (123 mg, 88%). $^1$H NMR (400 MHz, CD$_2$Cl$_2$, 25° C.) δ 4.58 (m, 4H), 5.30 (m, 2H), 5.43 (m, 2H), 6.08 (m, 2H), 6.34 (m, 1H), 6.70 (t, 1H), 6.92 (m, 1H), 7.03 (d, 2H), 7.17 (m, 1H), 9.83 (bs, 1H); $^{13}$C NMR (100 MHz, CD$_2$Cl$_2$, 25° C.) δ69.7, 106.1, 108.2, 111.5, 118.0, 119.7, 125.9, 131.6, 133.7, 140.8, 160.2, 184.4; HRMS (EI): m/z 283.1179 (100) {M}$^+$.

Example 24

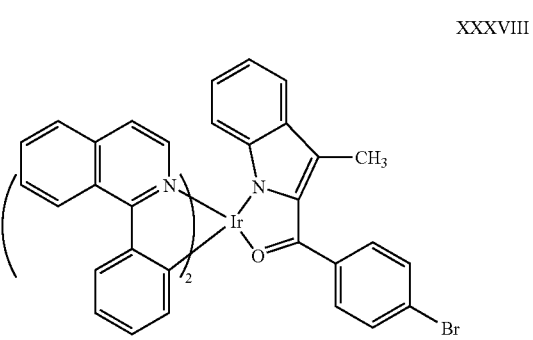

Iridium complex XXXVIII: To a stirred solution of 2-(4-bromobenzoyl)-3-methylindole (100 mg, 0.323 mmol) in 2-methoxyethanol (4 mL) was added solid sodium hydride (40.0 mg, 1.67 mmol) and the mixture was stirred for 5 minutes. {(piq)$_2$Ir(μ-Cl)}$_2$(191 mg, 0.147 mmol) was then added and the reaction mixture was then heated at 70° C. for 1.5 hrs. The dark red reaction mixture was cooled to room temperature and poured into MeOH/H$_2$O (125 mL/10 mL)

and brought to a gentle reflux causing the product to precipitate. The product was collected by filtration, washed with MeOH, and dried in air. Yield (258 mg, 98%). $^1$H NMR (400 MHz, CD$_2$Cl$_2$, 25° C.) δ6.32 (d, 1H), 6.42 (m, 2H), 6.55 (t, 1H), 6.70 (m, 1H), 6.79 (m, 1H) 7.01 (m, 2H), 7.18 (d, 1H), 7.83 (d, 1H), 7.44 (d, 1H), 7.56 (d, 2H), 7.73 (m, 4H), 7.83 (d, 2H), 7.87 (m, 1H), 7.93 (m, 1H), 8.27 (d, 2H), 8.31 (d, 1H), 9.98 (m, 2H); HRMS (MALDI): m/z 913.1481 (100) {M}$^+$.

Example 25

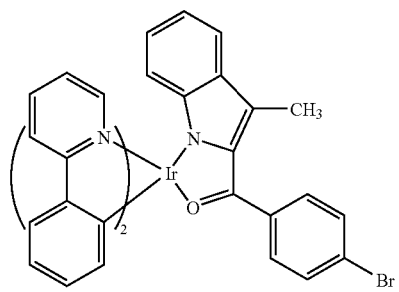

XXXIX

Iridium complex XXXIX: To a stirred solution of 2-(4-bromobenzoyl)-3-methylindole (132 mg, 0.440 mmol) in 2-methoxyethanol (4 mL) was added solid sodium hydride (40.0 mg, 1.67 mmol). After stirring for 5 minutes, {(ppy)$_2$Ir(μ-Cl)}$_2$ (220 mg, 0.199 mmol) was added and the mixture was then heated at 70° C. for 1.5 hrs. The dark red reaction mixture was cooled to room temperature and poured into MeOH/H$_2$O (150 mL/20 mL) causing the product to precipitate. The product was collected by filtration, washed with MeOH, and dried in air. Yield (278 mg, 98%). $^1$H NMR (400 MHz, CD$_2$Cl$_2$, 25° C.) δ6.32 (d, 1H), 6.42 (m, 2H), 6.55 (t, 1H), 6.70 (m, 1H), 6.79 (m, 1H) 7.01 (m, 2H), 7.18 (d, 1H), 7.83 (d, 1H), 7.44 (d, 1H), 7.56 (d, 2H), 7.73 (m, 4H), 7.83 (d, 2H), 7.87 (m, 1H), 7.93 (m, 1H), 8.27 (d, 2H), 8.31 (d, 1H), 9.98 (m, 2H); HRMS (MALDI): m/z 813.1268 (100) {M}$^+$.

Example 26

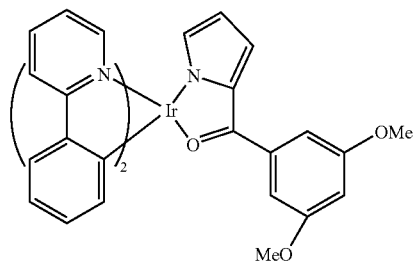

XL

Iridium complex XL: To a stirred solution of 2-(3,5-dimethoxybenzoyl)pyrrole (85.0 mg, 0.367 mmol) in 2-methoxyethanol (4 mL) was added solid sodium hydride (40.0 mg, 1.67 mmol). The mixture was stirred for 5 minutes and {(ppy)$_2$Ir(μ-Cl)}$_2$ (184 mg, 0.167 mmol) was added and the mixture was then heated at 70° C. for 1 h. The orange reaction mixture was cooled to room temperature and concentrated to dryness. The product ketopyrrole complex XL was chromatographed on silica (CH$_2$Cl$_2$). Yield (230 mg, 94%). $^1$H NMR (400 MHz, CD$_2$Cl$_2$, 25° C.) δ3.81 (s, 6H), 6.34 (m, 3H), 6.61 (m, 2H), 6.76 (m, 1H), 6.83 (m, 1H), 6.94 (m, 3H) 7.05 (d, 2H), 7.10 (m, 1H), 7.18 (d, 1H), 7.65 (m, 5H), 7.88 (d, 2H), 8.40 (d, 1H); HRMS (MALDI): m/z 730.9544 (100) {M}$^+$ Example 27

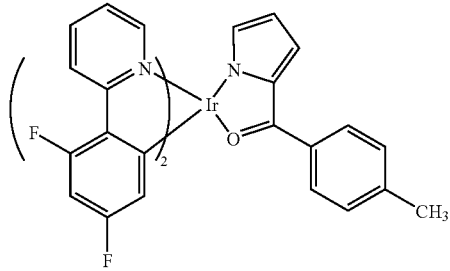

XLI

Iridium complex XLI: To a stirred 2-methoxyethanol solution (4 mL) containing 2-(4-methylbenzoyl)pyrrole (50.0 mg, 0.270 mmol) was added solid sodium hydride (13.0 mg, 0.540 mmol) resulting in a yellow solution that was stirred for 5 min. The chloride-bridged cyclometallated iridium dimer intermediate {(F$_2$ppy)$_2$Ir(μ-Cl)} 2 (153 mg, 0.123 mmol) was then added and the mixture was heated at 80° C. for 1.5 hrs. The yellow reaction mixture was cooled to room temperature and concentrated to dryness. The product cyclometallated ketopyrrole complex XLI was chromatographed on silica (Hexanes:CH$_2$Cl$_2$, 2:1) and recrystallized from hexanes: CH$_2$Cl$_2$. Yield (120 mg, 65%). $^1$H NMR (400 MHz, CD$_2$Cl$_2$, 25° C.) δ2.41 (s, 3H), 5.80 (m, 1H), 5.82 (t, 1H), 6.36 (m, 1H), 6.46 (m, 2H), 6.67 (t, 1H), 7.01 (m, 1H), 7.12 (m, 1H), 7.20 (m, 1H), 7.27 (d, 2H), 7.53 (m, 1H), 7.74 (m, 2H), 7.83 (d, 2H), 8.25 (m, 2H), 8.36 (m, 1H); HRMS (MALDI): m/z 757.1597 (100) {M}$^+$.

Example 28

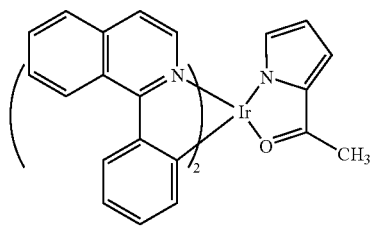

XLII

Iridium Complex XLII: 2-acetylpyrrole (42 mg, 0.385 mmol) was converted to cyclometallated ketopyrrole complex XLII as in Example 11. Yield (201 mg, 92%). $^1$H NMR (400 MHz, CD$_2$Cl$_2$, 25° C.) δ2.52 (s, 3H), 6.21 (m, 1H), 6.39 (m, 2H), 6.45 (t, 1H), 6.70 (m, 1H), 6.77 (m, 1H), 6.99 (m, 2H), 7.10 (m, 1H), 7.33 (d, 1H), 7.45 (d, 1H), 7.48 (d, 1H), 7.73 (m, 4H), 7.90 (m, 2H), 8.26 (m, 3H), 8.95 (m, 2H); HRMS (MALDI): m/z 709.0687 (100) {M}+.

Example 29

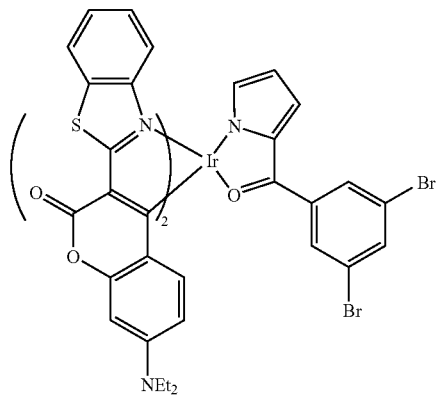

XLIII

Iridium Complex XLIII: To a stirred 2-methoxyethanol solution (2 mL) containing 2-(3,5-dibromobenzoyl)-pyrrole (139 mg, 0.356 mmol) was added solid sodium hydride (40.0 mg, 1.67 mmol) and the resultant yellow solution was stirred for 5 minutes. The chloride-bridged cyclometallated iridium dimer intermediate {(C6)$_2$Ir(μ-Cl)}$_2$(265 mg, 0.142 mmol) was then added and the mixture was then heated at 80° C. for 3 hrs. The reaction mixture was cooled to room temperature and poured into MeOH (150 mL) causing the product to precipitate. The product cyclometallated ketopyrrole complex XLIII was collected by filtration and washed with methanol. The product was chromatographed through silica (CH$_2$Cl$_2$). Yield (214 mg, 65%). $^1$H NMR (400 MHz, CD$_2$Cl$_2$, 25° C.) δ2.41 (s, 3H), 5.80 (m, 1H), 5.82 (t, 1H), 6.36 (m, 1H), 6.46 (m, 2H), 6.67 (t, 1H), 7.01 (m, 1H), 7.12 (m, 1H), 7.20 (m, 1H), 7.27 (d, 2H), 7.53 (m, 1H), 7.74 (m, 2H), 7.83 (d, 2H), 8.25 (m, 2H), 8.36 (m, 1H); HRMS (MALDI): m/z 1220.0184 (100) {M, M+H}+.

Example 30

XLIV

Iridium complex XLIV: 2-(4-Fluorobenzoyl)-pyrrole (25.0 mg, 0.13 mmol) was converted to cyclometallated ketopyrrole complex XLIV via a procedure analogous to the procedure described in Example 29. Yield (78 mg, 65%). $^1$H NMR (400 MHz, CD$_2$Cl$_2$, 25° C.) δ2.41 (s, 3H), 5.80 (m, 1H), 5.82 (t, 1H), 6.36 (m, 1H), 6.46 (m, 2H), 6.67 (t, 1H), 7.01 (m, 1H), 7.12 (m, 1H), 7.20 (m, 1H), 7.27 (d, 2H), 7.53 (m, 1H), 7.74 (m, 2H), 7.83 (d, 2H), 8.25 (m, 2H), 8.36 (m, 1H); HRMS (MALDI): m/z 1080.1628 (100) (M, M+H)+.

Preparation of Polymeric Organic Iridium Complexes

Example 31

XLV

Bisphenol A—Iridium Complex Co-Polycarbonate XLV: To a stirred solution of bisphenol A bischloroformate (0.500 g, 1.42 mmol), bisphenol A (BPA) (0.323 g, 1.42 mmol), and iridium complex XXXV (28.8 mg, 0.0359 mmol) in methylene chloride (CH$_2$Cl$_2$, 25 mL) 0° C. under a nitrogen atmosphere was added triethylamine (0.359 mg, 3.55 mmol). The mixture was maintained at 0° C. and stirred for 1 hr. The reaction mixture was then allowed to warm to room temperature and stirring was continued for an additional hour. The mixture was then diluted with CH$_2$Cl$_2$(25 mL) and transferred to a flask containing 10% NaHCO$_3$(50 mL) and stirred for 10 min. The resultant two-phase mixture was transferred to a separatory funnel and the aqueous layer was separated and discarded. The organic phase was washed with 5% HCl (2×50 mL), then with H$_2$O (2×50 mL), concentrated to a volume of about 15 mL, and added to MeOH (100 mL) to precipitate the product co-polycarbonate. The product was collected by filtration and then redissolved in CH$_2$Cl$_2$(25 mL) and isolated by dropwise addition to rapidly stirred, boiling H$_2$O (300 mL). The product co-polycarbonate was collected by filtration, dried in air, and again dissolved in CH$_2$Cl$_2$(25 mL) and precipitated from MeOH. The product co-polycarbonate was dried and analyzed by gel permeation chromatography (relative to polystyrene standards): M$_w$=108,000 grams per mole, M$_w$=30,000 grams per mole, M$_w$/M$_n$=3.60.

Example 32

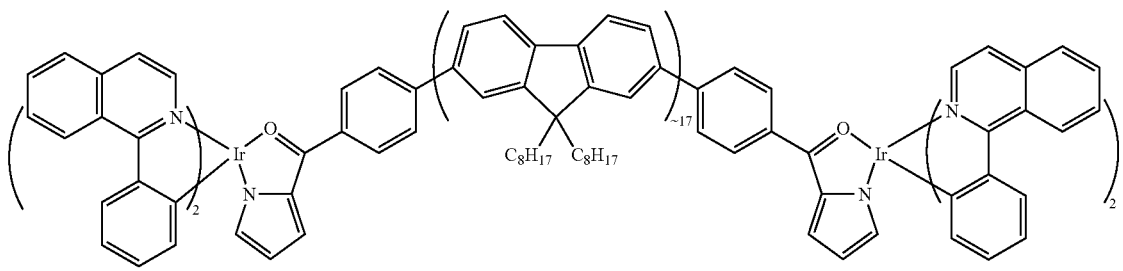

Poly(9,9-diocylfluorene) End-capped Organic Iridium Complex XLVI: A solution of 2,7-dibromo-9,9-dioctylfluorene, 537 mg (0.98 mmol), 9,9-dioctylflouren-2,7-diyl-bist-rimethyleneborate (558 mg, 1.00 mmol, CAS No. 317802-08-7) and tri-o-tolylphosphine (30.4 mg, 0.1 mmol) in toluene (25 mL) was degassed with argon for 10 minutes. Pd(OAc)$_2$(6.7 mg, 0.03 mmol) and tetraethylammonium hydroxide (2.2 mL of a 20% aqueous solution, 3.0 mmol) were then added and the resultant mixture was degassed for an additional 5-10 minutes. The mixture was then immersed in an oil bath at 80° C. and stirred under a positive nitrogen pressure for 3 hours. Organic iridium complex XXVI, 34 mg (0.04 mmol) was added and heating was continued for an additional 18 hours. The reaction mixture was stirred at ambient temperature with 20 mL 0.1N HCl and then filtered through CELITE. The organic phase was diluted with toluene (15-20 mL), washed with water (2×25 mL), saturated NaCl (1×25 mL) and then passed through a filter containing a layer of amine-functionalized silica gel and CELITE. The filtrate was concentrated on a rotary evaporator and the product polymeric organic iridium complex XLVI was isolated by precipitation into 5 volumes of methanol. The salmon colored polymer was redissolved in CH$_2$Cl$_2$ and reprecipitated into methanol. Solids were then stirred in a mixture of water and methanol (~9/1), collected and stirred with methanol for 2 hrs. The iridium complex end-capped polyfluorene XLVI was collected by filtration and dried in a vacuum oven. Gel permeation chromatographic analysis indicates Mw=21076 and Mw/Mn=2.68.

Example 33

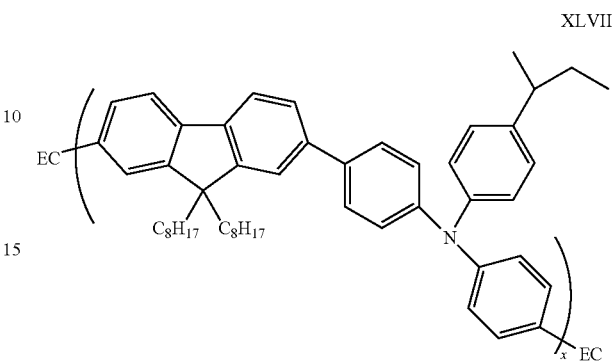

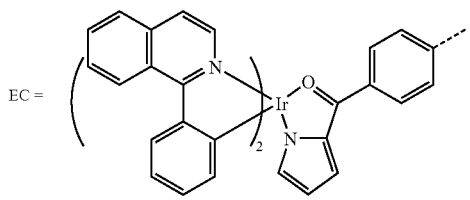

Poly(9,9-diocylfluorene-triarylamine) End-capped Organic Iridium Complex XLVII: A solution of N,N-4,4'-dibromophenyl-N-4-2-butylphenylamine, 278 mg (0.605 mmol), 9,9-dioctyl-2,7-bis-dimethyleneborate, 327 mg (0.6175 mmol), and tri-o-tolylphosphine, 18.7 mg (0.0617 mmol) in toluene (15 ml) was degassed with argon for 10 minutes then Pd(OAc)$_2$, 4.2 mg (0.0185 mmol) and tetraethylammonium hydroxide, 1.4 ml of a 20% aqueous solution (1.9 mmol) was added and degassing was continued for an additional 5-10 minutes. The mixture was immersed in an 70° C. oil bath and stirred under a positive nitrogen pressure for 2 hours at which point the iridium complex, XXVI {(piq)Ir (L$_A$), where L$_A$ is the ancillary ligand derived from 2-(4-bromobenzoyl)pyrrole}, 21 mg (0.0247 mmol) was added.

Heating was continued for an additional 18 hr and the cooled mixture was stirred with 20 ml of 0.1N HCl then filtered through Celite. The organic phase was diluted with toluene (15-20 ml), washed with water (2×25 ml) and saturated NaCl (1×25 ml) then passed through a filter containing a layer of amine-functional silica gel and Celite. The solution was concentrated on a rotary evaporator and the polymer was isolated by precipitation into 5 volumes of methanol. The salmon colored polymer was redissolved in $CH_2Cl_2$ and reprecipitated into methanol. Solids were then stirred in a mixture of water and methanol (~9/1), collected and stirred with methanol for 2 hrs. The final polymer was collected by filtration and dried in a vacuum oven. The yield was 279 mg (63.5%). Gel permeation chromatographic analysis indicates Mw=28747 grams per mole and Mw/Mn=2.05. $^1$H NMR ($CDCl_3$) δ7.78-7.22 (m, 18, Ar—H), 2.65 (t, 1, methine-CH), 2.0 (br s, 4, —$CH_2$'s) and 1.52-0.82 ppm ((m, 38 t, aliphatics). Signals for the complex were undetectable. UV ($CH_2Cl_2$) λ max=388 nm.

TABLE 21

Data for polymeric organic iridium complex XLVII of Example 33

| Mw (× $10^{-3}$) | Mn (× $10^{-3}$) | Mw/Mn |
|---|---|---|
| 28.7 | 14.0 | 2.1 |

Example 34

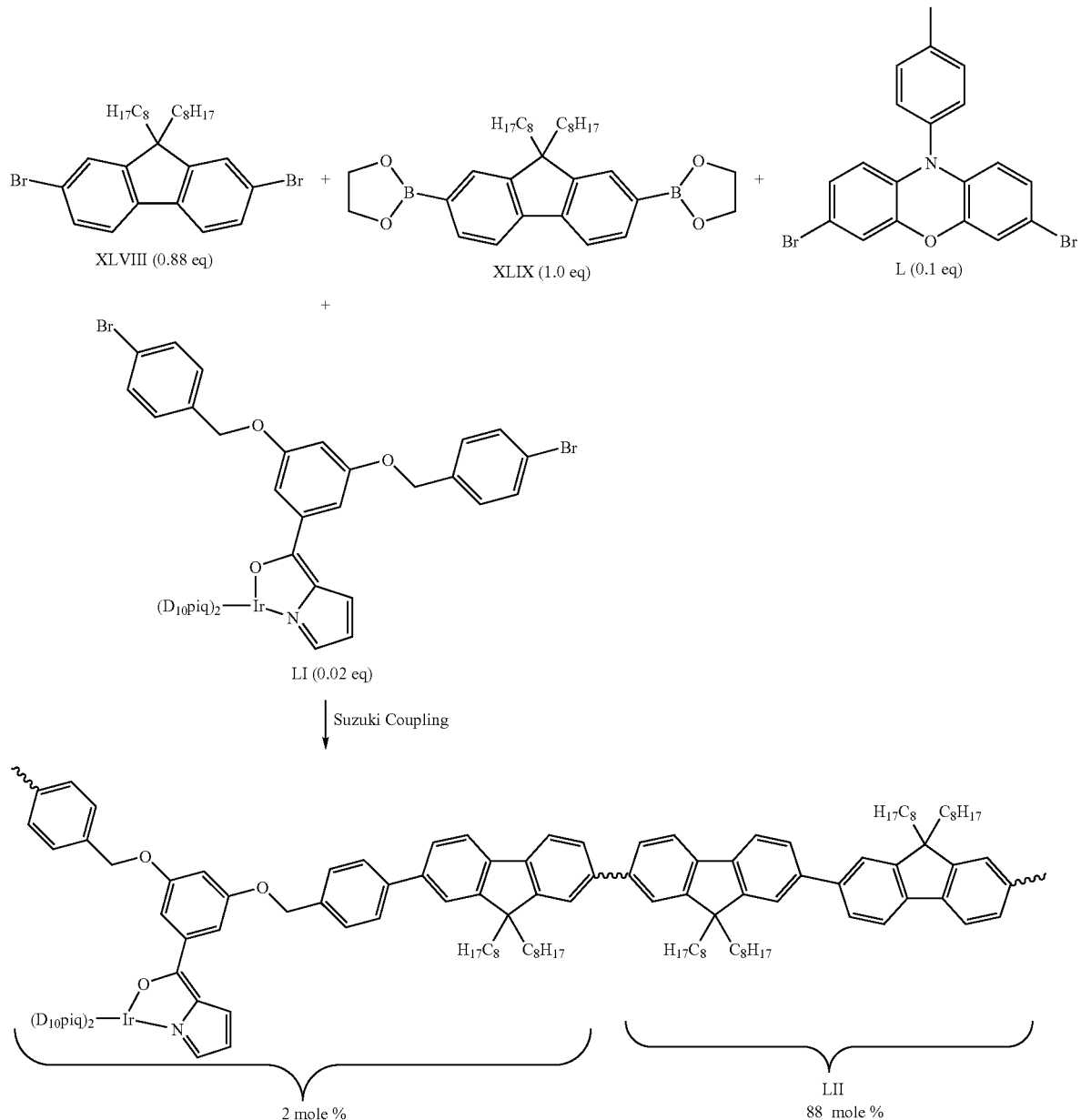

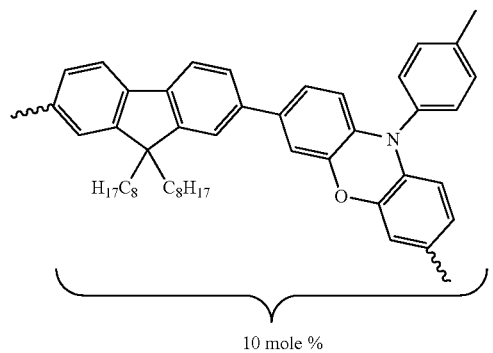

10 mole %

Deuterated Polymeric Organic Iridium Complex LII: A solution of dibromide, XLVIII, 482 mg (0.88 mmol), bisborate XLIX, 530 mg (1.0 mmol), arylphenoxazine dibromide, XL, 43 mg (0.1 mmol) and tris-o-tolylphosphine, 32 mg mmol) in toluene (20 ml) was degassed with argon for 15 minutes then Pd(OAc)$_2$, 7.0 mg (0.031 mmol) and Et$_4$NOH, 3.7 g of a degassed 20% aqueous solution (5.0 mmol) and water, 4 ml, were added. Degassing was continued for an additional 5 minutes then the argon tube was replaced with a positive nitrogen pressure, the flask was immersed in an 70° C. oil bath. After 20 minutes, deuterated organic iridium complex, LI (incorporating 2 cyclometallated ligands derived from perdeutero 1-phenylisoquinoline), 23 mg (0.02 mmol) was added and stirring under nitrogen was continued for 18 hours. (Organic iridium complex LI was prepared as described in Example 53 below). The cooled mixture was diluted with toluene (10 ml) and stirred with 0.1N HCl (25 ml) for 30 minutes. This mixture was filtered through Celite and the organic phase was washed with 2×25 ml of water and 1×25 ml of saturated NaCl. After filtration through layers of amine-functional silica gel and Celite, the solution was concentrated to about 10% solids using a rotary evaporator. The residue was precipitated into methanol (5-10 volumes). Collected solids were redissolved in CH$_2$Cl$_2$ and reprecipitated into (1/1 v/v) methanol/acetone. The collected solids were boiled with a water/methanol mixture (9/1), collected and stirred with acetone then methanol. The final polymer was dried overnight in a vacuum oven at 60° C. to afford 648 mg (84%) of a salmon-colored polymer. Molecular weight (GPC): 90,278, (Mw) Mw/Mn=3.02) UV (CH$_2$Cl$_2$) $\lambda_{max}$32 391 nm; $^1$H NMR (CD$_2$Cl$_2$) δ8.0-7.8 (m, ~12, ArH), 2.20 (s, br, 8, Ar—CH$_2$) and 1.2-0.8 ppm (m, ~58, aliphatics). For convenience, the product polymeric organic iridium complex is represented as structure LII. Here, and throughout this disclosure, the mole percentages of the various structural units comprising the polymers is nominal and is based upon the relative amounts of reactants employed to prepare the polymer.

Examples 35-37

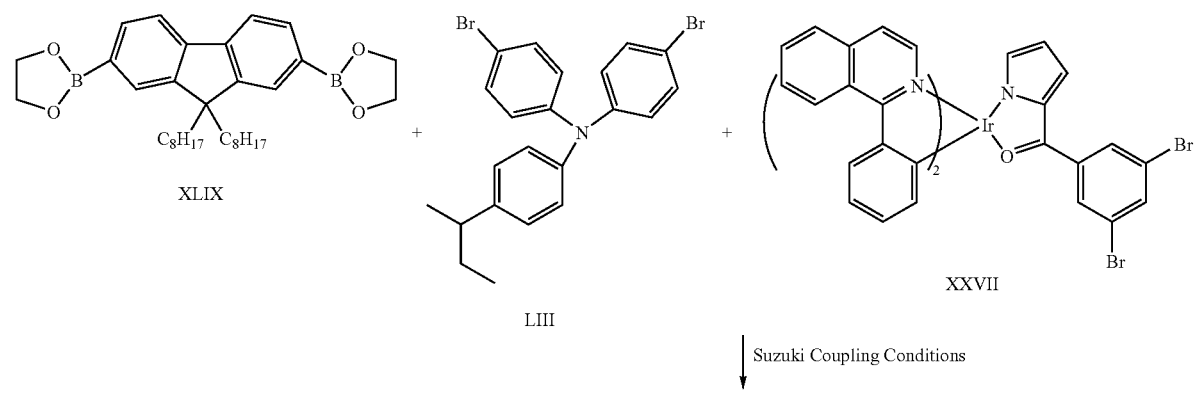

Suzuki Coupling Conditions

-continued

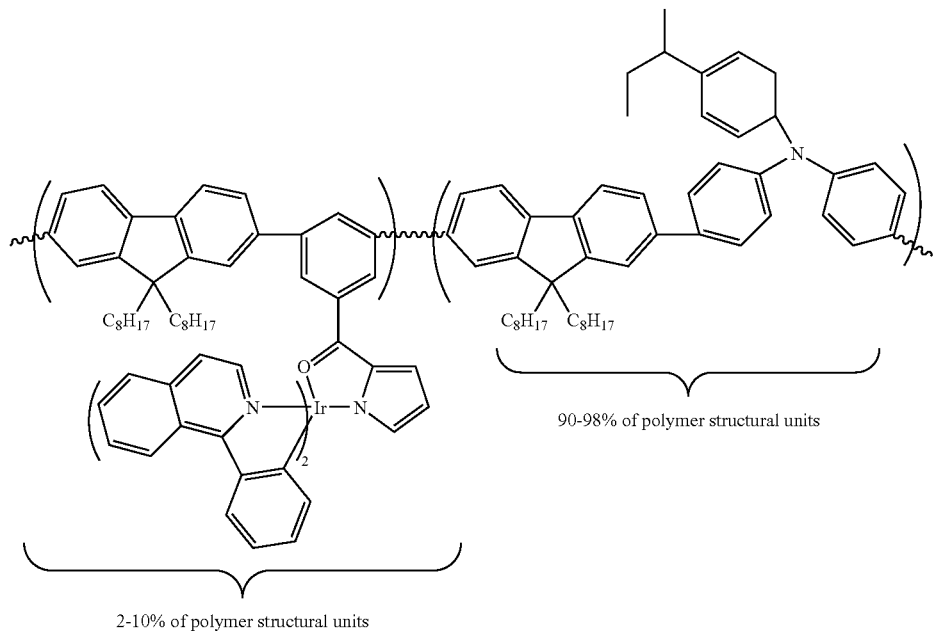

LIV, LV, and LVI

Co-polyfluorene-triarylamine electroluminescent materials comprising organic iridium groups on the polymer main chain were prepared as described in the following general procedure. Molecular weight data for the polymeric organic iridium complexes LIV, LV, and LVI are gathered in Table 22.

A solution of bis-borate compound XLIX, triarylamine dibromide LIII, iridium complex XXVII, and tris-o-tolylphosphine in toluene (12 mL) was degassed with argon via an argon inlet tube for 15 minutes. Pd(OAc)$_2$ (3.4 mg, 0.015 mmol) and Et$_4$NOH (1.0 mL of a degassed 20% aqueous solution, 1.36 mmol) were then added and degassing was continued for an additional 5 minutes. The reaction flask was then placed under a positive nitrogen pressure, immersed in an 80° C. oil bath and the reaction mixture was stirred at 80° C. for 18 hours. The reaction mixture then was diluted with toluene (10 mL) and stirred with 0.1N HCl (25 mL) for 30 minutes. This mixture was filtered through CELITE and the organic phase was washed with 2×25 mL of water and 1×25 mL of saturated NaCl. After filtration through layers of amine-functional silica gel and CELITE, the solution was concentrated to about 10% solids using a rotary evaporator. The residue was precipitated into methanol (5-10 volumes). Collected solids were redissolved in CH$_2$Cl$_2$ and reprecipitated into methanol. The collected solids were boiled with a water/methanol mixture (9/1), collected and stirred with acetone then methanol. The purified product polymer (LIV, LV, or LVI) was dried overnight in a vacuum oven at 60° C.

TABLE 22

Polymeric Organic Iridium Complexes Comprising Co-Polyfluorene-Triarylamine Structural Units

| Example # | Structure # | Molar Ratio of Structural Groups Derived From Organic Iridium Complex XXVII Structural Groups Derived From Triarylamine Dibromide LIII | Mw (× 10$^{-3}$) | Mn (× 10$^{-3}$) | Mw/Mn |
|---|---|---|---|---|---|
| 35 | LIV | 4:96 | 48.7 | 23.3 | 2.1 |
| 36 | LV | 2:98 | 53 | 9.5 | 5.7 |
| 37 | LVI | 10:90 | 41.4 | 24.6 | 1.7 |

Preparation of Deuterated Organic Iridium Complexes

Example 38

D$_7$-Isoquinoline-N-oxide: A mixture of D$_7$-isoquinoline (2.50 g, 18.4 mmol) (C/D/N Isotopes Inc.), 7.5 mL of glacial acetic acid, and 4.5 mL of 30% hydrogen peroxide was heated at reflux for 2.5 h. The mixture was then concentrated under reduced pressure and the yellow residue was dissolved in CHCl$_3$ and treated with excess of K$_2$CO$_3$. Water was added to form a thick paste with the carbonate. The mixture was filtered after the cessation of effervescence and the solid paste was washed with CHCl$_3$. The CHCl$_3$ solution was dried over K$_2$CO$_3$, filtered and concentrated to dryness to give a yellow-orange oil. The oil was dissolved in EtOAc (10 mL) and the solvent was cautiously removed on a rotary evaporator (without a water bath) until the product solidified. The solid product was suspended in hexanes and collected by vacuum filtration and dried in air. Yield: 2.50 g, 89%. $^1$H NMR (400 MHz, $CD_2Cl_2$, 25° C.) δ7.56 (bs), 7.60 (bs), 7.66 (bs), 7.70 (bs), 7.79 (bs), 8.06 (bs), 8.70 (bs). It is estimated that the product was 97.5% deuterated.

Example 39

$D_6$-2-Chloroisoquinoline: To a $CD_2Cl_2$ solution of $D_7$-isoquinoline-N-oxide (2.50 g, 16.4 mmol) was added dropwise $POCl_3$ (5.0 mL, 53.5 mmol) at such a rate as to maintain a gentle reflux and then the reaction mixture was heated at reflux for 2 h. The reaction mixture was then cooled and added dropwise to a rapidly stirred biphasic mixture of $NaHCO_3$ (20g) in 50 mL and $Et_2O$ (100 mL). After the cessation of effervescence the layers were separated and the aqueous phase was extracted with ether (3×100 mL). The combined organic extracts were dried over $MgSO_4$ and decolorized with charcoal. The solvents were removed to afford a mixture of deuterated 2-chloroisoquinoline and isoquinoline as a yellow oil. The product was carried on to the next step (See Example 40) without further purification. Yield: 2.00 g, 72%. $^1$H NMR (400 MHz, $CD_2Cl_2$, 25° C.) δ7.64 (bs), 7.71 (bs), 7.77 (bs), 7.85 (bs), 7.88 (bs), 8.20 (bs), 8.25 (bs).

Example 40

$D_5$-Phenylboronic acid: A dry three-neck flask equipped with a rubber septum, an addition funnel equipped with a rubber septum, and a condenser was charged under nitrogen with magnesium turnings. To the addition funnel was added $D_5$-bromobenzene (6.5 mL, 62 mmol) (Aldrich) dissolved in a 1:1 mixture of THF/toluene (31 mL). Grignard reagent formation was observed after about after about 1 mL of the contents of the addition funnel had been added to the magnesium turnings. The remaining bromobenzene solution was added dropwise over a period of about 1 h. After the addition was complete the reaction mixture was heated at 70° C. for 1 h. The reaction mixture was cooled to room temperature and added via a canulating needled to an addition funnel on a second three-neck flask containing a solution of triethylborate $(B(OEt)_3)$ (10.5 mL, 62 mmol) in toluene (10 mL) maintained at 0° C. The solution of the freshly prepared Grignard reagent was then added dropwise to the solution of triethylborate over a period of 1 h. The cooling bath was then removed and the reaction mixture was allowed to stir at room temperature for 15 h. The reaction mixture was quenched with 10% $H_2SO_4$ (30 mL) and stirred at room temperature for 1 h. The layers were separated and the organic layer was dried over $Na_2SO_4$. After removal of the solvents, hexanes were added to precipitate the product as an off-white solid which was collected by filtration and dried. Yield: 3.50 g, 45%. $^1$H NMR (400 MHz, $CD_2Cl_2$, 25° C.) δ 6.01 (bs, 2H).

$D_{11}$-2-Phenylisoquinoline: A biphasic mixture of toluene (10 mL), EtOH (5 mL), and 2M $Na_2CO_3$ (10 mL) containing $D_5$-phenylboronic acid (2.40 g, 19.0 mmol) and $D_6$-2-chloroisoquinoline (2.00 g, 11.8 mmol) was purged with $N_2$ for 30 min using a gas diffusion tube. $Pd(PPh_3)_4$ (0.600 g, 0.520 mmol) was then added and the mixture was heated at reflux for 5 h. After cooling to room temperature the product mixture was transferred to a separatory funnel containing $H_2O$ (100 mL) and the layers were separated. The aqueous layer was extracted with EtOAc (2×100 mL) and the combined organic layers were washed with $H_2O$, dried over $Na_2SO_4$, filtered, and concentrated to dryness. The crude product was chromatographed ($SiO_2$EtOAc/Hexanes) to afford the product as a white solid. Yield: 1.50 g, 59%. $^1$H NMR (400 MHz, $CD_2Cl_2$, 25° C.) δ7.34 (bs), 7.35 (bs), 7.55 (bs), 7.67 (bs), 7.71 (bs), 7.92 (bs), 8.11 (bs), 8.21 (bs), 8.59 (bs); HRMS (ESI): m/z 217.1862 (100) {M+H}+(98.5 atom % D).

$((D_{10}$-piq$)_2$Ir(μ-Cl))$_2$: A mixture of 2-methoxyethanol and water (20 ml: 5 mL) was degassed with $N_2$ for 15 min. To this solvent mixture was added $IrCl_3.xH_2O$ (0.94 g, 3.2 mmol) followed by $D_{11}$-2-phenylisoquinoline (1.5 g, 6.9 mmol) and the mixture was heated at reflux for 15 h under an atmosphere of $N_2$. The reaction mixture was cooled to room temperature and the red precipitate was collected by filtration and washed with MeOH until the filtrate washes were colorless and then dried in air. Yield: 1.2 g, 57%. $^1$H NMR (400 MHz, $CD_3SOCD_3$, 25° C.) δ5.56 (s), 6.31 (s), 6.90 (s), 6.92 (s), 6.99 (s), 7.01 (s), 8.00-7.80 (m), 8.12 (m), 8.21 (m), 8.86 (s), 8.92 (s), 9.57 (s), 9.75 (s).

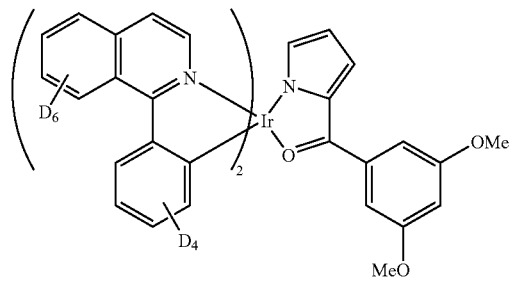

LVII $(D_{10}$-piq$)_2$Ir$(L_4)$ LVII: To a stirred 2-methoxyethanol solution (4 mL) containing the 2-(3,5-dimethoxybenzoyl)pyrrole (37 mg, 0.13 mmol) was added solid sodium hydride (40.0 mg, 1.67 mmol). After letting this solution stir for 5 min, $((D_{10}$-piq$)_2$Ir(μ-Cl))$_2$ (100 mg, 0.0745 mmol) was added and the mixture was then heated at 80° C. for 1.5 hrs. The reaction mixture was cooled to room temperature, poured into MeOH (100 mL). The product precipitated from solution and was collected by vacuum filtration. Yield (115 mg, 65%). $^1$H NMR (400 MHz, $CD_2Cl_2$, 25° C.) δ3.83 (s, 3H), 6.30 (m, 1H), 6.41 (s), 6.44 (s), 6.50 (t, 1H), 6.93 (m, 2H), 7.00 (m), 7.19 (m, 1H), 7.32 (s), 7.44 (s), 7.52 (s), 7.72 (s), 7.73 (s), 7.74 (s), 7.88 (s), 7.92 (s), 7.97 (m, 2H), 8.27 (t), 8.34 (s), 8.98 (m); HRMS (MALDI): m/z 819.2400 (100) {M}+.

Performance Characteristics of Organic Iridium Complexes And Polymeric Organic Iridium Complexes in OLED Devices Example 41

The emissive characteristics of organic iridium complex XXVI were compared to those of dipyrrin complexes LVIII and LIX.

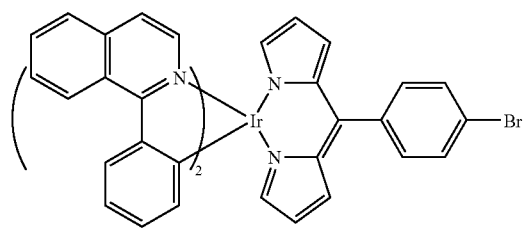

LVIII

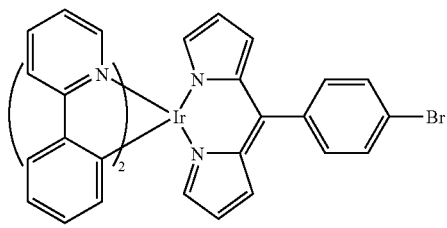

LIX

Initially, dilute solutions of dipyrrin complex LVIII in dichloromethane and organic iridium complex XXVI ((piq)$_2$Ir(L$_A$)) where the ancillary ligand L$_A$ is derived from 2-(4-bromobenzoyl)pyrrole in dichloromethane were prepared. When the solutions were irradiated at 354 nm with a handheld UV lamp, the vial containing the solution containing organic iridium complex XXVI was observed to emit an orange-red color that was substantially brighter than the deep-red color emitted from the solution containing dipyrrin complex LVIII.

Figure 12:
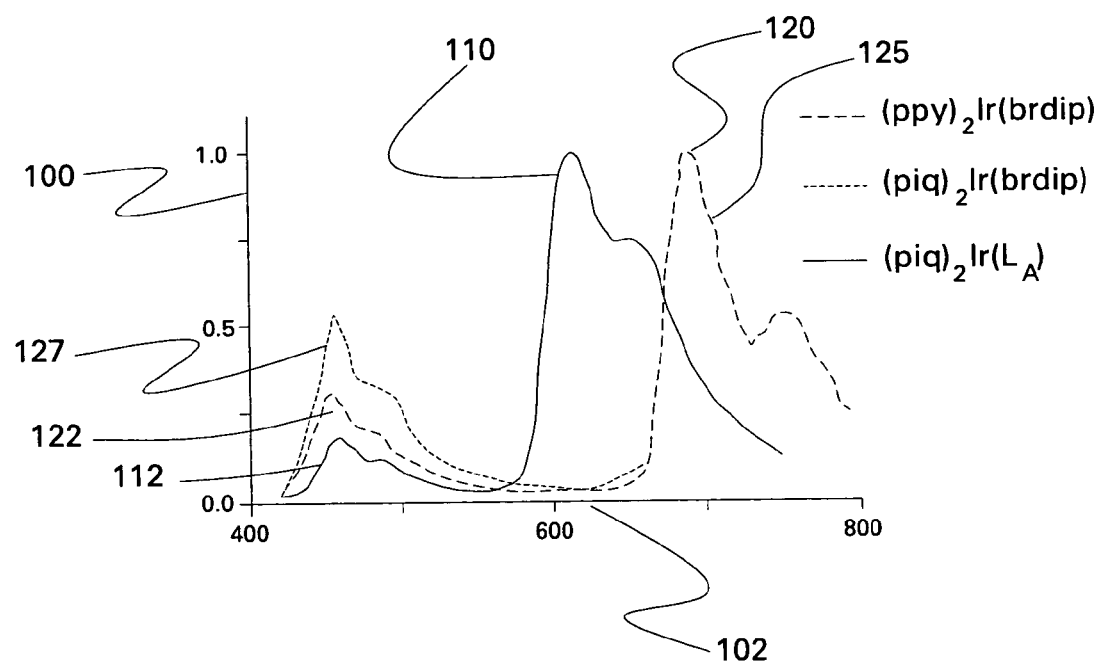
FIG. 12 illustrates the photoluminescent behavior of a film comprising an organic iridium complex provided by the present invention and two films comprising reference compounds.

Next, films were prepared from a xylene solution containing about 3 percent by weight of a blue emissive photoluminescent polymer, BP105 available from Sumation, and one of the organic iridium complex XXVI, the dipyrrin complex LVIII, or the dipyrrin complex LIX. The photoluminescence spectrum of each film was measured using an Edinburgh Instruments F920 fluorimeter, with a xenon lamp excitation source the wavelength of which was selected using a monochromator. The bandpass of the excitation source was on the order of 1-3 nm and was centered at 390 nm. The emitted light was detected using a photomultiplier tube coupled to a single monochromator (with comparable bandpass to the excitation monochromator) filtered by and additional 3 mm yellow glass plate (Corning 3-73) that served to filter out the primary 390 nm excitation source. The spectral response of the monochromator and photomultiplier tube (PMT) were calibrated against a known spectral standard by the manufacturer (Edinburgh Instruments). The three photoluminescence spectra are shown in FIG. 12.

The difference in the color, i.e., the triplet emission maximum ($\lambda_{max}$), for each iridium complex is clearly seen. The organic iridium complex XXVI emitted at a $\lambda_{max}$ of 613 nm (spectrum labeled 110 solid line in FIG. 12) while both dipyrrin-containing iridium complexes, LIX ((ppy)$_2$Ir(brdip)) and LVIII ((piq)$_2$Ir(brdip)), emitted at the same $\lambda_{max}$ centered at 691 nm (items labeled 120 and 125 in FIG. 12, respectively). The data demonstrate that in dipyrrin-containing complexes the emissive triplet energy state is dominated by the dipyrrin ligand. The emissive triplet energy state can be said to dominate when the wavelength of the emitted light is largely independent of the structure of the cyclometallated ligand. For example, while most complexes that employ the phenylisoquinoline derived ligand (piq) display a peak emission in the range from about 590 nm to about 630 nm, dipyrrin complexes comprising piq ligands emit at much longer wavelengths, for example a peak emission centered at about 690 nm. Thus it appears that the dipyrrin complexes tend to be limited to light emission at wavelengths longer than about 690 nm. It has been discovered that organic iridium complexes and polymeric organic iridium complexes of the present invention tend to exhibit a peak emission in the range from about 560 nm to about 630 nm, a range considered highly desirable by those skilled in the art, since visible red light emission (from about 605 nm to about 620 nm) is highly prized. It has also been observed that the organic iridium complexes and polymeric organic iridium complexes of the present invention are tolerant of a variety of structural variations and still emit light having a peak emission in the range from about 560 nm to about 630 nm. In one embodiment, the organic iridium compositions of the present invention emit light having a peak emission in the range from about 605 nm to about 620 nm.

The quantum efficiency of energy transfer from the photoluminescent polymer to the organic iridium complex XXVI was estimated to be about 75% by comparing the residual area under the band at 450 nm (item labeled 112 in FIG. 12) which corresponds to the blue emissive band for the photoluminescent polymer to that of the area under bands centered at 613 nm which corresponds to the emission from the organic iridium complex XXVI. The corresponding blue emission bands for films comprising the dipyrrin complexes (labeled 122 and 127 in FIG. 12) indicate that light producing energy transfer from the photoluminescent polymer to the dipyrrin complexes LVIII and LIX is less efficient than to complex XXVI. The results obtained from the film containing organic iridium complex XXVI suggest that energy transfer from the excited state photoluminescent polymer to the organic iridium complexes of the present invention is highly efficient. Moreover, in a variety of embodiments, light emission from the organic iridium complexes of the present invention such as XXVI occurs in a highly desirable wavelength range from about 600 nm to about 630 nm.

Example 42

Figure 13:
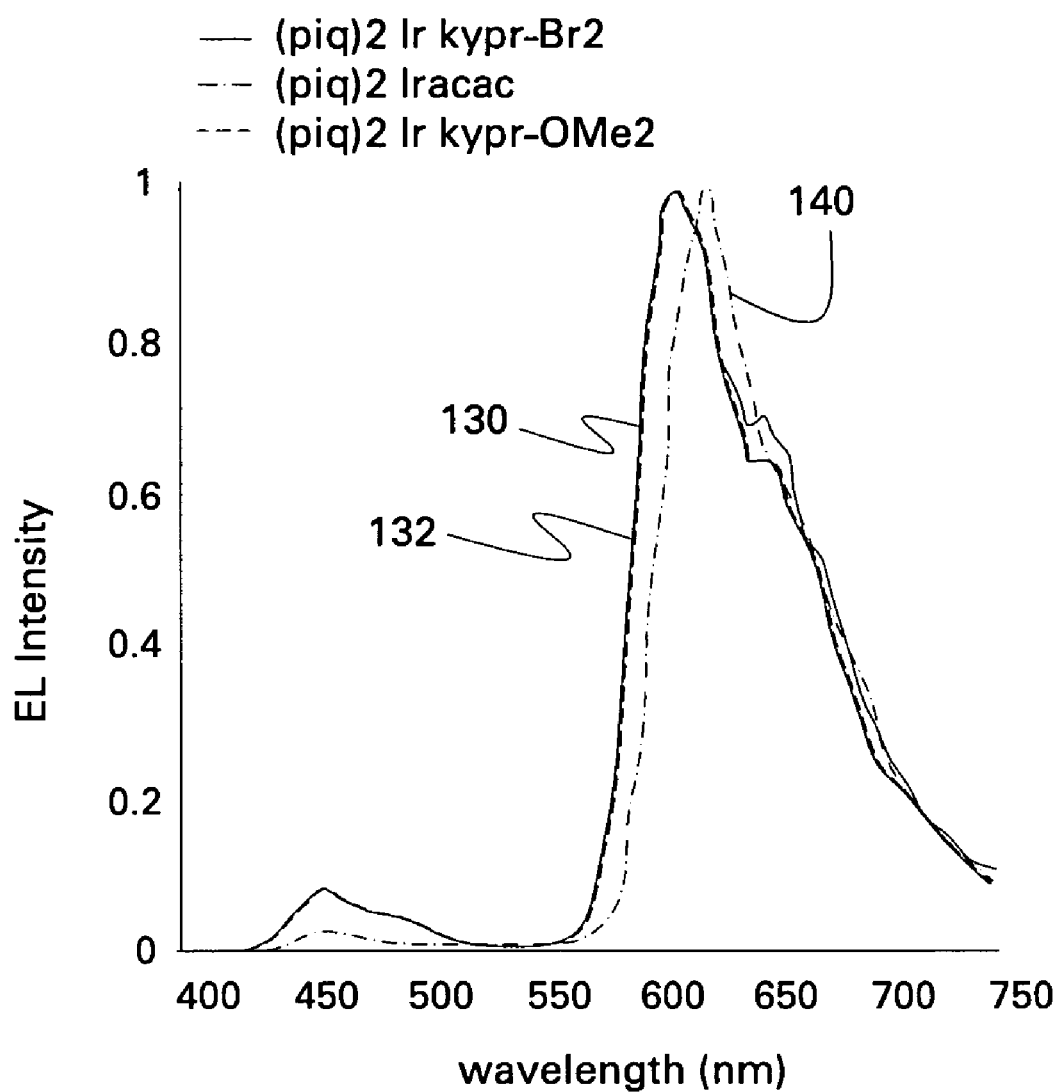
FIG. 13 illustrates the electroluminescence spectra of two OLED devices provided by the present invention and a reference OLED device.

The performance of two organic iridium complexes, XXVII comprising a 3,5-dibromobenzoylpyrrolic ancillary ligand and XIV comprising a 3,5-dimethoxybenzoylpyrrolic ancillary ligand, was probed by preparing OLED devices comprising one of compounds XXVII and XIV and comparing the OLED devices to an identical OLED device containing the known organic iridium complex (piq)$_2$Ir(acac). The devices were each prepared as described in Example 44 below and differed only in the chemical structure of the organic iridium complex employed. The electroluminescence spectrum for each of the OLED devices is shown in FIG. 13. The electroluminescence spectra are normalized so that the peak intensity equals 1 in each spectrum. The electroluminescence spectra may be conveniently summarized by two parameters, the CIE X and Y coordinates, which are given in Table 23 below.

TABLE 23

OLED Device Performance as a Function of Organic Iridium Complex Structure

| Organic Iridiun Complex | Substitution Pattern* | CIE X | CIE Y | LPW |
|---|---|---|---|---|
| XIV | 3,5-dimethoxy | 0.638 | 0.333 | 6.21308 |
| (piq)$_2$Ir(acac) | — | 0.655 | 0.315 | 4.64689 |
| XXVII | 3,5-dibromo | 0.607 | 0.326 | 1.04806 |

*Substitution pattern on benzoyl moiety of the ketopyrrolic ligand. The cyclometallated ligands were derived from 1-phenylisoquinoline in each case The devices containing organic iridium complexes XXVII or XIV exhibit nearly identical electroluminescence spectra (See spectra labeled 130 and 132 in FIG. 13. The electroluminescence spectra nearly overlap in the region 550 nm-750 nm) and the peak maxima are blue shifted relative to the device containing (piq)$_2$Ir(acac). The blue shift observed here is noteworthy in that it results in better eye sensitivity to the emitted light. It is also interesting to note that the OLED device containing the organic iridium complex comprising the 3,5-dibromobenzoyl moiety exhibits less overall red emission than does the OLED device containing the organic iridium complex comprising the 3,5-dimethoxybenzoyl moiety. Thus the benzoyl moiety provides a particularly convenient structural feature as the functionality arrayed on the benzoyl moiety may in certain embodiments be varied without changing the emission wavelength.

Figure 14:
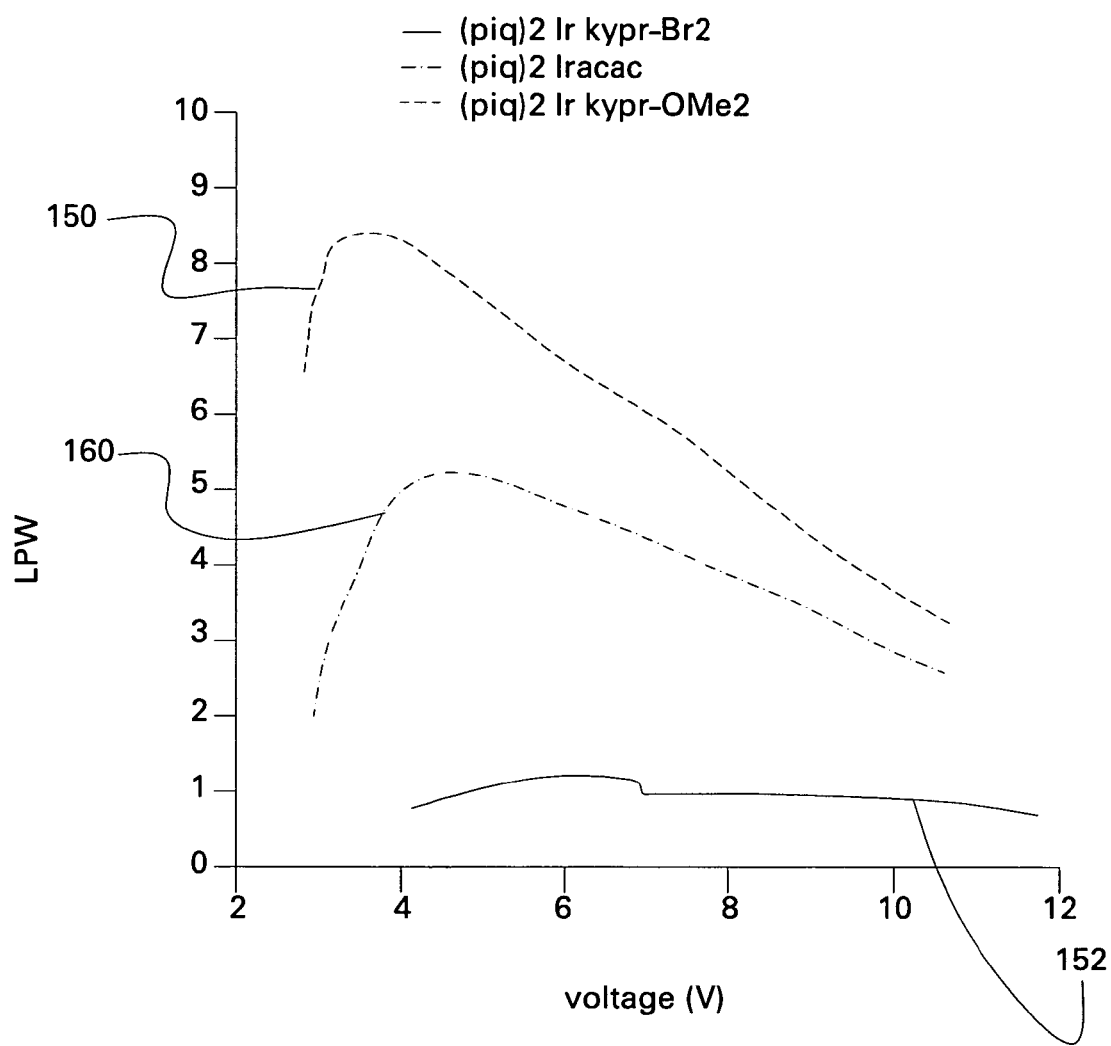
FIG. 14 illustrates a plot of lumens per watt (LPW) versus voltage of two OLED devices of the present invention and a reference OLED device.
Figure 15:
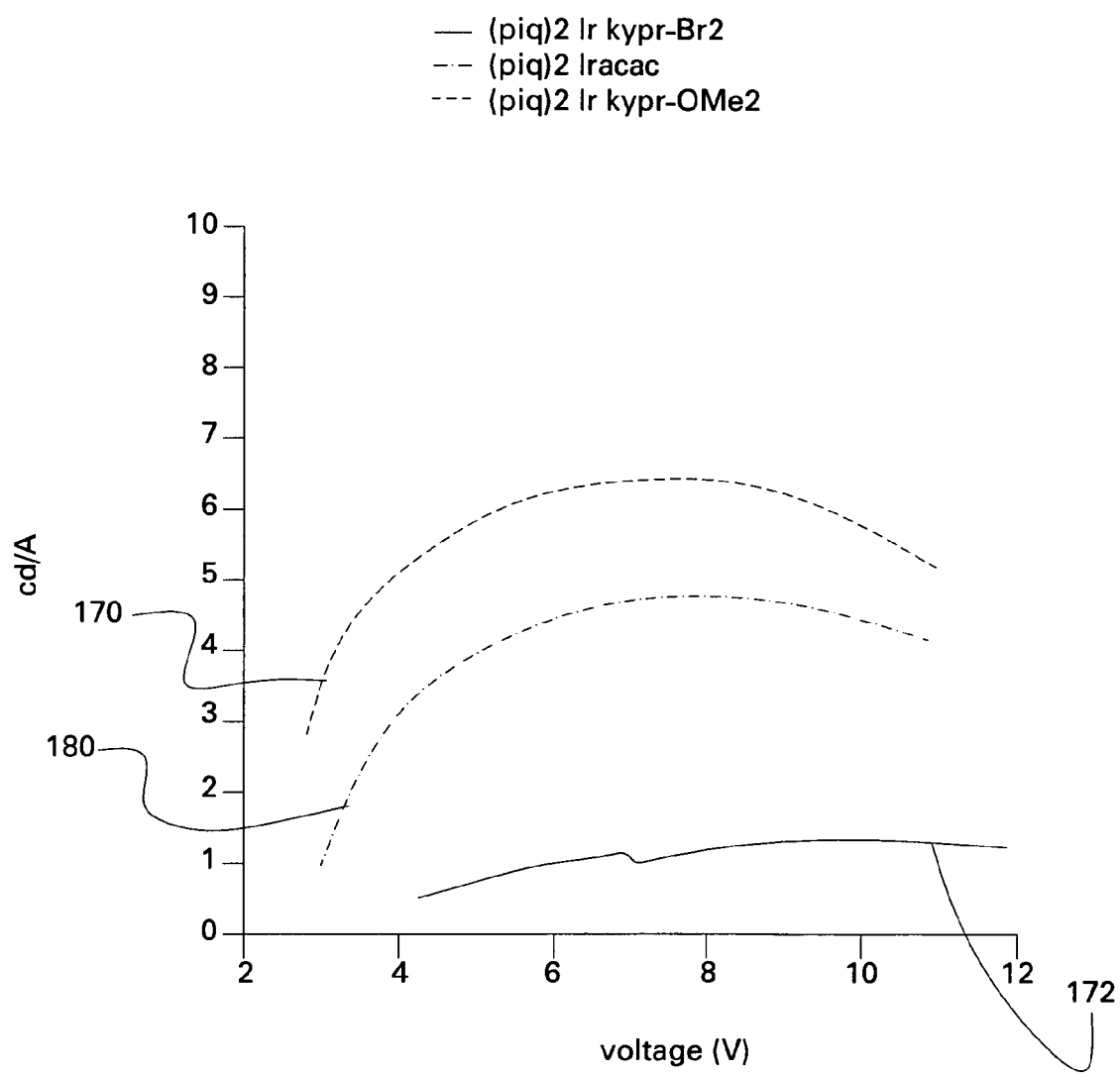
FIG. 15 illustrates a plot of relative brightness in candela per Ampere (cd/A) versus voltage of two OLED devices of the present invention and a reference OLED device.

FIG. 14 provides LPW and relative brightness in candela per Ampere (cd/A) to the brightness of a corresponding device. In principle, the effective brightness of each device is related to the quantum efficiencies and stabilities of the individual organic iridium complexes. For each of the devices the brightness and current versus applied voltage were measured using a Keithley 236 Source Measure unit and a silicon diode coupled to a picoammeter (Keithley). The current response of the diode was converted to OLED brightness (cd/m$^2$) through calibration of the silicon diode against a Minolta LS 100 Luminance meter and by measuring the active area of the OLED. FIG. 14 illustrates the LPW data obtained for each device. FIG. 15 illustrates the "cd/A" brightness data for each device plotted as a function of the applied voltage. The cd/A brightness measures how efficiently injected charge is converted light the eye can see, the LPW is a power efficacy metric (how much visible light is generated for a certain amount of input power). The LPW data contains the effect of both the operating voltage and the charge to visible light conversion efficiency. The data in FIGS. 14 and 15 illustrate that the device containing the organic iridium complex XIV has better luminous efficacy than the (piq)$_2$Ir(acac) containing device, both in terms of cd/A and LPW.

In the following Examples (Examples 43-52) film layers were typically prepared from xylene solutions containing from about 0.1% to about 2% solids. Solutions containing a polymer and an organic iridium composition (dye) typically had a dye to polymer ratio of about 20 parts by weight polymer to 1 parts by weight dye). Care was taken to ensure that prior to operation of the finished OLED device oxygen and water were excluded. Evaporated NaF thicknesses are nominal and vary between about 3.5 nm and about 7 nm (as measured on a calibrated quartz crystal microbalance) in the devices presented here.

Reference Example 43

Preparation Of Reference OLED Device Fabricated Without The Inclusion Of An Iridium Complex: A layer of PEDOT/PSS (Baytron P VP 8000, a poly(3,4-ethylenedioxythiophene)-poly(styrenesulfonate) obtained as a solution from HC Starck, Inc.) having a thickness of about 60 nm was deposited by spin-coating onto clean, UV-Ozone treated, 2.5 cm×2.5 cm ITO patterned glass substrates. The coated substrates were then baked on a hot plate in air for 30 minutes at 160° C. A layer of F8-TFB (an octylfluorene-triarylamine copolymer obtained from Sumation, Inc.) hole transporter layer having a thickness of about 10-20 nm was then spin-coated atop the PEDOT/PSS coated substrates. The F8-TFB-PEDOT/PSS coated substrates were then baked on a hot plate in argon for 30 minutes at 160° C. A layer comprised of the electroluminescent polymer BP79 blended with SR454 acrylate (obtained from Sartomer, Inc.) was then spin-coated from a xylene solution atop the F8-TFB layer. The weight ratio of BP79 to SR454 acrylate was about 7:3. This layer on the F8 TFB-PEDOT/PSS coated substrates was cured by exposing it for 1 minute under argon to shortwave ultraviolet radiation from a UVP model R-52G 254 nm source UV lamp. The filter of the lamp had been removed and the substrates were positioned during curing at a distance of about 0.5 cm directly below the UV grid source. The intensity of the lamp was not calibrated but was estimated to be about 25 mW/cm$^2$ at the 254 nm wavelength believed necessary for curing the SR454 acrylate monomer. The estimated thickness of the cured layer was 40 nm. A final layer of BP157 (an electroluminescent polymer available from Sumation) was deposited by spin casting from a xylene solution of the electroluminescent polymer. Following evaporation of the xylene the final layer was a film having a thickness of about 40 nm.

The coated substrates were then placed into a bell jar evaporator, and the system was pumped until a pressure of about 1×10$^{-6}$ torr was obtained. A layer of sodium fluoride about 7 nm thick (as measured via a calibrated quartz crystal microbalance) was then deposited atop the final layer of the coated substrates by physical vapor deposition. Subsequently, a layer of aluminum metal about 130 nm thick was deposited atop the sodium fluoride layer by vapor deposition under vacuum to form the cathode component of the OLED.

Example 44

OLED Device Fabricated With The Inclusion Of Organic Iridium Complex XIV As A Small Molecule Dopant: An OLED was prepared as described in Reference Example 43 except that the final BP 157 polymer layer was replaced with a layer that included the red emitting organic iridium complex XIV (i.e. the organic iridium complex comprising cyclometallated ligands derived from 1-phenylisoquinoline and an ancillary ligand derived from 2-(3,5-dimethoxybenzoyl)pyrrole). The film comprising organic iridium complex XIV was about 40-50 nm in thickness was prepared by spin casting a xylene solution containing the BP157 electroluminescent polymer and organic iridium complex in a weight ratio of to dye of 20:1 (polymer:iridium complex). Following deposition of the layer containing the polymer and organic iridium complex, a bilayer (NaF, Al) cathode was deposited as in Reference Example 43.

Example 45

OLED Device Fabricated With The Inclusion Of Polymeric Organic Iridium Complex XLVI: An OLED was prepared as in Reference Example 43 except that the final BP 157 polymer layer was replaced with a layer consisting of polymeric organic iridium complex XLVI. The film containing the polymeric organic iridium complex had a thickness of from about 20 nm to about 80 nm and was prepared by spin casting a solution of the polymeric organic iridium complex in xylene onto coated substrates. A bilayer (NaF, Al) cathode was deposited as in Reference Example 43.

Reference Example 46

Reference OLED Device Fabricated Without SR454 and Organic Iridium Composition: A layer of PEDOT/PSS on 2.5 cm×2.5 cm ITO patterned glass substrates was prepared as described in Reference Example 43. A 10-20 nm thick F8-TFB (Sumation, Inc.) hole transporter layer was then spin-coated atop the PEDOT/PSS. The F8-TFB-coated substrates were then baked on a hot plate in argon for 30 minutes at 160° C. A final layer of an electroluminescent polymer, BP 209 (Sumation), having a thickness of approximately 40-50 nm) was deposited via spin casting from a xylene solution atop the F8-TFB layer. A bilayer (NaF, Al) cathode was deposited as in Reference Example 43 with the exception that the NaF layer was approximately 3.5 nm in thickness instead of 7 nm. Prior to the deposition of the final aluminum layer, the multilayer assembly was subjected to two thermal treatments at about 13° C. that were about 10 min in duration, one such treatment just prior to NaF deposition and one following NaF deposition.

Example 47

OLED Device Of Reference Example 46 Including An Additional Layer Of Polymeric Organic Iridium Complex LV: Patterned glass substrates coated with F8-TFB/PEDOT/PSS ITO were prepared as in Reference Example 43. A layer (10-30 nm) of polymeric organic iridium complex LV and SR454 acrylate was deposited via spin casting from a xylene solution. The weight ratio of polymeric organic iridium complex LV to SR454 was about 7:3. The layer containing polymeric organic iridium complex and SR454 was photo cured under an inert atmosphere using the curing procedure described in Reference Example 43. A final layer of an electroluminescent polymer, BP 209 (a blue emissive polymer available from Sumation), having a thickness of 40-50 nm was deposited via spin casting from solution atop the cured SR454-polymeric organic iridium complex LV layer. A bilayer (NaF, Al) cathode was deposited as in Reference Example 46.

Example 48

OLED Device Of Example 47 Further Comprising An Interlayer Between The Layer Containing The Polymeric Organic Iridium Complex LV And The Blue Emissive Layer: Patterned glass substrates coated with PEDOT/PSS ITO were prepared as in Reference Example 43. Next, a layer (approximately 10-30 nm thick) containing F8-TFB (Sumation, Inc.) mixed with SR454 (the weight ratio of F8-TFB to SR454 was about 7 to 3) was then deposited by spin-coating from solution and subsequently photo cured as in Example 43. Next a layer (10-30 nm) of polymeric organic iridium complex LV and SR454 acrylate was deposited and cured as in Example 47. Next, a second layer (approximately 10-30 nm thick) of F8-TFB (Sumation, Inc.) mixed with SR454 (the weight ratio of F8-TFB to SR454 was about 7 to 3) was then spin-coated from solution atop the cured layer containing the polymeric organic iridium complex LV. This second layer of F8-TFB and SR454 was then photo cured under an inert atmosphere using the curing procedure described in Reference Example 43 to provide the cured "interlayer". A final layer of BP 209 of 40-50 nm thickness was deposited via spin casting from solution atop the cured F8-TFB-containing interlayer. A bilayer (NaF (3.5 nm), Al (130 nm)) cathode was deposited as in Reference Example 46 with the exception that just prior to NaF deposition, the polymer layer structure was subjected to a thermal treatment at about 13° C. of between 10 to 20 min in duration.

Example 49

OLED Device: A layer of a hole injecting material, Air Products HIL conducting polymer (available from Air Products), approximately 60 nm thick was spin coated at 2000 rpm onto a clean, UV-Ozone treated, 2.5 cm×2.5 cm ITO patterned glass substrate and the coated substrate was then annealed at 160° C. for 15 minutes under ambient conditions. Next a 10-30 nm thick layer of a hole transport material BP-377 (Sumation, Inc.) mixed with SR454 triacrylate (weight ratio 7:3) was spin-coated atop the hole injecting layer. The coated assembly was then photo cured under an inert atmosphere using the curing procedure described in Reference Example 43. Next a 10-30 nm layer of a mixture of polymeric organic iridium complex LV and SR454 (weight ratio 7:3) was deposited via spin casting atop the BP-377 containing layer. This assembly was photo cured under an inert atmosphere. Next a 20 nm thick layer of a mixture a F8-TFB hole transport polymer (Sumation, Inc.) and SR454 (weight ratio 7:3) was spin-coated from a xylene solution atop the layer containing the polymeric organic iridium complex LV and the assembly was again photo cured under an inert atmosphere. A final organic layer (40-50 nm thick) of a blue light emitting electroluminescent polymer, BP 209 (Sumation), was deposited via spin casting from xylene solution atop the F8-TFB containing layer. A bilayer (NaF, Al) cathode was deposited as in Reference Example 48.

Example 50

The OLED Device Of Example 49 Wherein The BP 209 Containing Layer Further Comprised A Deuterated Organic Iridium Complex: A clean, UV-Ozone treated, 2.5 cm×2.5 cm ITO patterned glass substrate coated with a first organic layer containing a hole injecting material, Air Products HIL conducting polymer, a second organic layer containing BP 377, a third organic layer containing polymeric organic iridium complex LV, and a fourth organic layer containing F8-TFB was prepared as in Example 49 including all photo curing steps. Next a 40-50 nm film was deposited by spin casting a xylene solution of the BP 209 polymer and a deuterated analog of organic iridium complex XXX (comprised $D_{10}$-piq ligands) atop the F8-TFB hole transport layer. The BP 209 polymer and the organic iridium complex were present in the xylene solution in a weight ratio of about 20 to 1. A bilayer (NaF, Al) cathode was deposited as in Reference Example 49.

Example 51

The OLED Device Of Example 50 Prepared Without A Polymeric Organic Iridium Complex LV: A clean, UV-Ozone treated, 2.5 cm×2.5 cm ITO patterned glass substrate coated with a first organic layer containing the hole injecting material and a second organic layer containing BP 377 hole transport material was prepared as in Example 49. Next, a 10-30 nm thick layer of F8-TFB (Sumation, Inc.) hole transport material mixed with SR454 (ratio 7:3) was spin-coated atop the BP 377 containing layer. The assembly was then photo cured under an inert atmosphere using the curing procedure described in Reference Example 43. A xylene solution containing the blue emissive polymer BP 209 and organic iridium complex XXX in a weight ratio of about 20 to 1 was spin cast atop the F8-TFB containing layer. A bilayer (NaF, Al) cathode was deposited as in Reference Example 49.

Example 52

The OLED Device Of Example 51 Comprising Deuterated Organic Iridium Complex LVII: A clean, UV-Ozone treated, 2.5 cm×2.5 cm ITO patterned glass substrate coated with a first organic layer containing the hole injecting material, a second organic layer containing hole transport material BP 377, and a third organic layer containing F8-TFB hole transport material was prepared as in Example 49 including all photo curing steps. Next a 40-50 nm film was deposited by spin casting a xylene solution of the blue light emitting electroluminescent polymer BP 209 and the deuterated organic iridium complex LVII atop the F8-TFB hole transport layer. The BP 209 polymer and the organic iridium complex were present in the xylene solution in a weight ratio of about 20 to 1. A bilayer (NaF, Al) cathode was deposited as in Reference Example 43 with the exception that the NaF layer was approximately 3.5 nm in thickness instead of 7 nm.

Table 24 provides data on the performance of the OLED devices prepared and compares the performance of the OLEDs of reference Examples 43 and 46 with the OLEDs of Examples 44, 45, and 47-52 which present various aspects of the OLED devices provided by the present invention. The color of light emitted by each OLED device sample was measured using a calibrated spectrometer while operating the device over a range of from about 390 nm to about 750 nm at a current density of about 1 mA. A qualitative assessment of the color is present in the rightmost column of Table 24. For this qualitative assessment a device was considered "blue" if the integrated intensity in the region between 390 nm-550 nm>80% of the total intensity, "red" if the integrated intensity in the region 390 nm-550 nm was <15% of the total and "red-blue" for other devices. The luminous efficiency, Lumens per Watt (LPW), at the 1 mA current density is presented in Table 24 as well. For the LPW measurements the luminous output was measured using a silicon diode calibrated against a Minolta LS100 luminance meter. To convert from cd/m² as measured on the luminance meter to lumens, a Lambertian emission pattern was assumed and the following equation was used. The electrical input was measured using a Keithley 237 Source measure unit.

Lumens=$(cd/m^2)\times$(device area)$\times(\pi)$

TABLE 24

| | OLED Device Performance Characteristics | | | |
|---|---|---|---|---|
| Example | CIE X | CIE Y | LPW | Color of Emitted Light |
| Reference Example 43 | 0.178 | 0.257 | 4.9 | Blue |
| Example 44 | 0.638 | 0.333 | 6.2 | Red |
| Example 45 | 0.571 | 0.336 | 2.9 | Red |
| Reference Example 46 | 0.137 | 0.204 | 9.0 | Blue |
| Example 47 | 0.502 | 0.309 | 6.0 | Red-Blue |
| Example 48 | 0.273 | 0.238 | 6.1 | Red-Blue |
| Example 49 | 0.215 | 0.256 | 6.0 | Red-Blue |
| Example 50 | 0.656 | 0.334 | 8.5 | Red |
| Example 51 | 0.657 | 0.333 | 9.8 | Red |
| Example 52 | 0.658 | 0.332 | 9.9 | Red |

The data provided in Table 24 illustrate the suitability of the organic iridium compositions provided by the present invention for use in OLED devices and illustrate the unique performance characteristics of OLED devices containing such compositions. The organic iridium compositions of the present invention are especially useful in the reparation of OLED devices which exhibit primarily red emission and these OLED devices can have equivalent or better efficiency (as measured in LPW) than the reference blue devices. Further, by appropriate choice of device design, the ratio of blue fluorescent emission to red phosphorescent emission can be varied without a major loss of efficiency.

Example 53

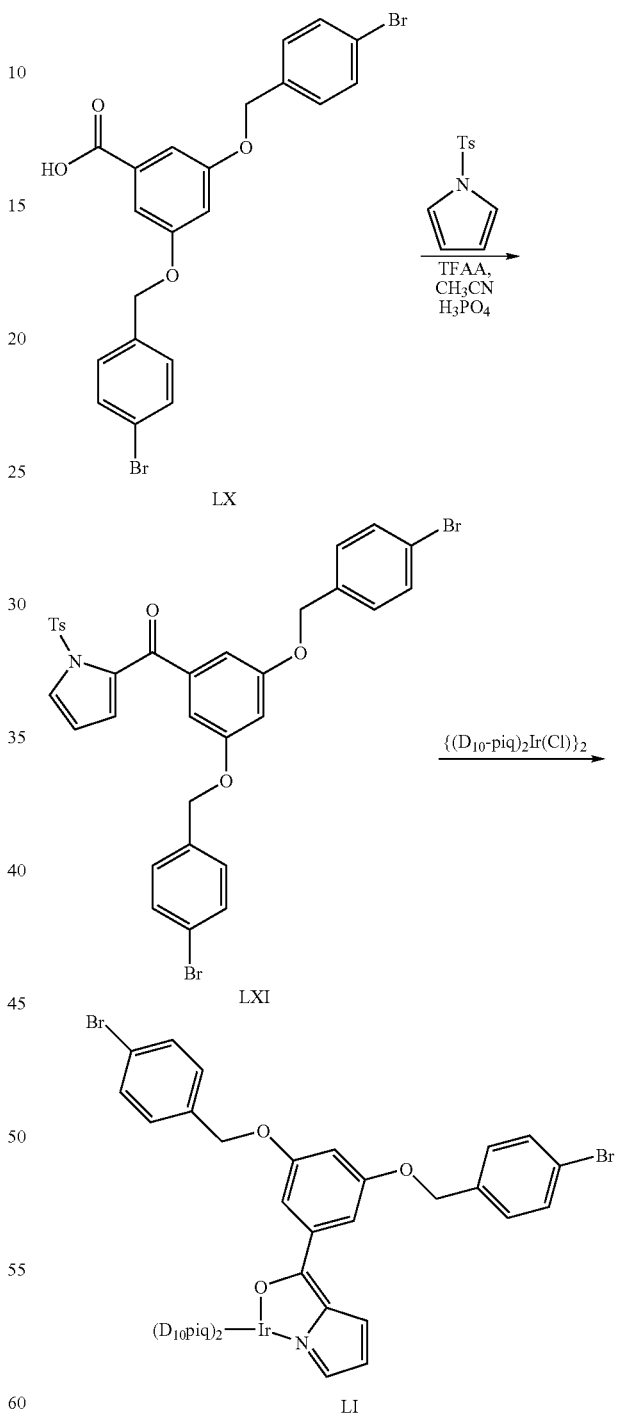

Deuterated Organic Iridium Complex LI: The starting 3,5-Bis(4-bromobenzyloxy)benzoic acid LX was prepared according to literature procedure. (M. Kawa, J. M. Fréchet, *Chem. Mater.*, 1998, 10, 286-296). To a stirred suspension of the carboxylic acid LX (8.90 g, 18.0 mmol) in a mixture of CH$_3$CN (30 mL) and CH$_2$Cl$_2$ (30 mL) was added trifluoroacetic anhydride (5.10 mL, 36.0 mmol). In a separate reaction flask, H$_3$PO$_4$ (1.25 mL, 18.0 mmol) was added at 0° C. with stirring to TFAA (5.10 mL, 36.0 mmol). The mixture was stirred at 0° C. until it became homogenous, after which it was added directly to the CH$_3$CN/CH$_2$Cl$_2$ solution containing the benzoic acid derivative. The resultant mixture was stirred for 5 minutes. N-(4-toluenesulfonyl)-pyrrole (4.00 g, 18 mmol) was then added and the mixture was stirred at room temperature for 10 hrs. Solvents were removed on a rotary evaporator, and the residue was treated a second time with a mixture of H$_3$PO$_4$/TFAA as before. After stirring at room temperature for 2 h, the reaction was neutralized by adding a saturated solution of NaHCO$_3$. Thereafter the mixture was concentrated until the product separated from solution. The product 2-(3,5-bis(4-bromobenzyloxy)benzoyl)-N-(4-toluenesulfonyl)-pyrrole LXI was collected by vacuum filtration, washed with water and dried. The crude solid was dissolved in EtOAc and decolorized with charcoal. After removal of solvent the resultant solid was recrystallized from CH$_2$Cl$_2$/EtOH to afford the product LXI as fine white needles. (6.30 g, 50%). $^1$H NMR (400 MHz, CD$_2$Cl$_2$, 25° C.) δ2.45 (s, 3H), 5.03 (s, 4H), 6.34 (t, 1H), 6.58 (m, 1H), 6.79 (t, 1H), 6.98 (d, 2H), 7.30 (d, 4H), 7.39 (d, 2H), 7.52 (d, 4H), 7.75 (m, 1H), 7.94 (d, 2H); $^{13}$C NMR (100 MHz, CD$_2$Cl$_2$, 25° C.) δ22.0, 70.1, 107.5, 109.3, 111.3, 122.4, 125.7, 128.8, 129.7, 130.0, 130.1, 132.3, 133.2, 136.6, 136.8140.4, 145.8, 160.0, 184.0; HRMS (MALDI): m/z 696.1087 (100) (M+H)$^+$.

Deuterated Organic iridium complex LI: To a stirred solution of 2-(3,5-bis(4-bromobenzyloxy)benzoyl)-N-(4-toluenesulfonyl)-pyrrole LXI (315.0 mg, 0.372 mmol) in 2-methoxyethanol (4 mL) was added solid sodium hydride (40.0 mg, 1.67 mmol) and the resultant yellow solution was stirred for 5 minutes. The chloride-bridged deuterated cyclometallated iridium dimer intermediate {(D$_{10}$-piq)$_2$Ir(μ-Cl)}$_2$ (215 mg, 0.160 mmol) was added and the mixture was then heated at 80° C. for 2 h. The dark red reaction mixture was cooled to room temperature and the solvents were removed to dryness. The crude product was chromatographed on silica gel (CH$_2$Cl$_2$/Hexanes) to afford deuterated organic iridium complex LI. Yield (250 mg, 67%). $^1$H NMR (400 MHz, CD$_2$Cl$_2$, 25° C.) δ5.00 (d, 4H), 6.29 (m, 1H), 6.41 (s), 6.45 (s), 6.53 (s, 1H), 6.69 (t, 1H), 7.10 (d, 2H), 7.28 (d, 4H), 7.49 (d, 4H), 7.72 (m), 7.90 (s), 7.94 (s), 8.28 (m), 8.98 (m); HRMS (MALDI): m/z 1159.1722 (100) (M)$^+$.

Example 54

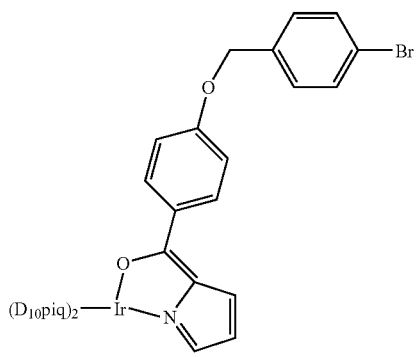

LXII

Deuterated Organic Iridium Complex LXII: 4-(4-bromobenzyloxy)benzoic acid was prepared analogously to carboxylic acid LX and was converted to deuterated organic iridium complex LXII as in Example 53. Yield (232 mg, 80%). $^1$H NMR (500 MHz, CD$_2$Cl$_2$, 25° C.) δ 5.06 (s, 2H), 6.31 (m, 1H), 6.42 (s), 6.45 (s), 6.51 (s, 1H), 7.00 (d, 2H), 7.18 (m, 1H), 7.31 (d, 2H), 7.50 (d, 2H), 7.72 (m), 7.88 (s), 7.92 (s), 7.95 (d, 2H), 8.27 (m), 8.99 (m); HRMS (MALDI): m/z 975.1735 (100) (M)$^+$.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A composition comprising at least one organic iridium complex of structure I

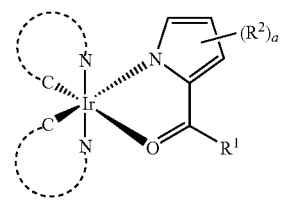

I wherein each of the ligands

is independently at each occurrence a cyclometallated ligand which may be the same or different;

R$^1$ is a C$_3$-C$_{40}$ aromatic radical, a C$_1$-C$_{50}$ aliphatic radical, or a C$_3$-C$_{40}$ cycloaliphatic radical;

R$^2$ is independently at each occurrence a deuterium atom, a halogen, a nitro group, an amino group, a C$_3$-C$_{40}$ aromatic radical, a C$_1$-C$_{50}$ aliphatic radical, or a C$_3$-C$_{40}$ cycloaliphatic radical; and "a" is an integer from 0 to 3.

2. The composition according to claim 1, wherein the cyclometallated ligand is derived from a phenylisoquinoline compound having structure II

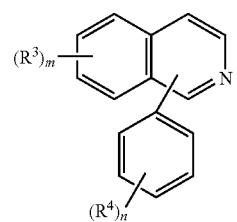

II wherein R$^3$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

$R^4$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"m" is an integer from 0 to 6; and

"n" is an integer from 0 to 5.

3. The composition according to claim 1, wherein the cyclometallated ligand is derived from a 2-phenylpyridine compound having structure III

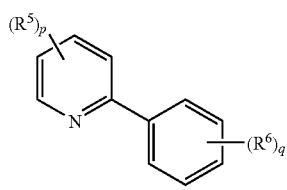

III wherein $R^5$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

$R^6$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"p" is an integer from 0 to 4; and

"q" is an integer from 0 to 5.

4. The composition according to claim 1, wherein the cyclometallated ligand is derived from a styrylisoquinoline compound having structure IV

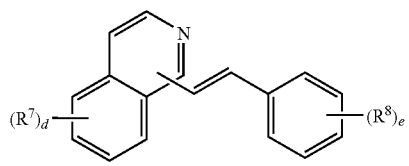

IV wherein $R^7$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

$R^8$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"d" is an integer from 0 to 6; and

"e" is an integer from 0 to 5.

5. The composition according to claim 1, wherein the cyclometallated ligand

is derived from a 1-phenylisoquinoline, a 2-phenylpyridine, a 1-styrylisoquinoline, or a combination thereof.

6. The composition according to claim 1, wherein the cyclometallated ligand is derived from 1-phenylisoquinoline.

7. The composition according to claim 1, wherein the cyclometallated ligand is derived from 2-phenylpyridine.

8. The composition according to claim 1, wherein the cyclometallated ligand is derived from 1-styrylisoquinoline.

9. The composition according to claim 1, wherein said complex comprises a ketopyrrole ligand derived from a ketopyrrole having structure V

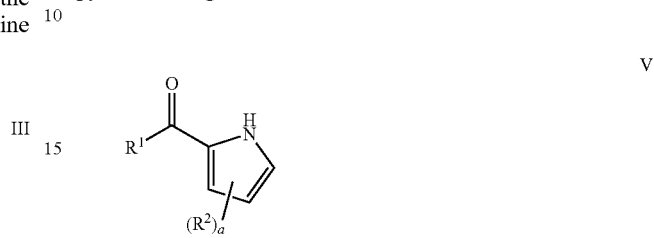

V wherein $R^1$ is a $C_3$-$C_{40}$ aromatic radical, a $C_1$-$C_{50}$ aliphatic radical, or a $C_3$-$C_{40}$ cycloaliphatic radical;

$R^2$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical; and "a" is an integer from 0 to 3.

10. The composition according to claim 1, wherein said complex comprises a ketopyrrole ligand derived from a benzoyl pyrrole compound having structure VI

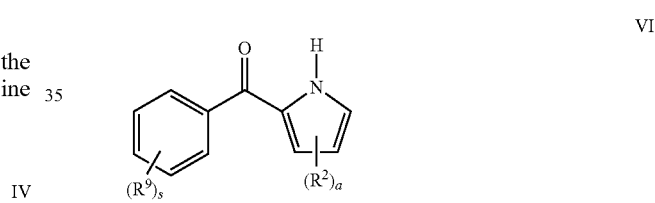

VI wherein $R^2$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

$R^9$ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3; and

"s" is an integer from 0 to 5.

11. The composition according to claim 1, wherein said organic iridium complex has structure VII

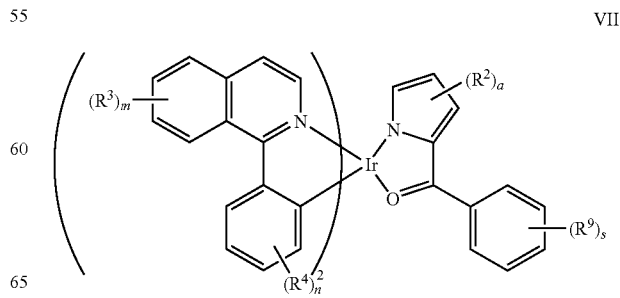

VII wherein R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R³ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁴ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁹ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3;
"m" is an integer from 0 to 6;
"n" is an integer from 0 to 4; and
"s" is an integer from 0 to 5.

12. The composition according to claim 1, wherein said organic iridium complex has structure IX

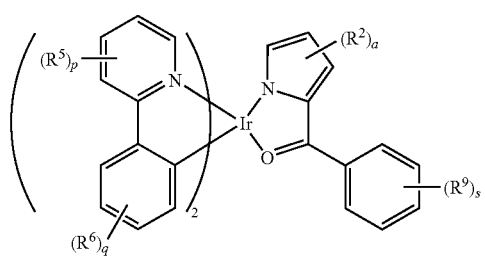

IX wherein R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁵ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁶ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁹ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3;
"p" is an integer from 0 to 4;
"q" is an integer from 0 to 4; and
"s" is an integer from 0 to 5.

13. The composition according to claim 1, wherein said organic iridium complex has structure XI

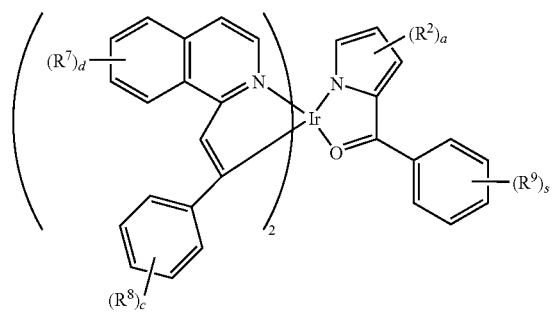

XI wherein R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁷ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁸ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁹ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3;
"d" is an integer from 0 to 6;
"e" is an integer from 0 to 5; and
"s" is an integer from 0 to 5.

14. An electrophosphorescent composition comprising at least one electroactive host material and at least one organic iridium complex of structure I

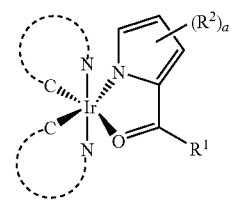

I wherein each of the ligands

is independently at each occurrence a cyclometallated ligand which may be the same or different;

R¹ is a $C_3$-$C_{40}$ aromatic radical, a $C_1$-$C_{50}$ aliphatic radical, or a $C_3$-$C_{40}$ cycloaliphatic radical;

R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical; and "a" is an integer from 0 to 3.

15. The electrophosphorescent composition according to claim 14, wherein said organic iridium complex has structure VII

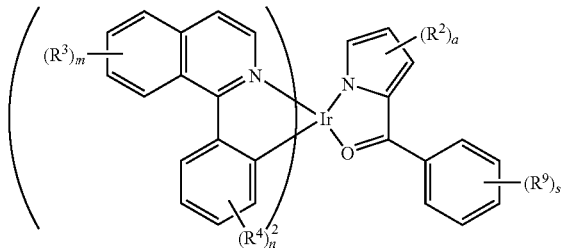

VII wherein R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R³ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁴ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁹ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3;
"m" is an integer from 0 to 6;
"n" is an integer from 0 to 4; and
"s" is an integer from 0 to 5.

16. The electrophosphorescent composition according to claim 14, wherein said organic iridium complex has structure IX

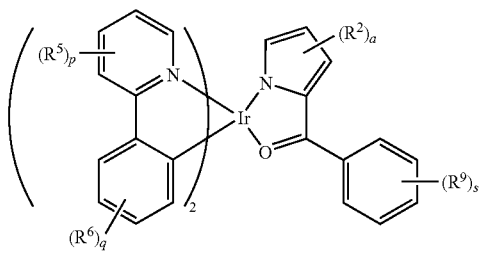

IX wherein R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁵ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁶ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁹ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3;
"p" is an integer from 0 to 4;
"q" is an integer from 0 to 4; and
"s" is an integer from 0 to 5.

17. The electrophosphorescent composition according to claim 14, wherein said organic iridium complex has structure XI

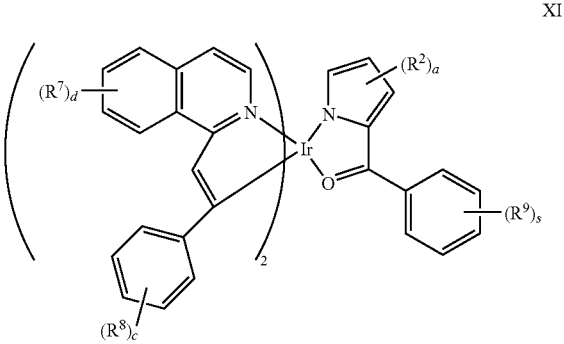

XI wherein R² is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁷ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁸ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

R⁹ is independently at each occurrence a deuterium atom, a halogen, a nitro group, an amino group, a $C_3$-$C_{40}$ aromatic radical, a $C_1$-$C_{50}$ aliphatic radical, or a $C_3$-$C_{40}$ cycloaliphatic radical;

"a" is an integer from 0 to 3;
"d" is an integer from 0 to 6;
"e" is an integer from 0 to 5; and
"s" is an integer from 0 to 5.

18. The electrophorescent composition according to claim 14, wherein the electroactive host material is a blue light emitting electroluminescent organic material.

19. The electrophosphorescent composition according to claim 18, wherein the organic iridium complex is characterized by a lowest accessible triplet state energy T1 and the blue light emitting electroluminescent organic material is characterized by a lowest accessible triplet state energy T2, wherein T1 is less than T2.

20. The electrophosphorescent composition according to claim 14, wherein the organic iridium complex is at least 10 percent deuterated.

21. The electrophosphorescent composition according to claim 14, wherein the organic iridium complex is at least 60 percent deuterated.

22. An organic iridium complex having structure XIV

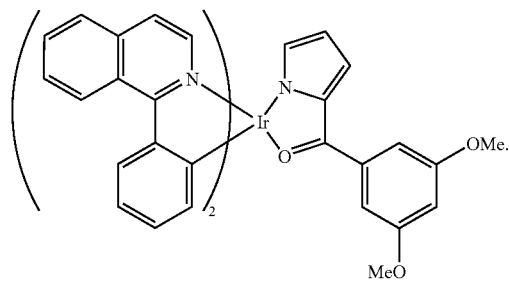

* * * * *

UNITED STATES PATENT AND TRADEMARK OFFICE
CERTIFICATE OF CORRECTION

PATENT NO. : 7,691,292 B2 Page 1 of 4
APPLICATION NO. : 11/504871
DATED : April 6, 2010
INVENTOR(S) : Chichak et al.

It is certified that error appears in the above-identified patent and that said Letters Patent is hereby corrected as shown below:

In Column 4, Line 49, delete "-$C_6H$  $oC(CF_3)_2$" and insert -- -$C_6H_{10}C(CF_3)_2$ --, therefor.

In Column 4, Line 56, delete "$H_2C_6H_{10}$-)," and insert -- $H_2NC_6H_{10}$-), --, therefor.

In Column 7, Line 21, delete "some" and insert -- same --, therefor.

In Column 10, Line 66, delete "$C_3$-$C_4$" and insert -- $C_3$-$C_{40}$ --, therefor.

In Column 12, Line 48, delete "4: and "q" is on" and insert -- 4; and "q" is an --, therefor.

In Column 13, above Line 62, insert -- The compositions of Entries 4a-4d of Table 4 illustrate a variety of styrylisoquinolines having structure IV which may serve as precursors to the cyclometallated ligands of the organic iridium compositions of the present invention. --.

In Column 20, Line 25, delete "on" and insert -- an --, therefor.

In Column 23, Line 27, delete "radical;" and insert -- cycloaliphatic radical; --, therefor.

In Column 23, Line 28, delete "3:" and insert -- 3; --, therefor.

In Column 23, Line 28, delete "6:" and insert -- 6; --, therefor.

In Column 28, Line 64, delete "$R=NMe_2$," and insert -- $R^6=NMe_2$, --, therefor.

Signed and Sealed this

Thirty-first Day of August, 2010

David J. Kappos
*Director of the United States Patent and Trademark Office*

CERTIFICATE OF CORRECTION (continued)
U.S. Pat. No. 7,691,292 B2

In Column 30, Lines 43-46, delete " 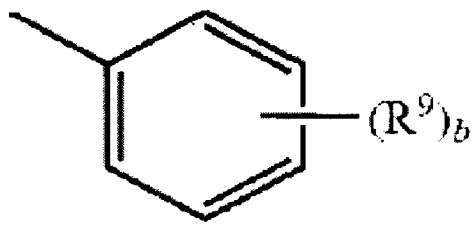 " and insert -- 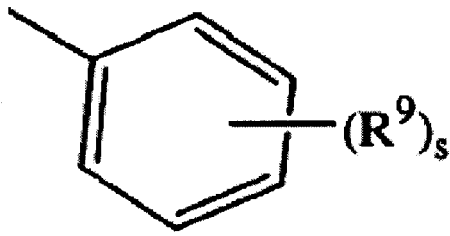 --, therefor.

In Column 30, Line 57, delete "on integer from 0 to 6:" and insert -- an integer from 0 to 6; --, therefor.

In Column 32, Line 5, delete "1e" and insert -- 11e --, therefor.

In Column 34, Line 21, delete "some" and insert -- same --, therefor.

In Column 34, Line 24, delete "$C_3$-$C_{50}$" and insert -- $C_3$-$C_{40}$ --, therefor.

In Column 34, Line 26, delete "on" and insert -- an --, therefor.

In Column 34, Line 26, delete "$C_4$-$C_{40}$" and insert -- $C_3$-$C_{40}$ --, therefor.

In Column 34, Line 28, after "radical;" insert -- and --.

In Column 37, Line 18, delete "VII," and insert -- VIII, --, therefor.

In Column 46, Line 41, delete "some" and insert -- same --, therefor.

In Column 53, Line 46, delete "on" and insert -- an --, therefor.

In Column 59, Line 51, delete "E1" and insert -- EI --, therefor.

In Column 60, Line 58, delete "(20ml 10mL)" and insert -- (20ml:10mL) --, therefor.

In Column 61, Line 8, delete "(80ml 20mL)" and insert -- (80ml:20mL) --, therefor.

In Column 62, in "TABLE 19", last line, delete "161.4.171.0." and insert -- 161.4,171.0. --, therefor.

In Column 65, Line 53, delete "9.8.3" and insert -- 9.83 --, therefor.

In Column 77, Line 17, delete "$M_w$" and insert -- $M_n$ --, therefor.

In Column 81, Line 23, delete "mmol)" and insert -- (0.105mmol) --, therefor.

In Column 82, Line 30, delete "$\lambda_{max}32$" and insert -- $\lambda_{max}=$ --, therefor.

In Column 85, Line 65, delete "(SiO$_2$EtOAc/Hexanes)" and insert -- (SiO$_2$:EtOAc/Hexanes) --, therefor.

In Column 88, under "TABLE 23", Line 3, delete "Iridiun" and insert -- Iridium --, therefor.

In Column 91, Line 5, delete "13°C." and insert -- 130°C. --, therefor.

In Column 91, Line 55, delete "13°C." and insert -- 130°C. --, therefor.

In Column 100, Lines 10-15, in Claim 13", delete " 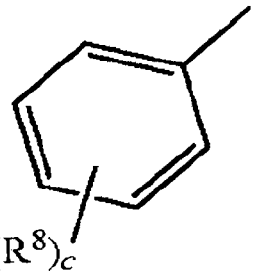 " and insert

-- 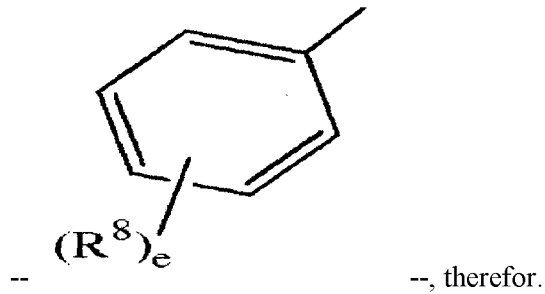 --, therefor.

In Column 102, Lines 29-34, in Claim 17, delete " 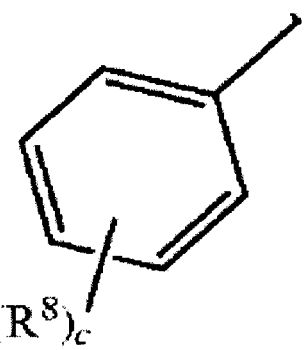 " and insert -- 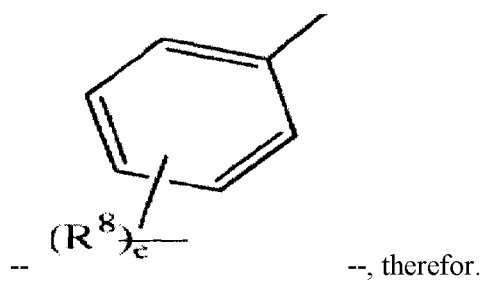 --, therefor.